US010767178B2

(12) United States Patent
Zhu

(10) Patent No.: US 10,767,178 B2
(45) Date of Patent: Sep. 8, 2020

(54) COMPOSITIONS AND METHODS OF USING PIRNAS IN CANCER DIAGNOSTICS AND THERAPEUTICS

(71) Applicant: Yale University, New Haven, CT (US)

(72) Inventor: Yong Zhu, Cheshire, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 16/079,868

(22) PCT Filed: Feb. 27, 2017

(86) PCT No.: PCT/US2017/019741
§ 371 (c)(1),
(2) Date: Aug. 24, 2018

(87) PCT Pub. No.: WO2017/147594
PCT Pub. Date: Aug. 31, 2017

(65) Prior Publication Data
US 2019/0062740 A1 Feb. 28, 2019

Related U.S. Application Data

(60) Provisional application No. 62/300,748, filed on Feb. 26, 2016.

(51) Int. Cl.
*A61K 48/00* (2006.01)
*C07H 21/04* (2006.01)
*C12N 15/113* (2010.01)
*C12Q 1/6886* (2018.01)

(52) U.S. Cl.
CPC .......... *C12N 15/113* (2013.01); *C12Q 1/6886* (2013.01); *C12N 2310/10* (2013.01); *C12N 2310/141* (2013.01); *C12N 2320/10* (2013.01); *C12N 2320/11* (2013.01); *C12Q 2600/106* (2013.01); *C12Q 2600/156* (2013.01); *C12Q 2600/158* (2013.01); *C12Q 2600/178* (2013.01)

(58) Field of Classification Search
CPC ............................ A61K 31/713; C12N 15/113
See application file for complete search history.

(56) References Cited

U.S. PATENT DOCUMENTS

| 9,757,462 B2* | 9/2017 | Kato ....................... A61K 47/26 |
| 2009/0054350 A1 | 2/2009 | Tayot |
| 2013/0022328 A1 | 1/2013 | Gronvall |

FOREIGN PATENT DOCUMENTS

WO 2014152909 9/2014

OTHER PUBLICATIONS

Mita et al. (Journal of Hepatology, 2000, 32, 946-954).*
Lim et al. (Plos One, Jun. 2014, vol. 9, issue 6, e99687, pp. 1-11).*
1000 Genomes Project Consortium, et al., "An integrated map of genetic variation from 1,092 human genomes", *Nature*, 491(7422):56-65 (2012).
Aravin, et al., "A novel class of small RNAs bind to MILI protein in mouse testes", *Nature*, 442(7099):203-07 (2006).
Aravin, et al., "A piRNA Pathway Primed by Individual Transposons Is Linked to De Novo DNA Methylation in Mice", *Mol. Cell*, 31(6):785-99 (2008).
Aravin, et al., "Developmentally regulated piRNA clusters implicate MILI in transposon control", *Science*, 316:744-7 (2007).
Aravin, et al., "A. Cytoplasmic compartmentalization of the fetal piRNA pathway in mice", *PLoS Genet*, 5:e1000764-e (2009).
Bamezai, et al., "The Piwi—piRNA Axis: Pivotal Beyond Transposon Silencing", *Stem Cells*, 30(12):2603-11 (2012).
Brennecke, et al., "An Epigenetic Role for Maternally Inherited piRNAs in Transposon Silencing", *Science*, 322(5906):1387-92 (2008).
Brower-Toland, et al., "Drosophila PIWI associates with chromatin and interacts directly with HP1a", *Genes Dev.*, 7:21(18):2300-11 (2007).
Carmell, et al., "MIWI2 is essential for spermatogenesis and repression of transposons in the mouse male germline", *Dev. Cell*, 12(4):503-14 (2007).
Cheng, et al., "piR-823, a novel non-coding small RNA, demonstrates in vitro and in vivo tumor suppressive activity in human gastric cancer cells", *Cancer Lett.*, 315:12-17 (2012).
Cheng, et al, "piRNA, the new non-coding RNA, is aberrantly expressed in human cancer cells", *Clin. Chim. Acta.*, 412:1621-5 (2011).
Chu, et al., "Identification of novel piRNAs in bladder cancer", *Cancer Lett.*, 356:561-7 (2015).
Cox, et al., "A novel class of evolutionarily conserved genes defined by piwi are essential for stem cell self-renewal", *Genes Dev*, 12(23):3715-27 (1998).
Croce, et al., "Causes and consequences of microRNA dysregulation in cancer", *Nat Rev Genet*, 10(10):704-14 (2009).
Dharap, et al., "Altered expression of PIWI RNA in the rat brain after transient focal ischemia", *Stroke*, 42(4):1105-9 (2011).
Esposito, et al., "piR_015520 Belongs to Piwi-Associated RNAs Regulates Expression of the Human Melatonin Receptor 1A gene", *PLoS One*, 6(7):e22727 (2011).
Freedman, et al., "Admixture mapping identifies 8q24 as a prostate cancer risk locus in African-American men", *PNAS*, 103(38):14068-73 (2006).
Fu, et al., "PIWI-interacting RNA 021285 is involved in breast tumorigenesis possibly by remodeling the cancer epigenome", *Carcinogenesis*, 36:1094-102 (2015).
Fu, et al., "Epigenome-wide analysis of piRNAs in gene-specific DNA methylation", *RNA Biol.*, 11:1301-12 (2014a).
Fu, et al., "Targetome profiling and functional genetics implicate miR-618 in lymphomagenesis", *Epigenetics*, 9(5):730-7 (2014).
Girard, et al., "A germline-specific class of small RNAs binds mammalian Piwi proteins", *Nature*, 442(7099):199-202 (2006).

(Continued)

*Primary Examiner* — Amy H Bowman
(74) *Attorney, Agent, or Firm* — Pabst Patent Group LLP

(57) ABSTRACT

Aberrantly expressed piRNAs, genetically associated piRNAs and their relationship with cancer risk and severity are provided. Compositions and methods of using piRNA for treating cancer are provided. Methods of diagnosing subjects and determining the efficacy of active agents for treating cancer are also provided. Methods of correlating variant piRNA to cancer are also disclosed.

20 Claims, 23 Drawing Sheets

Specification includes a Sequence Listing.

(56) References Cited

OTHER PUBLICATIONS

Grochola, et al., "The stem cell-associated Hiwi gene in human adenocarcinoma of the pancreas: expression and risk of tumour-related death", Br. J Cancer, 99:1083-8 (2008).
GTEx Consortium, et al., The Genotype-Tissue Expression (GTEx) project, Nat Genet, 45:580-5 (2013).
Hartig, et al., "piRNAs—the ancient hunters of genome invaders", Genes Dev., 21(14):1707-13 (2007).
Hashim, et al., "RNA sequencing identifies specific PIWI-interacting small non-coding RNA expression patterns in breast cancer", Oncotarget, 4(5):9901-9910 (2014).
He, et al., "Expression of HIWI in human esophageal squamous cell carcinoma is significantly associated with poorer prognosis", BMC Cancer, 9:426 (2009).
Huang, et al, "Altered expression of piRNAs and their relation with clinicopathologic features of breast cancer", Clin. Transl. Oncol., 15(7):563-8 (2012).
Huang, et al., "A major epigenetic programming mechanism guided by piRNAs", Dev Cell, 13;24:502-16 (2013).
Ishizu, et al., "Biology of PIWI-interacting RNAs: new insights into biogenesis and function inside and outside of germlines", Genes Dev., 26(21):2361-73 (2012).
Jacobs, et al., "Piwi-interacting RNAs in gliomagenesis: Evidence fro, post-gwas and functional analyses", Cancer Epidemiol. Biomarkers Prev., 25(7):1073-80 (2016).
Jacobs, et al., "Leveraging ethnic group incidence variation to investigate genetic susceptibily to gliomaL a novel candidate SNP approach", Front Gnrt., 3:203 (2012).
Jacobs, et al., "Dysregulated methylation at imprinted genes in prostate tumor tissue detected by methylation microarray", BMC Urol., 13:37 (2013).
Janic, et al., "Ectopic expression of germline genes drives malignant brain tumor growth in Drosophila.", Science, 330(6012):1824-1827 (2010).
Kasinski, et al., "MicroRNAs en route to the clinic: progress in validating and targeting microRNAs for cancer therapy", Nat Rev Cancer, 11(12):849-64 (2011).
Kim, "Small RNAs just got bigger: Piwi-interacting RNAs (piRNAs) in mammalian testes", Genes Dev, 20(15):1-6 (1993).
Kim, et al., "Biogenesis of small RNAs in animals", Nat. Rev. Mol. Cell Biol., 10(2):126-39 (2009).
Kuramochi-Miyagawa, et al., "Ikawa M, et al. DNA methylation of retrotransposon genes is regulated by Piwi family members MILI and MIWI2 in murine fetal testes", Genes Dev., 22(7):908-17 (2008).
Law, et al., "Deep sequencing of small RNA transcriptome reveals novel non-coding RNAs in hepatocellular carcinoma", J Hepatol., 58(6):1165-73 (2013).
Le, et al., "Piwi induces piRNA-guided transcriptional silencing and establishment of a repressive chromatin state", Genes Dev., 27(4):390-99 (2013).
Lee , et al., "Identification of piRNAs in the central nervous system", RNA, 1;17(6):1090-99 (2011).
Li, et al., "Piwil2 modulates the proliferation and metastasis of colon cancer via regulation of matrix metallopeptidase 9 transcriptional activity", Exp Biol Med, 237(10):1231-40 (2011).
Li, et al., "An ancient transcription factor initiates the burst of piRNA production during early meiosis in mouse testes", Mol Cell, 50(1):67-81 (2013).
Liu, et al., "Piwil2 is expressed in various stages of breast cancers and has the potential to be used as a novel biomarker", Intl J Clin Exp Pathol, 3(4):328 (2010).
Liu, et al., "Aberrant methylation of miR-34b is associated with long-term shiftwork: a potential ,ecjanism for increased", Cancer Causes Cont., 26(2):171-8 (2015).
Lu, et al., "MicroRNA let-7a Modifies the Effect of Self-Renewal Gene HIWI on Patient Survival of Epithelial Ovarian Cancer", Mol Carcinog., 55(4):357-65 (2016).
Martinez, et al., "Unique somatic and malignant expression patterns implicate PIWI-interacting RNAs in cancer-type specific biology", Sci Rep, 5:10423. doi: 10.1038/srep10423. (2015).
Mei, "Novel dimensions of piRNAs in cancer", Cancer Lett, 336(1):46-52 (2013).
Moyano, et al., "piRNA involvement in genome stability and human cancer", J hematol Oncol., 8:38 (2015).
Ng, et al., "Piwi-interacting RNAs in cancer: emerging functions and clinical utility", Mollar Cancer, 15:5 DOI 10.1186/s12943-016-0491-9 (2016).
O'Donnell and Boeke, "Mighty Piwis Defend the Germline against Genome Intruders",. Cell, 129(1):37-44 (2007).
Oh, et al., "Clinicopathologic implications of PIWIL2 expression in colorectal cancer",. Korean J of Pathol., 46:318-23 (2012).
Ostrom, et al, "The epidemiology of glioma in adults: a "state of the science" review", Neuro-Oncol, 16(7):896-913 (2014).
Peng, et al., "Beyond transposons: the epigenetic and somatic functions of the Piwi-piRNA mechanism", Curr Opin Cell Biol., 25(2):190-94 (2013).
Peng, et al., "piR-55490 inhibits growth of lung carcinoma by suppressing mTOR signaling.", Tumour Biol., 37(2):2749-2756 (2016).
Qi, et al., "The Yb body, a major site for Piwi-associated RNA biogenesis and a gateway for Piwi expression and transport to the nucleus in somatic cells", J Biol Chem, 286(5):3789-97 (2011).
Rajaraman, et al., "Genome-wide association study of glioma and meta-analysis", Hum Genet., 131:1877-88 (2012).
Rajasethupathy, et al., "A Role for Neuronal piRNAs in the Epigenetic Control of Memory-Related Synaptic Plasticity", Cell, 149(3):693-707 (2012).
Ross, et al., "PIWI proteins and PIWI-interacting RNAs in the soma", Nature, 505(7483):353-59 (2014).
Sai Lakshmi and Agrawal, "piRNABank: a web resource on classified and clustered Piwi-interacting RNAs", Nucleic Acids Res., 36:D173-D7 (2008).
Siddiqi, et al., "Piwis and piwi-interacting RNAs in the epigenetics of cancer", J Cell Biochem., 113:373-80 (2012).
Siomi, et al., "PIWI-interacting small RNAs: the vanguard of genome defence", Nat Rev Mol Cell Biol., 12(4):246-58 (2011).
Sun, et al., "Clinical significance of Hiwi gene expression in gliomas", Brain Res, 1373:183-88 (2011).
Taylor, et al., "MicroRNA signatures of tumor-derived exosomes as diagnostic biomarkers of ovarian cancer", Gynecol. Oncol., 110(1):13-21 (2008).
Thomson, "The biogenesis and function PIWI proteins and piRNAs: progress and prospect", Annu. Rev. Cell Dev Biol., 25:355 (2009).
Vagin, et al., "A distinct small RNA pathway silences selfish genetic elements in the germline", Science, 313(5785):320-24 (2006).
Volinia, et al., "A microRNA expression signature of human solid tumors defines cancer gene targets", PNAS, 103(7):2257-61 (2006).
Wang, et al., "Silencing HIWI suppresses the growth, invasion and migration of glioma cells", Int. J Onco.l, 45(6):2385-92 (2014).
Wang, et al, "The PIWI protein acts as a predictive marker for human gastric cancer", Int J Clin Exp Pathol., 5:315 (2012).
Watanabe, et al., "Retrotransposons and pseudogenes regulate mRNAs and lncRNAs via the piRNA pathway in the germline", Genome Res., 25(3):368-80 (2014).
Watanabe, et a, "Role for piRNAs and noncoding RNA in de novo DNA methylation of the imprinted mouse Rasgrf1 locus", Science, 332:848-52 (2011).
Yang, et al., "Detection of stably expressed piRNAs in human blood", Int. J Clin. Exp. Med., 8(8):13353-8 (2015).
Yin et al., "An epigenetic activation role of Piwi and a Piwi-associated piRNA in Drosophila melanogaster", Nature, 450(7167):304-08 (2007).
Zeng, et al., "HIWI expression profile in cancer cells and its prognostic value for patients with colorectal cancer", Chin Med J (Eng.), 124(14):2144 (2011).
Zhang, et al., "MIWI and piRNA-mediated cleavage of messenger RNAs in mouse testes". Cell Res, 25(2):193-207 (2015).
Zhao, et al., "Novel function of PIWIL1 in neuronal polarization and migration via regulation of microtubule-associated proteins", Mol. Brain., 15:8(1):1-12 (2015).

(56) References Cited

OTHER PUBLICATIONS

Zhao, et al., "HIWI is associated with prognosis in patients with hepatocellular carcinoma after curative resection", *Cancer*, 118(10):2708-17 (2012).
Zuker, "Mfold web server for nucleic acid folding and hybridization prediction", *Nucleic Acids Res.*, 31:3406-15 (2003).
International Search Report dated Aug. 3, 2017 in the corresponding PCT application PCT/US2017/019741.
Genbank accession No. DQ570251, *Homo sapiens* piRNA piR-30363, complete sequence, 1 page, dated Dec. 2, 2008, accessed Feb. 25, 2019.
Genbank accession No. DQ570289, *Homo sapiens* piRNA piR-30401, complete sequence, 1 page, dated Dec. 2, 2008, accessed Feb. 25, 2019.
Genbank accession No. DQ570813, *Homo sapiens* piRNA piR-30925, complete sequence, 1 page 1, dated Dec. 2, 2008, accessed Feb. 25, 2019.
Genbank accession No. DQ570956, *Homo sapiens* piRNA piR-31068, complete sequence, 1 page, dated Dec. 2, 2008, accessed Feb. 25, 2019.
Genbank accession No. DQ572496, *Homo sapiens* piRNA piR-40608, complete sequence, 1 page, dated Dec. 2, 2008, accessed Feb. 25, 2019.
Genbank accession No. DQ572563, *Homo sapiens* piRNA piR-40675, complete sequence, 1 page, dated Dec. 2, 2008, accessed Feb. 25, 2019.
Genbank accessionNo. DQ572799, *Homo sapiens* piRNA piR-40911, complete sequence, 1 page, dated Dec. 2, 2008, accessed Feb. 25, 2019.
Genbank accession No. DQ572958, *Homo sapiens* piRNA piR-41070, complete sequence, 1 page, dated Dec. 2, 2008, accessed Feb. 26, 2019.
Genbank accession No. DQ573174, *Homo sapiens* piRNA piR-41286, complete sequence, 1 page, dated Dec. 2, 2008, accessed Feb. 26, 2019.
Genbank accession No. DQ573435, *Homo sapiens* piRNA piR-41547, complete sequence, 1 page, dated Dec. 2, 2008, accessed Feb. 26, 2019.
Genbank accession No. DQ574652, *Homo sapiens* piRNA piR-42764, complete sequence, 1 page, dated Dec. 2, 2008, accessed Feb. 26, 2019.
Genbank accession No. DQ574941, *Homo sapiens* piRNA piR-43053, complete sequence, 1 page, dated Dec. 2, 2008, accessed Feb. 26, 2019.
Genbank accession No. DQ575393, *Homo sapiens* piRNA piR-43505, complete sequence, 1 page, dated Dec. 2, 2008, accessed Feb. 26, 2019.
Genbank accession No. DQ577802, *Homo sapiens* piRNA piR-45914, complete sequence, 1 page, dated Dec. 2, 2008, accessed Feb. 26, 2019.
Genbank accession No. DQ578027, *Homo sapiens* piRNA piR-46139, complete sequence, 1 page, dated Dec. 2, 2008, accessed Feb. 26, 2019.
Genbank accession No. DQ579124, *Homo sapiens* piRNA piR-47236, complete sequence, 1 page, dated Dec. 2, 2008, accessed Feb. 26, 2019.
Genbank accession No. DQ580941, *Homo sapiens* piRNA piR-49053, complete sequence, 1 page, dated Dec. 2, 2008, accessed Feb. 26, 2019.
Genbank accession No. DQ581429, *Homo sapiens* piRNA piR-49541, complete sequence, 1 page, dated Dec. 2, 2008, accessed Feb. 26, 2019.
Genbank accession No. DQ582530, *Homo sapiens* piRNA piR-32642, complete sequence, 1 page, dated Dec. 2, 2008, accessed Feb. 26, 2019.
Genbank accession No. DQ583503, *Homo sapiens* piRNA piR-50615, complete sequence, 1 page, dated Dec. 2, 2008, accessed Feb. 26, 2019.
Genbank accession No. DQ583881, *Homo sapiens* piRNA piR-50993, complete sequence, 1 page, dated Dec. 2, 2008, accessed Feb. 26, 2019.
Genbank accession No. DQ584010, *Homo sapiens* piRNA piR-51122, complete sequence, 1 page, dated Dec. 2, 2008, accessed Feb. 26, 2019.
Genbank accession No. DQ584878, *Homo sapiens* piRNA piR-51990, complete sequence, 1 page, dated Dec. 2, 2008, accessed Feb. 26, 2019.
Genbank accession No. DQ584921, *Homo sapiens* piRNA piR-52033, complete sequence, 1 page, dated Dec. 2, 2008, accessed Apr. 16, 2019.
Genbank accession No. DQ586335, *Homo sapiens* piRNA piR-53447, complete sequence, 1 page, dated Dec. 2, 2008, accessed Apr. 16, 2019.
Genbank accession No. DQ586508, *Homo sapiens* piRNA piR-53620, complete sequence, 1 page, dated Dec. 2, 2008, accessed Apr. 16, 2019.
Genbank accession No. DQ586669, *Homo sapiens* piRNA piR-53781, complete sequence, 1 page, dated Dec. 2, 2008, accessed Apr. 16, 2019.
Genbank accession No. DQ586872, *Homo sapiens* piRNA piR-53984, complete sequence, 1 page, dated Dec. 2, 20080, accessed Apr. 16, 2019.
Genbank accession No. DQ586910, *Homo sapiens* piRNA piR-54022, complete sequence, 1 page, dated Dec. 2, 2008, accessed Apr. 16, 2019.
Genbank accession No. DQ587013, *Homo sapiens* piRNA piR-54125, complete sequence, 1 page, dated Dec. 2, 2008, accessed Apr. 16, 2019.
Genbank accession No. DQ587366, *Homo sapiens* piRNA piR-54478, complete sequence,1 page, dated Dec. 2, 2008, accessed Apr. 16, 2019.
Genbank accession No. DQ588045, *Homo sapiens* piRNA piR-55157, complete sequence, 1 page, dated Dec. 2, 2008, accessed Apr. 16, 2019.
Genbank accession No. DQ588262, *Homo sapiens* piRNA piR-55374, complete sequence, 1 page, dated Dec. 2, 2008, accessed Apr. 16, 2019.
Genbank accession No. DQ588602, *Homo sapiens* piRNA piR-55714, complete sequence, 1 page, dated Dec. 2, 2008, accessed Apr. 16, 2019.
Genbank accession No. DQ588872, *Homo sapiens* piRNA piR-55984, complete sequence, 1 page, dated Dec. 2, 2008, accessed Apr. 16, 2019.
Genbank accession No. DQ589086, *Homo sapiens* piRNA piR-56198, complete sequence, 1 page, dated Dec. 2, 2008, accessed Apr. 16, 2019.
Genbank accession No. DQ589239, *Homo sapiens* piRNA piR-56351, complete sequence, 1 page, dated Dec. 2, 2008, accessed Apr. 16, 2019.
Genbank accession No. DQ589643, *Homo sapiens* piRNA piR-56755, complete sequence, 1 page, dated Dec. 2, 2008, accessed Apr. 16, 2019.
Genbank accession No. DQ589741, *Homo sapiens* piRNA piR-56853, complete sequence, 1 page, dated Dec. 2, 2008, accessed Apr. 16, 2019.
Genbank accession No. DQ590358, *Homo sapiens* piRNA piR-57470, complete sequence, 1 page, dated Dec. 2, 2008, accessed Apr. 16, 2019.
Genbank accession No. DQ590869, *Homo sapiens* piRNA piR-57981, complete sequence, 1 page, dated Dec. 2, 2008, accessed Apr. 16, 2019.
Genbank accession No. DQ591361, *Homo sapiens* piRNA piR-58473, complete sequence, 1 page, dated Dec. 2, 2008, accessed Apr. 16, 2019.
Genbank accession No. DQ591832, *Homo sapiens* piRNA piR-58944, complete sequence, 1 page, dated Dec. 2, 2008, accessed Apr. 16, 2019.
Genbank accession No. DQ593292, *Homo sapiens* piRNA piR-33404, complete sequence, 1 page, dated Dec. 2, 2008, accessed Apr. 16, 2019.

(56) References Cited

OTHER PUBLICATIONS

Genbank accession No. DQ597805, *Homo sapiens* piRNA piR-35871, complete sequence, 1 page, dated Dec. 2, 2008, accessed Apr. 16, 2019.
Genbank accession No. DQ599147, *Homo sapiens* piRNA piR-37213, complete sequence, 1 page, dated Dec. 2, 2008, accessed Apr. 16, 2019.
Genbank accession No. DQ601367, *Homo sapiens* piRNA piR-39433, complete sequence, 1 page, dated Dec. 2, 2008, accessed Apr. 16, 2019.
Kim, "Small RNAs just got bigger: Piwi-interacting RNAs (piRNAs) in mammalian testes", Genes Dev, 20(15):1993-7 (2006).
Watanabe, et al., "Retrotransposons and pseudogenes regulate mRNAs and lncRNAs via the piRNA pathway in the germline", Genome Res., 25(3):368-80 (2014).
Genbank accession No. DQ586910, *Homo sapiens* piRNA piR-54022, complete sequence, 1 page, dated Dec. 2, 2008, accessed Feb. 26, 2019.
Genbank accession No. DQ587013, *Homo sapiens* piRNA piR-54125, complete sequence, 1 page, dated Dec. 2, 2008, accessed Feb. 26, 2019.
Genbank accession No. DQ587366, *Homo sapiens* piRNA piR-54478, complete sequence, 1 page, dated Dec. 2, 2008, accessed Feb. 26, 2019.

\* cited by examiner

COMPOSITIONS AND METHODS OF USING PIRNAS IN CANCER DIAGNOSTICS AND THERAPEUTICS

CROSS REFERENCE TO RELATED APPLICATIONS

This application is a National Phase application under 35 U.S.C. 371 of PCT/US2017/019741, filed Feb. 27, 2017 entitled "COMPOSITIONS AND METHODS OF USING piRNAS IN CANCER DIAGNOSTICS AND THERAPEUTICS," which claims the benefit of and priority under 35 U.S.C. § 119(e) to U.S. Ser. No. 62/300,748 filed Feb. 26, 2016, and which are incorporated herein by reference in their entirety.

STATEMENT REGARDING FEDERALLY SPONSORED RESEARCH OR DEVELOPMENT

This invention was made with Yale funds and Government Support under Agreement Yale/NCI Research Grant R01 CA154653 awarded by the National Institutes of Health. The Government has certain rights in the invention.

REFERENCE TO SEQUENCE LISTING

The Sequence Listing submitted as a text file named "YU_6901_PCT_ST25.txt," created on Feb. 27, 2017, and having a size of 39,577 bytes is hereby incorporated by reference pursuant to 37 C.F.R. § 1.52(e)(5).

FIELD OF THE INVENTION

The present invention is generally in the field of treating cancer therapeutics and diagnostics.

BACKGROUND OF THE INVENTION

There is an urgent need to develop more effective diagnostic and therapeutic strategies for cancer. For example, conventional therapies, such as chemo- and/or radiotherapy, are often unable to eradicate cancers because of tumor specificities, drug/radiation resistance, and significant side effects.

Given their roles as important regulators of gene expression and genome integrity in cellular development, physiology and pathology, small non-coding RNAs (ncRNAs) have great therapeutic potential for the treatment of cancer. Current translational research of ncRNA-based therapeutics focuses on small interfering RNA (siRNA) and microRNA (miRNA)-based approaches; these are now being tested in clinical trials. Their high efficacy, target-specific action and low toxicity offer significant advantages over the current conventional treatments of cancer. Historically, there are six types of NA-based products: antisense, ribonucleic acid inhibition (RNAi), gene therapy, nucleoside analogs, ribozymes, and aptamers.

PIWI-interacting RNAs (piRNAs) are small (mostly 26-32 nt) noncoding RNAs with highly conserved functions in the protection of germline stem cells from transposable element mobilization. Like microRNAs and small interfering RNAs, piRNAs act as guides in sequence-specific gene regulation in conjunction with Argonaute proteins (PIWI, rather than AGO sub-family proteins, FIG. 1A), yet are far more abundant-over 30,000 piRNAs have been identified in humans, and this number is likely far greater as millions have been identified in other mammalian cells. PIWI-piRNA ribonucleoprotein complexes recruit chromatin-remodeling machinery to complementary genomic targets, where heritable epigenetic modifications are established (via DNA methylation in mammals). Recent studies have also proposed that piRNAs may act post-transcriptionally in mRNA silencing.

Mobile genetic elements such as transposons are a constant threat for the genome. PIWI-interacting RNAs (piRNAs) protect germline cells from transposons in organisms as diverse as flies, fish and mammals. piRNAs are 25 to 33 nt in length, depending on the PIWI clade protein that they bind to. piRNAs derive from distinct transposons that are referred to as piRNA clusters, but the piRNAs from each locus are characterized by a complex mixture of sequences spanning large portions of the transposon. piRNA clusters are transcribed in the sense or antisense direction, and the long single-stranded RNA serves as the basis for piRNA production.

The biogenesis of piRNAs is independent of Dicer and requires other nucleases. Two biogenesis pathways are important for piRNA production. First, a primary processing pathway generates primary piRNAs, and these are then amplified by an amplification cycle referred to as the ping-pong loop. In the primary biogenesis pathway, the long transposon transcript is initially cleaved by the nuclease zucchini (FIGS. 1A and 1B), which probably generates the 5' ends of primary piRNAs.

In the ping-pong cycle (see the lower right panel of FIG. 1B), mature sense primary piRNAs guide PIWI clade proteins to complementary sequences on antisense transcripts from the same piRNA cluster. PIWI proteins use their slicer activity to cleave the target antisense transcript to generate a new 5' end. This 5' end is bound by another PIWI protein. In subsequent steps, the 3' end is trimmed to the length of the mature piRNA, leading to a mature antisense secondary piRNA, which can now target sense transcripts transcribed from the piRNA cluster. In *Drosophila melanogaster*, the two PIWI proteins Aubergine and Ago3 cooperate in secondary piRNA production to generate sense and antisense piRNAs. However, antisense piRNAs dominate, and a protein called Qin, which contains E3 ligase and Tudor domains, seems to modulate such a heterotypic ping-pong cycle. In the mouse germ line, the PIWI proteins MILI and MIWI collaborate in piRNA generation. After trimming, piRNAs receive a methyl group at the 3' end by the methyltransferase HEN1. Primary piRNAs carry such modifications as well.

piRNAs guide PIWI proteins to complementary RNAs derived from transposable elements. Similar to RNA interference, PIWI proteins cleave the transposon RNA, leading to silencing. In flies, mutations in piwi, aub and Ago3 (which encode the PIWI proteins in *D. melanogaster*) are required for transposon silencing in the germ line. Similar observations were made when the mouse PIWI proteins MILI and MIWI were genetically inactivated. Here, long interspersed nuclear elements (LINE) and long terminal repeat (LTR) retrotransposons accumulated.

Despite the longstanding notion that activity of the PIWI-piRNA pathway is restricted to the germline, evidence is quickly mounting for roles in somatic tissues, particularly in the context of cancer. Aberrant PIWI-family protein expression has been associated with unfavorable prognosis in eleven cancer types, and piRNA expression has been observed in fourteen cancer types. In the most comprehensive study of piRNA expression outside of the germline to date, Martinez et al. utilized RNA-seq data from The Cancer Genome Atlas to demonstrate that hundreds of piRNAs are expressed in both normal and malignant tissues from each of eleven anatomical sites (bladder, breast, colon, head/neck, kidney, lung, ovaries, prostate, stomach, thyroid, and uterus), and that piRNA expression programs are dysregulated in a clinically relevant, tumor type-specific manner.

Studies show that aberrant piRNA expression can be a signature feature of a cancer. However, over 20,000 piRNA genes in the human genome and irregular piRNA expression appears to be cancer type specific. Thus, there remains a need to identify the piRNA's whose aberrant expression correlates with a particular cancer's frequency and/or severity, and design therapeutic measure based thereon.

Thus, it is an object of the invention to provide specific piRNAs thereof that are genetically associated or are aberrantly expressed in specific cancer types including glioblastoma, liver, prostate, lung, and breast.

It is another object of the invention to provide therapeutic agents and methods of use thereof to correct or compensate for aberrant piRNA expression in a subject in need thereof.

It is another object of the invention to provide methods of diagnosing a subject or predicting the severity of the subject's disease.

It is another object of the invention to provide methods of determining the efficacy of a therapeutic intervention.

It is another object of the invention to provide methods of screening for new aberrant piRNA.

SUMMARY OF THE INVENTION

Aberrantly expressed piRNA are disclosed. Aberrant expression of piRNA can correlate with cancer prevalence and prognosis. In some instances, one or more wildtype piRNAs can be decreased in cancer tissue relative to normal or control tissue. In such instances the wildtype piRNA or a close variant thereof with the same or similar activity to wildtype, or a stimulator of expression thereof, can be administered to a subject in need thereof in an effective amount to increase the expression of the target piRNA and treat or prevent the cancer. Additionally, or alternatively, one or more wildtype piRNAs can be increased in cancer tissue relative to normal or control tissue. In such instances an inhibitor of the piRNA can be administered to a subject in need thereof in an effective amount to reduce the expression of the target piRNA and treat or prevent the cancer.

Additionally, it has been discovered that genomic sequences encoding piRNA can contain one or more mutations relative to wildtype (e.g., polymorphisms, such as single nucleotide polymorphisms), and such mutations can be associated with cancer prevalence and prognosis. Typically, wildtype piRNA or a close variant thereof with the same or similar activity to wildtype, or a stimulator of expression thereof, can be administered to a subject in need thereof in an effective amount to increase the expression of the target piRNA and treat or prevent the cancer.

Detection of aberrantly expressed piRNA and their association with cancer risk and severity can be used as both a biomarker of cancer, and to develop treatment strategies for treating the cancer. Thus, compositions and methods of using piRNA for treating cancer are provided. Methods of diagnosing subjects and determining the efficacy of active agents for treating cancer are also provided. Methods of correlating variant piRNA to cancer are also disclosed.

BRIEF DESCRIPTION OF THE DRAWINGS

FIG. 3A is an illustration of the predicted secondary structure of piR-598 and location of rs147061479 (SEQ ID NO:48). The illustration was adapted from prediction by the Mfold v.3.6 RNA folding algorithm. Paired bases are denoted by connecting lines. FIG. 3B is a Venn diagram showing that transcripts affected by overexpression of piR-598 mimics in U87 were enriched for those with roles in the indicated molecular functions according to Ingenuity Pathway Analysis. P-values were generated using a Fisher's exact test for enrichment of affected genes according to functional annotation. FIG. 3C is a network visualization illustrating functional interrelatedness of differentially expressed transcripts related to cell death and cell cycle progression following piR-598 treatment of U87 cells. Shading denote piR-598-induced transcript over-expression (noted with "*") and under-expression (noted with "#") relative to negative control, respectively, with color intensity corresponding to degree of change; solid lines and dotted lines indicate direct and indirect relationships, respectively.

FIGS. 4A-4C show the viability relative to control after approximately $2.5\times10^3$ U87 (4A), A172 (4B) or NHA (4C) cells were transfected with 25 nM piR-598-WT or piR-598-V mimics or a control RNA oligo in 96-well plates with 6 replicates per condition. Cell viability was quantified using MTS at 48 and 96 hours after transfection. FIG. 4D show the number of colonies formed after approximately $1\times10^4$ cells were transfected with indicated oligos and seeded in triplicate 24 hours later in soft agar in a single cell suspension. Colonies were counted using ImageJ three weeks after seeding. NC: Negative control; NHA: normal human astrocytes. *, $P<0.05$; , $P<0.01$; *, $P<0.001$; error bars denote standard deviation of replicate experiments.

FIG. 6A shows U87 cell proliferation following transfection of piRNAs underexpressed in tumor relative to normal brain tissue (fold-changes noted in figure legend) or piRNAs equivalently expressed in tumor and normal brain tissue (no association). Values denote ratio of color development after MTS exposure of piRNA-treated cells relative to negative control (NC)-treated cells; dotted line represents equivalent cell viability after piRNA or negative control RNA exposure. Statistical significance was assessed by comparing piRNA- and NC-treated cell viability at each time point. FIG. 6B shows NHA, A172, and U87 cell proliferation following piR-8041 upregulation. Values denote relative viability of piR-8041 vs. NC-treated cells and statistical significance was assessed by the deviation from NC treatment, denoted by the dotted line. FIG. 6C shows U87 colonies formed in soft agar 21 days after piR-8041 or NC transfection. Colonies were counted using ImageJ software. FIG. 6D shows U87 cell viability at six days following one (day 0 only) or two (day 0 and day 3) piR-8041 treatments. NS, not significant; *, P<0.05; , P<0.01; *, P<0.001; error bars denote standard deviation of triplicate experiments for all figures.

FIG. 7A is a bar graph showing cell cycle distribution 48 hours post-piR-8041 or NC-treatment. Cell cycle phases were determined by flow cytometric analysis of DNA content by staining with propidium iodide; proportions were determined using FlowJo software by the Dean-Jett-Fox cell cycle modeling algorithm. FIG. 7B is a bar graph showing proportions of U87 cells in early or late apoptosis/necrosis 48 hours post-piR-8041 or NC-treatment as determined by flow cytometric analysis of Annexin V and PI staining. Early apoptotic cells were defined as those stained with Annexin V but excluding PI, late apoptotic/necrotic were cells stained with both probes. NS, not significant *, P<0.05; **, P<0.01; error bars denote standard deviation of triplicate experiments.

FIG. 11A is a line graph showing cellular growth impact measured by Cell Proliferation Assay (MTS) in Hep3B liver tumor cells and THLE-3 normal liver cells after piR-37213 mimic transfection. Error bars represent standard error. FIG. 11B is a bar graph showing experimental results 2-weeks post-transfection with control small RNA (left bar) or piR-37213 (right bar) into Hep3B cells. The number of colonies in piR-37213 transfected Hep3B plates were reduced by approximately 70% relative to the number of colonies formed in control oligo treated plates (FIG. 2B, P<0.01).

DETAILED DESCRIPTION OF THE INVENTION

I. Definitions

Figure 1A:
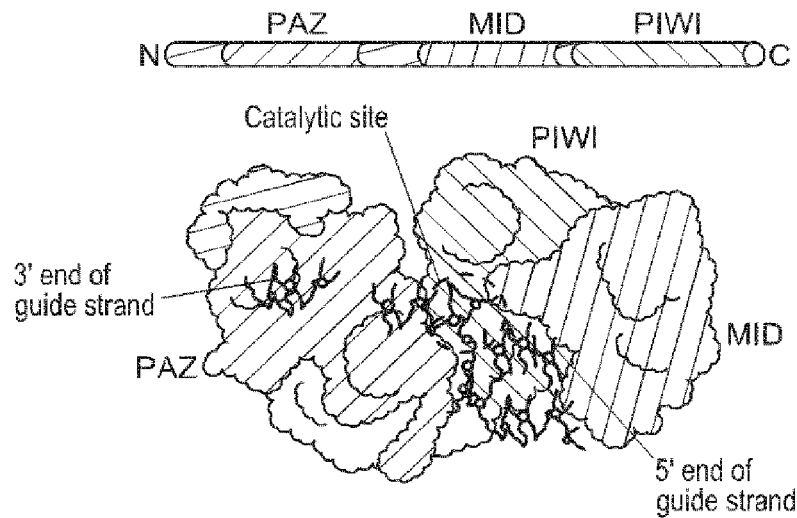
FIG. 1A is a schematic from Kim, et al., *Nat. Rev. Mol. Cell Biol.*, 10(2): 126-39 2009, depicting small RNAs classified into three classes based on their biogenesis mechanism and the type of Argonaute protein that they are associated with: microRNAs (miRNAs), endogenous small interfering RNAs (endo-siRNAs or esiRNAs) and PIWI-interacting RNAs (piRNAs). piRNAs are small RNAs of 20-30 nucleotides that can target both chromatin and transcripts, and thereby keep both the genome and the transcriptome under extensive surveillance.
Figure 1B:
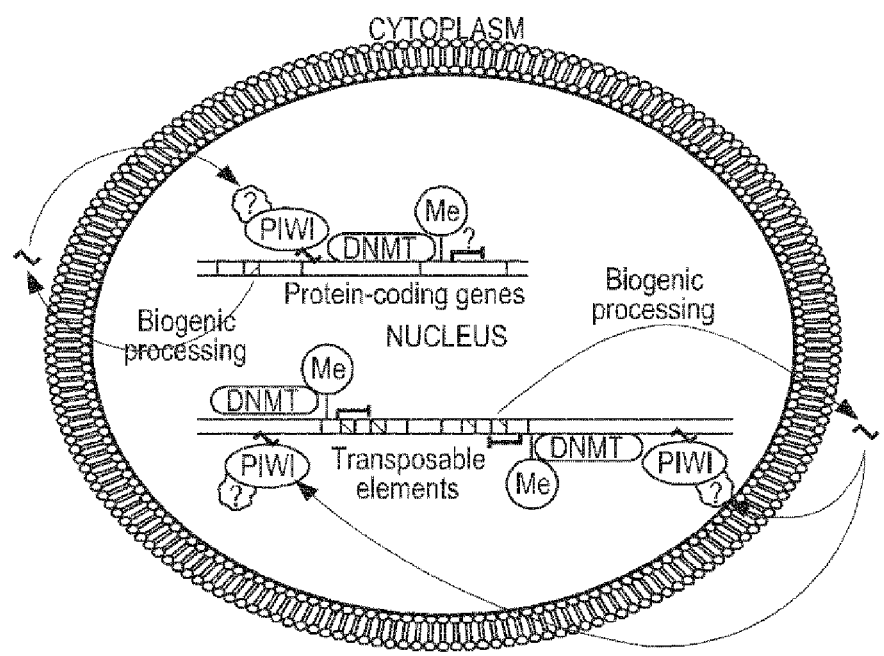
FIG. 1B is schematic showing the function of piRNA in somatic cells, with roles in somatic epigenetic programming, stem cell function and memory (Ross, et al., *Nature,* 505, 353-359, 2014), with several hundred piRNAs being expressed in normal somatic tissues of each of 10 organ sites in a tissue-specific manner (Martinez. et al. *Sci. Rep.* 5, Article number 10423, 2015), and regulation of non-transposon protein-coding genes (Fu, Jacobs and Zhu, *RNA Biol.,* 11(10):1301-12, 2014).

As used herein, the term "carrier" or "excipient" refers to an organic or inorganic ingredient, natural or synthetic inactive ingredient in a formulation, with which one or more active ingredients are combined.

As used herein, the term "pharmaceutically acceptable" means a non-toxic material that does not interfere with the effectiveness of the biological activity of the active ingredients.

As used herein, the terms "effective amount" or "therapeutically effective amount" means a dosage sufficient to alleviate one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the disease or disorder being treated, as well as the route of administration and the pharmacokinetics of the agent being administered.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

As used herein, a "vector" is a replicon, such as a plasmid, phage, or cosmid, into which another DNA segment may be inserted so as to bring about the replication of the inserted segment. The vectors described herein can be expression vectors.

As used herein, an "expression vector" is a vector that includes one or more expression control sequences.

As used herein, an "expression control sequence" is a DNA sequence that controls and regulates the transcription and/or translation of another DNA sequence.

As used herein, the term "host cell" refers to prokaryotic and eukaryotic cells into which a recombinant nucleotide, such as a vector, can be introduced.

As used herein, "transformed" and "transfected" encompass the introduction of a nucleic acid (e.g. a vector) into a cell by a number of techniques known in the art.

As used herein, the term "polypeptide" refers to a chain of amino acids of any length, regardless of modification (e.g., phosphorylation or glycosylation). The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein "variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various foregoing characteristics into consideration are well known to those of skill in the art and include (original residue: exemplary substitution): (Ala: Gly, Ser), (Arg: Lys), (Asn: Gin, His), (Asp: Glu, Cys, Ser), (Gln: Asn), (Glu: Asp), (Gly: Ala), (His: Asn, Gin), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

The term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence C to, with, or against a given nucleic acid sequence D (which can alternatively be phrased as a given sequence C that has or comprises a certain % sequence identity to, with, or against a given sequence D) is calculated as follows:

100 times the fraction W/Z, where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

As used herein, the term "operably linked" refers to a juxtaposition wherein the components are configured so as to perform their usual function. For example, control sequences or promoters operably linked to a coding sequence are capable of effecting the expression of the coding sequence, and an organelle localization sequence operably linked to protein will direct the linked protein to be localized at the specific organelle.

As used herein, the terms "individual," "individual," "subject," and "patient" are used interchangeably herein, and refer to a mammal, including, but not limited to, humans, rodents, such as mice and rats, and other laboratory animals.

As used herein, the term "wildtype" generally means a strain, gene, or characteristic that prevails among individuals in natural conditions, as distinct from an atypical mutant type.

As used herein, the term "mutant" generally means a strain, gene, or characteristic that diverges from wildtype.

II. Aberrantly Expressed piRNAs and Genetically Associated piRNAs

Aberrantly expressed piRNA are disclosed. Although specific preferred embodiments having the greatest difference in expression or highest correlation with cancer are discussed in detail, it will be appreciated that other embodiments discussed in the experiments and charts provided in the working examples below can also be used. Different piRNAs are expressed in different tissues, and increased, decreased, or mutant expression thereof is typically specific for the cancer type or types in which the aberrant expression is discovered.

Aberrant expression of piRNA can correlate with cancer prevalence and prognosis. In some instances, one or more wildtype piRNAs can be decreased in cancer tissue relative to normal or control tissue. For example, if one or more of the downstream targets of the piRNA is an oncogene or other tumorigenic gene, reduced expression of the piRNA could result in increased expression of the oncogene or other tumorigenic gene and lead to cancer. In such instances the wildtype piRNA or a close variant thereof with the same or similar activity to wildtype, or a stimulator of expression thereof, can be administered to a subject in need thereof in an effective amount to increase the expression of the candidate piRNA, reduce expression of a target oncogene thereof, and treat or prevent the cancer.

Additionally, or alternatively, one or more wildtype piRNAs can be increased in cancer tissue relative to normal or control tissue. For example, if one or more of the downstream targets of the piRNA is tumor suppressor, increased expression of the piRNA could result in decreased expression of the tumor suppressor and lead to cancer. In such instances an inhibitor of the piRNA, can be administered to a subject in need thereof in an effective amount to reduce the expression of the target piRNA, increase expression of a target tumor suppressor gene thereof, and treat or prevent the cancer.

Additionally, it has been discovered that genomic sequences encoding piRNA can contain one or more mutations relative to wildtype (e.g., polymorphisms, such as single nucleotide polymorphisms: SNPs), and such mutations can be associated with cancer prevalence and prognosis. Such aberrantly expressed piRNA can also be referred to as genetically associated piRNAs. Mutations can cause the piRNA to behave as if wildtype expression is decreased, even if the mutant piRNA is expressed at normal levels. For example, if the mutation reduces the ability of the piRNA to interact with its target gene, the mutant piRNA could result in increased expression of the oncogene or other tumorigenic gene and lead to cancer if the wildtype piRNA typically target that oncogene or other tumorigenic gene. In such instances the wildtype piRNA or a close variant thereof with the same or similar activity to wildtype, or a stimulator of expression thereof, can be administered to a subject in need thereof in an effective amount to increase the expression of the target piRNA, reduce expression of a target oncogene thereof, and treat or prevent the cancer. Mutations relative to wildtype may also provide a protective effect from developing cancer (i.e., cancer prevalence or severity etc., is reduce when the subject has a polymorphism).

Other ways that the piRNA may directly or indirectly contribute to tumorigenesis include, but are not limited to, (1) aberrant DNA methylation resulting in genomic silencing and promotion of a "stem-like" state, (2) inducing euchromatin state by altering histone modifications, and (3) dysregulating the cell cycle; which can occur independent its of role in regulating target mRNA expression. Similar to other embodiments in which the piRNA is acting indirectly as a tumor suppressor, the wildtype piRNA or a close variant thereof with the same or similar activity to wildtype, or a stimulator of expression thereof, can be administered to a subject in need thereof in an effective amount to increase the expression of the target piRNA and treat or prevent the cancer.

Thus, detection of aberrantly expressed piRNA and their association with cancer risk and severity can be used as both a biomarker of cancer, and to develop treatment strategies for treating the cancer.

As discussed herein, "normal tissue" most typically means noncancerous tissue or cells, and is most typically the same or similar tissue or cells to the cancerous tissue or cells to which it is being compared.

A. Brain Cancer

1. Single Nucleotide Polymorphisms

Figure 2A:
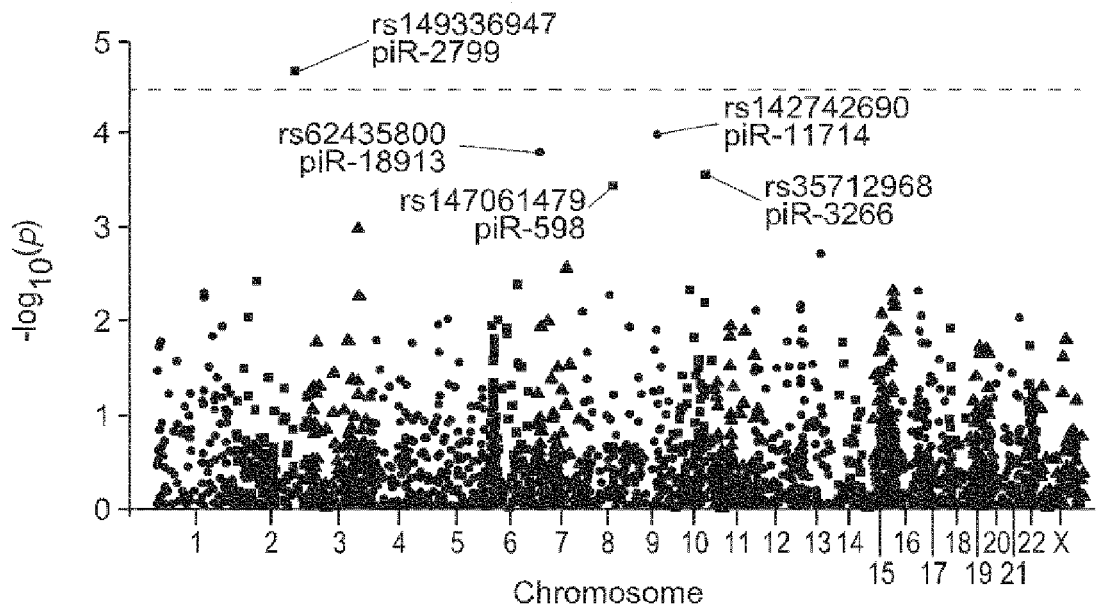
FIG. 2A is a Manhattan plot showing the results of association analyses of piRNA variants and glioma. Five SNPs demonstrating statistically significant or suggestive associations with glioma risk are labeled: piR-2799, piR-18913, piR-598, piR-11714, and piR-3266; dotted line represents the Bonferroni-adjusted significance threshold, $P=3.50\times10^{-5}$. piRNA SNPs are plotted according to physical genomic order on the x-axis.
Figure 2B:
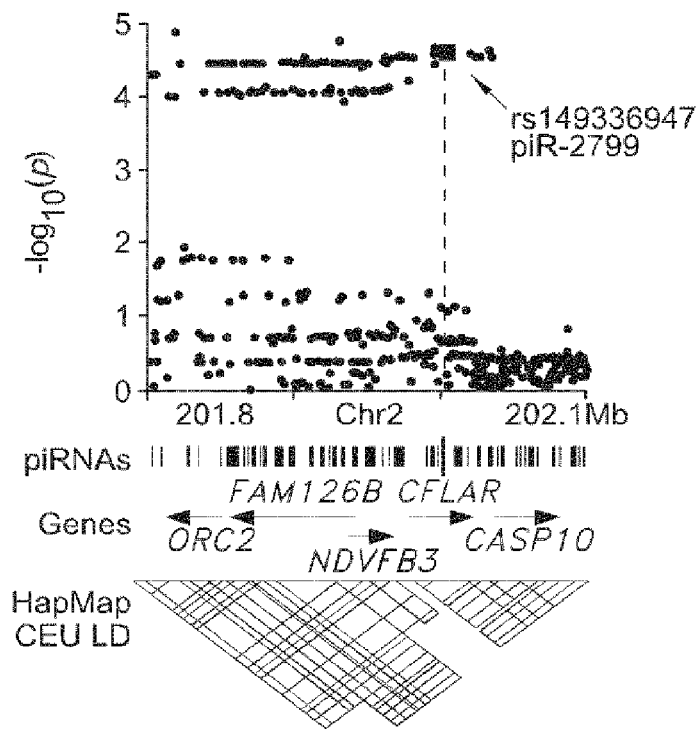
FIG. 2B-2F are plots showing the regional imputation of all 1,000 Genomes SNPs with MAF>1% in piR-2799, piR-18913, piR-598, piR-11714, and piR-3266 regions. Association results are presented in context of piRNAs from piRNABank, known protein-coding genes, and linkage disequilibrium (LD) patterns from the HapMap CEU population.
Figure 2C:
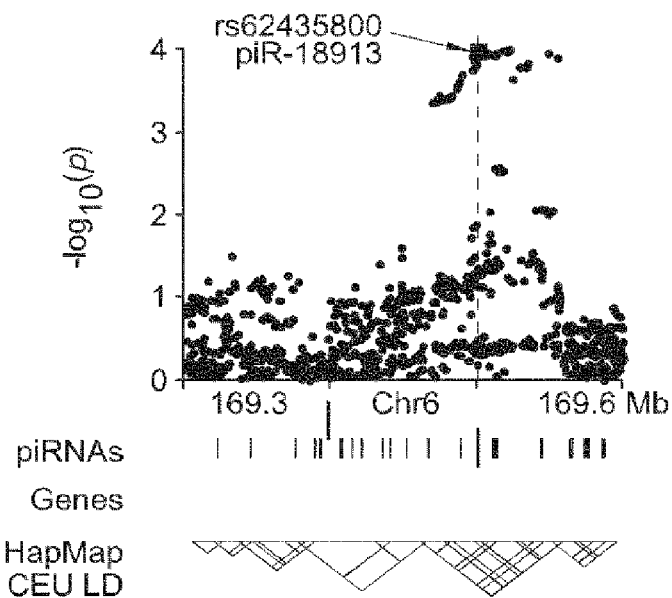
Figure 2D:
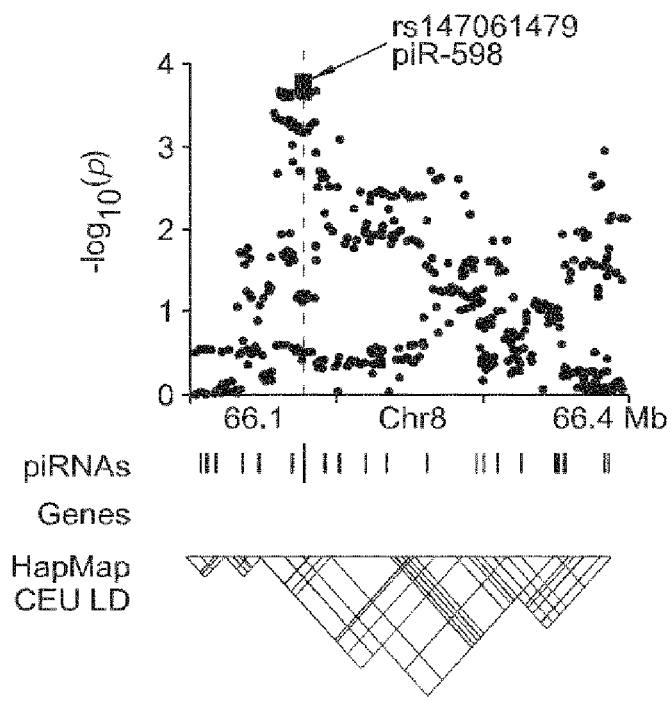
Figure 2E:
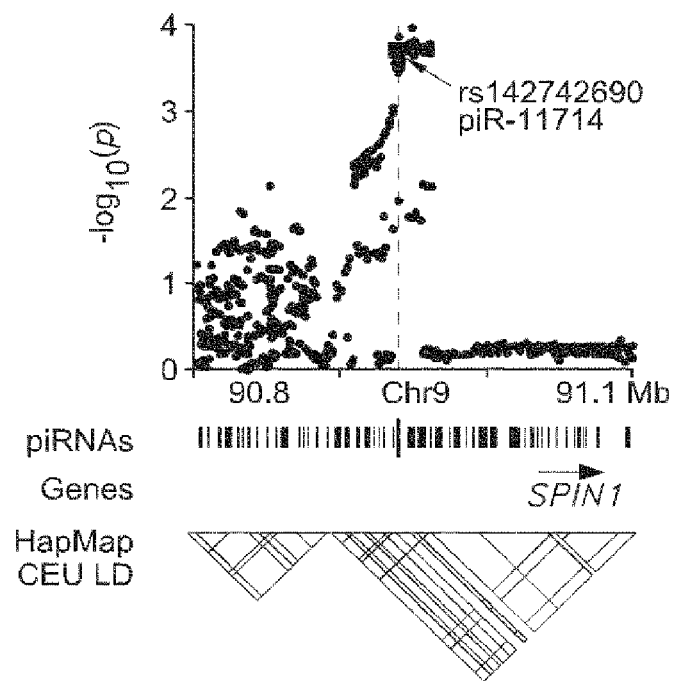
Figure 2F:
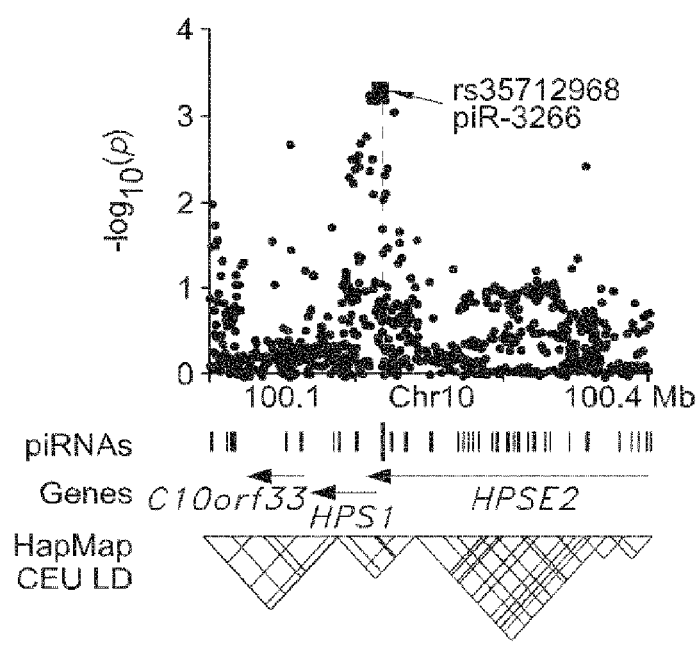

The piRNAs listed in Table 1 are the top piRNA SNPs associated with glioma risk identified in a post-GWAS (Genome-wide association study) analysis discussed in more detail in the Examples below. Analysis revealed a Bonferroni-corrected ($P<0.05/1,428$ SNPs=$3.50\times10^{-5}$) statistically significant association between glioma risk and rare variant rs149336947 ($P=2.34\times10^{-5}$; FDR-adjusted $P=0.033$), located near the 3' end of piR-2799 on chromosome 2q33.1. piR-2799 is a 30 nucleotide piRNA that maps to the fourth intron of apoptosis inhibitor CFLAR, which is widely expressed in the human body including in the brain (FIG. 2A). Four additional modest associations of interest were observed at rs62435800 in piR-18913 on chromosome 6q27 ($P=1.13\times10^{-4}$; FDR-adjusted $P=0.054$), rs147061479 in piR-598 on chromosome 8q13.1 ($P=1.69\times10^{-4}$; FDR-adjusted $P=0.060$), rs142742690 in piR-11714 on chromosome 9q22.1 ($P=1.10\times10^{-4}$; FDR-adjusted $P=0.079$), and rs35712968 in piR-3266 on chromosome 10q24.2 ($P=3.11\times10^{-4}$; FDR-adjusted $P=0.089$) (Table 1).

Thus, wildtype piR-2799, piR-18913, piR-598, piR-11714, piR-3266 or a close variant thereof with the same or similar activity to wildtype, or a stimulator of expression thereof, can be administered to a subject in need thereof in an effective amount to increase the expression of the the piRNA and treat or prevent a brain cancer such as glioma. The subject can have one or more mutations in one or more chromosomal copies of the piRNA that reduces an activity of the piRNA. For example, wildtype piR-2799 can be administered to subjects having at least one rs149336947 SNP, wildtype piR-18913 can be administered to subjects having at least one rs62435800 SNP, wildtype piR-598 can be administered to subjects having at least one rs147061479 SNP, wildtype piR-11714 can be administered to subjects having at least one rs142742690 SNP, wildtype piR-3266 can be administered to subjects having at least one rs35712968 SNP, etc.

2. Dysregulated Expression

Figure 5A:
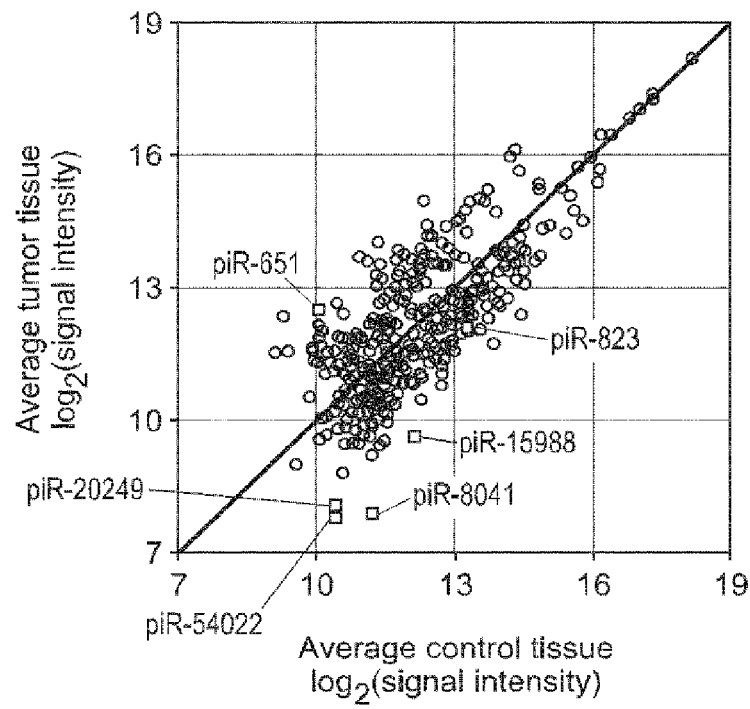
FIG. 5A is a plot showing the results of array-based piRNA expression profiling and confirmation of piR-8041 underexpression in glioblastoma multiforme (GBM) relative to normal pooled brain specimens (average tumor tissue signal intensity versus average control tissue signal sensitivity). piRNAs with detectable expression levels are plotted according to average log 2(signal intensity) in each tissue type. piR-8041 and other notable piRNAs (piR-54022, piR-20249, piR-15988, piR-823, piR-651) some of which were examined in subsequent cell proliferation analyses are labeled.

As discussed in the Examples below, following array-based piRNA profiling, 353 piRNAs were observed to be expressed in both normal and tumor tissue (FIG. 5A). Expression differences of at least two-fold between comparison groups were observed for 145 piRNAs (Table 3 below). Any of the piRNAs in Table 3 can be utilized in the diagnostic and treatment strategies discussed herein. For example, piR-8041, piR-54022, piR-20249, and piR-15988 are all underexpressed in cancer relative to normal tissue. Thus, wildtype piR-8041, piR-54022, piR-20249, and/or piR-15988, or close variants thereof with the same or similar activity to wildtype, or a stimulator of expression thereof, can be administered to a subject in need thereof in an effective amount to increase the expression of the piRNA and treat or prevent the cancer. In some embodiments, the subject being treated has a cancer characterized by reduced expression of piR-8041, piR-54022, piR-20249, and/or piR-15988.

3. Cancers to Diagnose and Treat

The compositions and methods can be applied to benign and malignant brain tumors and cancers. Brain tumors include all tumors inside the cranium or in the central spinal canal. They are created by an abnormal and uncontrolled cell division, normally either in the brain itself (neurons, glial cells (astrocytes, oligodendrocytes, ependymal cells, myelin-producing Schwann cells, lymphatic tissue, blood vessels), in the cranial nerves, in the brain envelopes (meninges), skull, pituitary and pineal gland, or spread from cancers primarily located in other organs (metastatic tumors). Examples of brain tumors include, but are not limited to, glioblastoma, oligodendroglioma, meningioma, supratentorial ependymona, pineal region tumors, medulloblastoma, cerebellar astrocytoma, infratentorial ependymona, brainstem glioma, schwannomas, pituitary tumors, craniopharyngioma, optic glioma, and astrocytoma.

"Primary" brain tumors originate in the brain and "secondary" (metastatic) brain tumors originate from cancer cells that have migrated from other parts of the body. Primary brain cancer rarely spreads beyond the central nervous system, and death results from uncontrolled tumor growth within the limited space of the skull. Metastatic brain cancer indicates advanced disease and has a poor prognosis. Primary brain tumors can be cancerous or noncancerous. Both types take up space in the brain and may cause serious symptoms (e.g., vision or hearing loss) and complications (e.g., stroke). All cancerous brain tumors are life threatening (malignant) because they have an aggressive and invasive nature. A noncancerous primary brain tumor is life threatening when it compromises vital structures (e.g., an artery). In a particular embodiment, the disclosed compositions and methods are used to treat cancer cells or tumors that have metastasized from outside the brain (e.g., lung, breast, melanoma) and migrated into the brain.

B. Liver Cancer
1. Dysregulated Expression

As discussed in more detail in the Examples below, a piRNA expression profiling analysis, 12 pairs of HCC and matching non-malignant liver specimens were compared using an ArrayStar piRNA expression microarray covering 23,000 human piRNAs. 31 piRNA of interest were identified. Any of the piRNAs can be utilized in the diagnostic and treatment strategies discussed herein. Of particular interest were three piRNAs piR-37213, piR-17656, and piR-33404 that were ≥3-fold statistically significantly differentially expressed.

piR-37213 was underexpressed in tumor tissue relative to normal tissue. Thus, wildtype piR-37213, or close variants thereof with the same or similar activity to wildtype, or a stimulator of expression thereof, can be administered to a subject in need thereof in an effective amount to increase the expression of the piRNA and treat or prevent the cancer. In some embodiments, the subject being treated has a cancer characterized by reduced expression of piR-37213.

piR-17656 and piR-33404 were overexpressed in tumor tissue relative to normal tissue. Thus, an inhibitor of wildtype piR-17656 and/or piR-33404 can be administered to a subject in need thereof in an effective amount to reduce the expression of the piRNA and treat or prevent the cancer. In some embodiments, the subject being treated has a cancer characterized by increased expression of piR-17656 and/or piR-33404.

2. Cancers to Diagnose and Treat

The compositions and methods can be applied to benign and malignant liver tumors and cancers. Benign liver growths include haemangioma, hepatic adenoma, and focal nodular hyperplasia. Liver cancer can include, for example, hepatocellular carcinoma (HCC), also sometimes called hepatoma or HCC, fibrolamellar carcinoma, cholangiocarcinoma (bile duct cancer), angiosarcoma, and hepatoblastoma. Common secondary liver cancers originate from breast cancer, bowel cancer, or lung cancer. In particularly preferred embodiments, the subject has hepatocellular carcinoma.

C. Prostate Cancer
1. Single Nucleotide Polymorphisms

The Examples discussed in more detail below include association analyses carried out for 1847 variants to identify piRNA mutations associated with prostate cancer. The variant rs61101785, located in piR-021163, was associated with an increased risk of prostate cancer. Other top hits are listed in Table 4 (below). Thus, wildtype piR-021163, piR-003123, piR-008061, piR-013783, piR-14246, piR-008286, piR-018495 or close variants thereof with the same or similar activity to wildtype, or a stimulator of expression thereof, can be administered to a subject in need thereof in an effective amount to increase the expression of the piRNA and treat or prevent prostate cancer. The subject can have one or more mutations in one or more chromosomal copies of the piRNA that reduces an activity of the piRNA. For example, wildtype piR-021163 can be administered to subjects having at least one rs61101785 SNP, wildtype piR-003123 can be administered to subjects having at least one rs62439721 SNP, wildtype piR-008061 can be administered to subjects having at least one rs11074184 SNP, wildtype piR-013783 and/or piR-14246 can be administered to subjects having at least one rs8010969 SNP, wildtype piR-008286 can be administered to subjects having at least one rs008286 SNP, wildtype piR-018495 can be administered to subjects having at least one rs8020378 SNP, etc.

In preferred embodiments, wildtype piR-021163 or a close variant thereof with the same or similar activity to wildtype, or a stimulator of expression thereof, can be administered to a subject in need thereof in an effective amount to increase the expression of the piRNA and treat or prevent a prostate cancer. In some embodiments, the subject has at least one rs61101785 SNP.

2. Cancers to Diagnose and Treat

The compositions and methods can be applied to benign and malignant prostate tumors and cancers. The precursor to prostate cancer is known as prostatic intraepithelial neoplasia. Prostate cancers include, for example, benign prostatic hyperplasia (BPH), prostatic adenocarcinoma, small cell carcinoma, squamous cell carcinoma, prostatic sarcomas, and transitional cell carcinomas.

D. Lung Cancer
1. Single Nucleotide Polymorphisms

The Examples discussed in more detail below include post-GWAS study combining the association results, expression profiling results, and the functional analysis results exploring the association between piRNAs variants and lung cancer risk. The top hits are presented in Table 4 (below), and include rs13382748 in piR-21626, rs60534722 in piR-16828. A variant in one SNP (rs11639347) was identified that is significantly associated with the increase risk of lung cancer. The location of the variant (Chromosome 15: 79024350) and the 2 piRNAs, piR-5247 (Chromosome 15: 79024333-79024361) and piR-5671 (Chromosome 15: 79024327-79024355) is in intergenic region. This indicates that the functional changes caused by the 2 piRNAs may be attributed to the function of themselves.

Thus, wildtype piR-21626, piR-16828, piR-5247, piR-5671 or close variants thereof with the same or similar activity to wildtype, or a stimulator of expression thereof, can be administered to a subject in need thereof in an effective amount to increase the expression of the piRNA and treat or prevent lung cancer. The subject can have one or more mutations in one or more chromosomal copies of the piRNA that reduces an activity of the piRNA. For example, wildtype piR-21626 can be administered to subjects having at least one rs13382748 SNP, wildtype piR-16828 can be administered to subjects having at least one rs60534722 SNP, wildtype piR-5247 and/or piR-5671 can be administered to subjects having at least one rs11639347 SNP, etc.

In particularly preferred embodiments, wildtype piR-5247 and/or piR-5671 or close variants thereof with the same or similar activity to wildtype, or a stimulator of expression thereof, can be administered to a subject in need thereof in an effective amount to increase the expression of the piRNA and treat or prevent lung cancer, more preferably in a subject having at least one rs11639347 SNP.

2. Dysregulated Expression

The Examples also describe in more detail an expression analysis identifying 7 top hits (see Table 5), including piR-14620, piR-20009, piR-31637, piR-2732, piR-51809, piR-19521, and piR-15232, wherein 5 piRNA: piR-14620, piR-2732, piR-51809, piR-19521, and piR-15232, were the most statistically significant. Any of the piRNAs in Table 5 can be utilized in the diagnostic and treatment strategies discussed herein. For example, piR-14620, piR-20009, piR-2732, piR-51809, piR-19521, and piR-15232 were all overexpressed in tumor tissue relative to normal tissue. Thus, an inhibitor of wildtype piR-14620, piR-20009, piR-2732, piR-51809, piR-19521, and/or piR-15232 can be administered to a subject in need thereof in an effective amount to reduce the expression of the piRNA and treat or prevent the cancer. In some embodiments, the subject being treated has a cancer characterized by increased expression of piR-14620, piR-20009, piR-2732, piR-51809, piR-19521, and/or piR-15232.

piR-31637 was underexpressed in tumor tissue relative to normal tissue. Thus, wildtype piR-31637, or close variants thereof with the same or similar activity to wildtype, or a stimulator of expression thereof, can be administered to a subject in need thereof in an effective amount to increase the expression of the piRNA and treat or prevent the cancer. In some embodiments, the subject being treated has a cancer characterized by reduced expression of piR-31637.

3. Cancers to Diagnose and Treat

The compositions and methods can be applied to benign and malignant lung tumors and cancers. Lung cancers include, for example, non-small cell lung cancer (NSCLC) such as adenocarcinoma, adenocarcinoma in situ, squamous cell carcinoma, large cell carcinoma, and large cell neuroendocrine tumors, small cell lung cancer (SCLC), mesothelioma, and carcinoid tumors.

E. Breast Cancer

1. Single Nucleotide Polymorphisms

The Examples discussed in more detail below include association analyses that identified four SNPs harbored in piRNAs that are associated with breast cancer risk. The top SNP identified, rs28649125 in piR-17319, is of particular interest owing to the high MAF of the protective variant allele and the corresponding population attributable risk of 7.8%. Other top hits are listed in Table 7 (below). Thus, wildtype piR-17319, piR-9422, piR-16556, and piR-3467 or close variants thereof with the same or similar activity to wildtype, or a stimulator of expression thereof, can be administered to a subject in need thereof in an effective amount to increase the expression of the piRNA and treat or prevent prostate cancer. The subject can have one or more mutations in one or more chromosomal copies of the piRNA that reduces an activity of the piRNA. For example, wildtype piR-17319 can be administered to subjects having at least one rs28649125 SNP, wildtype piR-9422 can be administered to subjects having at least one rs11914017 SNP, wildtype piR-16556 can be administered to subjects having at least one rs10518263 SNP, wildtype piR-3467 can be administered to subjects having at least one rs72755158 SNP, etc.

In preferred embodiments, wildtype piR-17319 or a close variant thereof with the same or similar activity to wildtype, or a stimulator of expression thereof, can be administered to a subject in need thereof in an effective amount to increase the expression of the piRNA and treat or prevent a breast cancer. In some embodiments, the subject has at least one rs28649125 SNP.

2. Dysregulated Expression

The Examples also describe in more detail an expression analysis identifying 15 top hits (see Table 10), including piR_016975, piR_019169, piR_018292, piR_017178, piR_019368, piR_019911, piR_000560, piR_001207, piR_012753, piR_003728, piR_001078, and piR_012925, each of which has reduced expression in tumor cells relative to normal cells; and piR_020582 and piR_004987 each of which has increased expression in tumor cells relative to normal cells.

Any of the piRNAs in Table 10 can be utilized in the diagnostic and treatment strategies discussed herein. For example, piR_016975, piR_019169, piR_018292, piR_017178, piR_019368, piR_019911, piR_000560, piR_001207, piR_012753, piR_003728, piR_001078, and piR_012925 were all underexpressed in tumor tissue relative to normal tissue. Thus, wildtype piR_016975, piR_019169, piR_018292, piR_017178, piR_019368, piR_019911, piR_000560, piR_001207, piR_012753, piR_003728, piR_001078, and/or piR_012925, or close variants thereof with the same or similar activity to wildtype, or a stimulator of expression thereof, can be administered to a subject in need thereof in an effective amount to increase the expression of the piRNA and treat or prevent the cancer. In some embodiments, the subject being treated has a cancer characterized by reduced expression of piR_016975, piR_019169, piR_018292, piR_017178, piR_019368, piR_019911, piR_000560, piR_001207, piR_012753, piR_003728, piR_001078, and/or piR_012925.

piR_020582 and piR_004987 were all overexpressed in tumor tissue relative to normal tissue. Thus, an inhibitor of wildtype piR_020582 and/or piR_004987 can be administered to a subject in need thereof in an effective amount to reduce the expression of the piRNA and treat or prevent the cancer. In some embodiments, the subject being treated has a cancer characterized by increased expression of piR_020582 and/or piR_004987.

3. Cancers to Diagnose and Treat

The compositions and methods can be applied to benign and malignant breast tumors and cancers. Types of breast cancer include, for example, DCIS—Ductal Carcinoma In Situ, IDC—Invasive Ductal Carcinoma, IDC Type: Tubular Carcinoma of the Breast, IDC Type: Medullary Carcinoma of the Breast, IDC Type: Mucinous Carcinoma of the Breast, IDC Type: Papillary Carcinoma of the Breast, IDC Type: Cribriform Carcinoma of the Breast, ILC—Invasive Lobular Carcinoma, Inflammatory Breast Cancer, LCIS—Lobular Carcinoma In Situ, Male Breast Cancer, Paget's Disease of the Nipple, Phyllodes Tumors of the Breast, Recurrent & Metastatic Breast Cancer.

Breast cancers can also be categorized based on intrinsic or molecular subtypes including luminal A, luminal B, triple-negative/basal-like, HER2-enriched, and normal-like.

F. Chart of Preferred Aberrant piRNAs

| piRNA | Aberrantly Expressed in Tissue/ Cancer | Accession Number | Nucleotide Sequence |
|---|---|---|---|
| piR-2799 | brain | DQ572563 | TCAAAGAGAAGGGGTCCTAGATGTTC (SEQ ID NO: 1) |
| piR-18913 | brain | DQ588602 | TGGGAATGTGACCCGCGAATATTGTTGCC (SEQ ID NO: 2) |
| piR-598 | brain | DQ570289 | ACACTGCAATGAGCCAGTCAAATGGGAGTTC (SEQ ID NO: 3) |
| piR-11714 | brain | DQ581429 | TGATAGTCACACAGACAGGCCTTCATGA (SEQ ID NO: 4) |

-continued

| piRNA | Aberrantly Expressed in Tissue/ Cancer | Accession Number | Nucleotide Sequence |
|---|---|---|---|
| piR-3266 | brain | DQ572958 | TCACAGCATGGAGCGTCACGATAGGGGATC (SEQ ID NO: 5) |
| piR-8041 | brain | DQ580941 | TGAGGCGGGCGCCATGCAGACGGGCA (SEQ ID NO: 6) |
| piR-54022 | brain | DQ586910 | TGGACGGACGGATGGCCAGATGAATCAAAACT (SEQ ID NO: 7) |
| piR-20249 | brain | DQ597805 | GGATATGGAAATGAGAGGACGGACAAGC (SEQ ID NO: 8) |
| piR-15988 | brain | DQ591832 | TGTGGACTGTCTCAGGAGGCAGAGGGGCACC (SEQ ID NO: 9) |
| piR-37213 (29114) | liver | DQ599147 | TAACGCCAAGGTCGCGGGTTCGAACCCCGTA (SEQ ID NO: 10) |
| piR-17656 | liver | DQ587366 | TGGATGTCTGCCTCTACTAACTGGGA (SEQ ID NO: 11) |
| piR-33404 (23555) | liver | DQ593292 | CGCCATCTTCAGCAAACCCTGATGAAGGCTA (SEQ ID NO: 12) |
| piR-021163 | prostate | DQ590869 | TGTATGTGTTCCAATGTTTAGTCGGC (SEQ ID NO: 13) |
| piR-003123 | prostate | DQ572799 | TCAAGTGTTTTGGTTCAATGAATGGTC (SEQ ID NO: 14) |
| piR-008061 | prostate | DQ577802 | TCTGATCTACCATCATTGTTTAATGTTCGGC (SEQ ID NO: 15) |
| piR-013783 | prostate | DQ583503 | TGCACTGACATGGACCCCGAGCCGCAGACC (SEQ ID NO: 16) |
| piR-14246 | prostate | DQ584010 | TGCATGTGGAGACGCAGATGCCTGACAAAG (SEQ ID NO: 17) |
| piR-008286 | prostate | DQ578027 | TCTGGCAAGGACGGCTTGGTGTGCACGC (SEQ ID NO: 18) |
| piR-018495 | prostate | DQ588262 | TGGCTTTTGTAGAATGTAGGTCTTCACTGT (SEQ ID NO: 19) |
| piR-21626 | lung | DQ591361 | TGTGAATGAATCGCCTTTGTCTTGTTGGT (SEQ ID NO: 20) |
| piR-16828 | lung | DQ586508 | TGGAACAGGAAAGAAAGCCAAGACCTGTA (SEQ ID NO: 21) |
| piR-5247 | lung | DQ574941 | TCCATTAGGGTCCTGCTGGGATGGAGTGT (SEQ ID NO: 22) |
| piR-5671 | lung | DQ575393 | TCCCCATGACTCAATCAAGGACTGTGCTA (SEQ ID NO: 23) |
| piR-14620 | lung | DQ584878 | TGCCTAAGATGATTGAGTTCCCGAGG (SEQ ID NO: 24) |
| piR-20009 | lung | DQ589741 | TGGTAACAGTGTGCAAAGCTCTAGGGTGA (SEQ ID NO: 25) |
| piR-31637 | lung | DQ601367 | TAGCTTCGATCGTTCGAATTCAGAGC (SEQ ID NO: 26) |
| piR-2732 | lung | DQ572496 | TATTTCAGGAATGCAAGAAGGTGGTTC (SEQ ID NO: 27) |
| piR-19521 | lung | DQ589239 | TGGGGAATCTGATCGCCTGTATCCTACCTC (SEQ ID NO: 28) |

-continued

| piRNA | Aberrantly Expressed in Tissue/ Cancer | Accession Number | Nucleotide Sequence |
|---|---|---|---|
| piR-15232 | lung | DQ584921 | TGCCTATGTGGTGTTTGGCAAAACATG (SEQ ID NO: 29) |
| piR-17319 | breast | DQ587013 | TGGAGAGATTATTACATACTTGCCTTTTCTGC (SEQ ID NO: 30) |
| piR-9422 | breast | DQ579124 | TGAAGTCAACGTACATGGTAGCAGAGT (SEQ ID NO: 31) |
| piR-16556 | breast | DQ586335 | TGGAAAAAACGCCGAAACTGATGGCCC (SEQ ID NO: 32) |
| piR-3467 | breast | DQ573174 | TCACGTCCAGTTTGATCTGGTGGATGTGT (SEQ ID NO: 33) |
| piR_016975 | breast | DQ586669 | TGGAAGTGGATTTCCGGTGAAGGATGG (SEQ ID NO: 34) |
| piR_019169 | breast | DQ588872 | TGGGATGAGAAGTCTGGAGGGCACGG (SEQ ID NO: 35) |
| piR_018292 | breast | DQ588045 | TGGCGCACGATGTAGGGCACCTTGGACCTC (SEQ ID NO: 36) |
| piR_017178 | breast | DQ586872 | TGGACCCAGTCATGGACCTGTTAGTGC (SEQ ID NO: 37) |
| piR_019368 | breast | DQ589086 | TGGGCCCTCCCCTAGAGTGTTCCTGCA (SEQ ID NO: 38) |
| piR_019911 | breast | DQ589643 | TGGGTGTTGCCCAATTGGTGGCCAAC (SEQ ID NO: 39) |
| piR_000560 | breast | DQ570251 | ACACACACTTGATTGTTCTGGATGAA (SEQ ID NO: 40) |
| piR_001207 | breast | DQ570956 | AGCATTGGTGGTTCAGTGGTAGAATTCTCGC (SEQ ID NO: 41) |
| piR_012753 | breast | DQ582530 | CATCTGTGCAGTGCAAGTGATCCACGCCT (SEQ ID NO: 42) |
| piR_003728 | breast | DQ573435 | TCAGATGCCAGCCAAAGGTTTGTGGATC (SEQ ID NO: 43) |
| piR_001078 | breast | DQ570813 | AGAGAGTACAATGGTGGTTACCAGAGA (SEQ ID NO: 44) |
| piR_012925 | breast | DQ583881 | TGCAGTTTGCTGATGGCTAGTAGGGT (SEQ ID NO: 45) |
| piR_020582 | breast | DQ590358 | TGGTGGGAAAATTTCAGTTTCATGAGAAGTG (SEQ ID NO: 46) |
| piR_004987 | breast | DQ574652 | TCCAGGATGTAACTAGAGAGCTACGGGT (SEQ ID NO: 47) |

All of the accession numbers in Chart of Preferred Aberrant piRNAs above and all other accessions numbers disclosed herein are specifically incorporated by reference in their entireties. In some places herein piRNA are as DNA sequence (e.g., DNA sequences encoding piRNA sequence) and in some places as RNA sequences. Where the DNA sequence is disclosed the RNA sequences is also expressly disclosed (e.g., by replacing "T" with a "U"). Likewise, where the RNA sequence is disclose, the corresponding DNA sequence is also expressly disclosed (e.g., by replacing "U" with "T").

III. Compositions

A. Active Agents

1. Agents for Increasing Expression of an Aberrant piRNA

As introduced above, agents for increasing expression of an aberrant piRNA can be, for example, wildtype piRNA, or close variants thereof with the same or similar activity to wildtype, or a stimulator of expression thereof. Close variants are typically sequence variants with at least 80%, 85%, 90%, 91%, 92%, 93%, 94%, 95%, 96%, 97%, 98%, 99%, or more sequence identity with the wildtype piRNA. Most typically, the activity of the close variant has the same or similar, or even improved activity (e.g., regulation of its target mRNA(s)), relative to the corresponding wildtype. Variants that significantly reduce activity of the piRNA relative to wildtype may not be effective for the therapies disclosed herein and can be excluded.

Stimulators of piRNA expression can be, for example, small molecules, proteins, nucleic acids, etc., that increase genomic expression of a piRNA. For example, a transcription factor that increases expression of a target piRNA can be stimulator of expression of that piRNA.

Methods of making, expressing, and using piRNA and mimics thereof are known in the art and disclosed in the working Examples below. See also, for example, Jacobs et. al., Can. Epi. Biol. Prev., 25(7):1073-80, 2016), which along with all of its supplemental materials, is specifically incorporated by reference in its entirety.

2. Agents for Reducing Expression of an Aberrant piRNA

Agents that reduce expression of an aberrant piRNA can be a functional nucleic acid. Functional nucleic acids are nucleic acid molecules that have a specific function, such as binding a target molecule or catalyzing a specific reaction. As discussed in more detail below, functional nucleic acid molecules can be divided into the following non-limiting categories: antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

The functional nucleic acid is typically designed to target the piRNA itself, or a genomic sequence encoding the piRNA, and thus reduce its expression. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Therefore, the compositions can include one or more functional nucleic acids designed to reduce expression of a piRNA gene, or the piRNA itself.

In some embodiments, the functional nucleic acids induce gene silencing through RNA interference. Gene expression can also be effectively silenced in a highly specific manner through RNA interference (RNAi). This silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, et al. (2001) Genes Dev., 15:188-200; Bernstein, et al. (2001) Nature, 409:363-6; Hammond, et al. (2000) Nature, 404: 293-6). In an ATP dependent step, the siRNAs become integrated into a multi-subunit protein complex, commonly known as the RNAi induced silencing complex (RISC), which guides the siRNAs to the target RNA sequence (Nykanen, et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, a siRNA triggers the specific degradation of homologous RNA molecules, such as piRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs.

Sequence specific gene silencing can be achieved in mammalian cells using synthetic, short double-stranded RNAs that mimic the siRNAs produced by the enzyme dicer (Elbashir, et al. (2001) Nature, 411:494 498) (Ui-Tei, et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAse (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors. In some embodiments, the functional nucleic acid is siRNA, shRNA, miRNA. In some embodiments, the composition includes a vector expressing the functional nucleic acid. Methods of making and using vectors for in vivo expression of functional nucleic acids such as antisense oligonucleotides, siRNA, shRNA, miRNA, EGSs, ribozymes, and aptamers are known in the art.

In some embodiments the functional nucleic acids are gene editing compositions. Gene editing compositions can include nucleic acids that encode an element or elements that induce a single or a double strand break in the target cell's genome, and optionally a polynucleotide. The compositions can be used, for example, to reduce or otherwise modify expression of a piRNA. Systems for gene modification are known in the art and include, for example, CRISPR/Cas, Zinc Finger Nucleases, and Transcription Activator-Like Effector Nucleases (TALEN).

B. Compositions and Methods of Deploying Active Agents

Nucleic acid active agents including piRNA and functional nucleic acids can be administered to a subject in need thereof. The piRNA or functional nucleic acid can also be encoded by a vector or virus that is administered to a subject in need thereof. For example, a sequence encoding a piRNA or function nucleic acid can be incorporated into an autonomously replicating plasmid, a virus (e.g., a retrovirus, lentivirus, adenovirus, or herpes virus). Sequence encoding the piRNA or functional nucleic acid can also be integrated into genomic DNA of a subject.

Nucleic acids can be delivered by a viral vector, for example a commercially available preparation, such as an adenovirus vector (Quantum Biotechnologies, Inc. (Laval, Quebec, Canada). The viral vector delivery can be via a viral system, such as a retroviral vector system which can package a recombinant retroviral genome (see e.g., Pastan et al., (1988) *Proc. Natl. Acad. Sci*. U.S.A. 85:4486; Miller et al., (1986) Mol. Cell. Biol. 6:2895). The recombinant retrovirus can then be used to infect and thereby deliver to the infected cells nucleic acid encoding the agent. The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948 (1994)), adeno-associated viral (AAV) vectors (Goodman et al., *Blood* 84:1492-1500 (1994)), lentiviral vectors (Naidini et al., *Science* 272:263-267 (1996)), pseudotyped retroviral vectors (Agrawal et al., *Exper. Hematol.* 24:738-747 (1996)).

C. Nucleic Acid Modifications

Many of the active agents utilized for the therapies disclosed herein are nucleic acid-based therapies. Although piRNA, and inhibitors thereof, are typically active as RNA, it will be appreciated that the active agents include one or more modifications to increase activity, reduce degradation, or a combination thereof. Thus in some embodiments, the piRNA or a functional nucleic acid targeting a piRNA, or any vector or virus including the piRNA or function nucleic acid, include one or more of the following modifications provided it does not prevent its desired activity.

The disclosed can be or include DNA or RNA nucleotides or a combination thereof which typically include a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose sugar linked by phosphodiester bonds.

In some embodiments, the nucleic acids are composed of nucleotide analogs that have been chemically modified to improve stability, half-life, or specificity or affinity for a target receptor, relative to a DNA or RNA counterpart. The chemical modifications include chemical modification of nucleobases, sugar moieties, nucleotide linkages, or combinations thereof. As used herein 'modified nucleotide" or "chemically modified nucleotide" defines a nucleotide that has a chemical modification of one or more of the heterocyclic base, sugar moiety or phosphate moiety constituents. In some embodiments, the charge of the modified nucleotide is reduced compared to DNA or RNA oligonucleotides of the same nucleobase sequence. For example, the nucleic acids can have low negative charge, no charge, or positive charge.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). In some embodiments, the analogs have a substantially uncharged, phosphorus containing backbone.

1. Heterocyclic Bases

The principal naturally-occurring nucleotides include uracil, thymine, cytosine, adenine and guanine as the heterocyclic bases. The nucleic acids can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-.beta.-D-ribofuranosyl)pyridine (2-aminopyridine), and various pyrrolo- and pyrazolopyrimidine derivatives.

2. Sugar Modifications

Nucleic acids can also contain nucleotides with modified sugar moieties or sugar moiety analogs. Sugar moiety modifications include, but are not limited to, 2'-O-aminoetoxy, 2'-O-amonioethyl (2'-OAE), 2'-O-methoxy, 2'-O-methyl, 2-guanidoethyl (2'-OGE), 2'-O,4'-C-methylene (LNA), 2'-O-(methoxyethyl) (2'-OME) and 2'-O—(N-(methyl)acetamido) (2'-OMA). 2'-O-aminoethyl sugar moiety substitutions are especially preferred because they are protonated at neutral pH and thus suppress the charge repulsion between the TFO and the target duplex. This modification stabilizes the C3'-endo conformation of the ribose or dexyribose and also forms a bridge with the i-1 phosphate in the purine strand of the duplex.

In some embodiments, the nucleic acid is a morpholino. Morpholino oligonucleotides are typically composed of two more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of an oligomer:RNA heteroduplex to resist RNAse degradation.

In some embodiments, oligonucleotides employ morpholino-based subunits bearing base-pairing moieties, joined by uncharged linkages, as described above.

3. Internucleotide Linkages

Nucleic acids connected by an internucleotide bond that refers to a chemical linkage between two nucleoside moieties. Modifications to the phosphate backbone of DNA or RNA may increase the binding affinity or stability oligonucleotides, or reduce the susceptibility of oligonucleotides to nuclease digestion. Cationic modifications, including, but not limited to, diethyl-ethylenediamide (DEED) or dimethyl-aminopropylamine (DMAP) may be especially useful due to decrease electrostatic repulsion between the oligonucleotide and a target. Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable in vivo.

Examples of modified nucleotides with reduced charge include modified internucleotide linkages such as phosphate analogs having achiral and uncharged intersubunit linkages (e.g., Sterchak, E. P. et al., *Organic. Chem.*, 52:4202, (1987)), and uncharged morpholino-based polymers having achiral intersubunit linkages (see, e.g., U.S. Pat. No. 5,034, 506), as discussed above. Some internucleotide linkage analogs include morpholidate, acetal, and polyamide-linked heterocycles.

In another embodiment, the nucleic acids are composed of locked nucleic acids. Locked nucleic acids (LNA) are modified RNA nucleotides (see, for example, Braasch, et al., *Chem. Biol.*, 8(1):1-7 (2001)). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the nucleic acids are composed of peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are comprised of peptide nucleic acid monomers.

Other backbone modifications include peptide and amino acid variations and modifications. Thus, the backbone constituents of oligonucleotides such as PNA may be peptide linkages, or alternatively, they may be non-peptide peptide linkages. Examples include acetyl caps, amino spacers such as 8-amino-3,6-dioxaoctanoic acid (referred to herein as O-linkers), amino acids such as lysine are particularly useful if positive charges are desired in the PNA, and the like. Methods for the chemical assembly of PNAs are well known. See, for example, U.S. Pat. Nos. 5,539,082, 5,527, 675, 5,623,049, 5,714,331, 5,736,336, 5,773,571 and 5,786, 571.

Nucleic acids optionally include one or more terminal residues or modifications at either or both termini to increase stability, and/or affinity of the oligonucleotide for its target. Commonly used positively charged moieties include the amino acids lysine and arginine, although other positively charged moieties may also be useful. nucleic acids may further be modified to be end capped to prevent degradation using a propylamine group. Procedures for 3' or 5' capping oligonucleotides are well known in the art.

In some embodiments, the nucleic acid is single stranded or double stranded.

D. Delivery Vehicles

The disclosed agents can be administered and taken up into the cells of a subject with or without the aid of a delivery vehicle. Appropriate delivery vehicles for the disclosed agents are known in the art and can be selected to suit the particular inhibitor.

Physical transduction techniques can also be used, such as liposome delivery and receptor-mediated and other endocytosis mechanisms (see, for example, Schwartzenberger et al., *Blood* 87:472-478 (1996)). For example in some embodiments, the agents can be delivered via a liposome. Commercially available liposome preparations such as LIPO-FECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art are well known. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.). This disclosed compositions and methods can be used in conjunction with any of these or other commonly used gene transfer methods.

In some embodiments, the delivery vehicle is incorporated into or encapsulated by a nanoparticle, microparticle, micelle, synthetic lipoprotein particle, or carbon nanotube. For example, the compositions can be incorporated into a vehicle such as polymeric microparticles which provide controlled release of the agent. In some embodiments, release of the drug(s) is controlled by diffusion of the agent out of the microparticles and/or degradation of the polymeric particles by hydrolysis and/or enzymatic degradation. Suitable polymers include ethylcellulose and other natural or synthetic cellulose derivatives. Polymers which are slowly soluble and form a gel in an aqueous environment, such as hydroxypropyl methylcellulose or polyethylene oxide may also be suitable as materials for drug containing microparticles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof.

The agent can be incorporated into or prepared from materials which are insoluble in aqueous solution or slowly soluble in aqueous solution, but are capable of degrading within the GI tract by means including enzymatic degradation, surfactant action of bile acids, and/or mechanical erosion. As used herein, the term "slowly soluble in water" refers to materials that are not dissolved in water within a period of 30 minutes. Preferred examples include fats, fatty substances, waxes, waxlike substances and mixtures thereof. Suitable fats and fatty substances include fatty alcohols (such as lauryl, myristyl stearyl, cetyl or cetostearyl alcohol), fatty acids and derivatives, including, but not limited to, fatty acid esters, fatty acid glycerides (mono-, di- and tri-glycerides), and hydrogenated fats. Specific examples include, but are not limited to hydrogenated vegetable oil, hydrogenated cottonseed oil, hydrogenated castor oil, hydrogenated oils available under the trade name Sterotex®, stearic acid, cocoa butter, and stearyl alcohol. Suitable waxes and wax-like materials include natural or synthetic waxes, hydrocarbons, and normal waxes.

Specific examples of waxes include beeswax, glycowax, castor wax, carnauba wax, paraffins and candelilla wax. As used herein, a wax-like material is defined as any material which is normally solid at room temperature and has a melting point of from about 30 to 300° C.

Exemplary vehicles for delivery of nucleic acid drugs, include, but are not limited to, polymer-based nanoparticles and polyplex nanogel formulations. See, for example, Hilaireau, et al., *J. Nanosci. Nanotechnol.*, 6(9-10):2608-17 (2006), Vinogradov, et al, *J. Control Release,* 107(1):143-57 (2005), and Vinogradov, *Expert Opin Drug Deliv.* 4(1): 5-17 (2007), each of which is specifically incorporated by reference in its entirety.

E. Targeting Signal or Domain

The compositions can be optionally modified to include one or more targeting signals, ligands, or domains. The targeting signal can be operably linked with the active agent, or a delivery vehicle such as a microparticle. For example, in some embodiments, the targeting signal is linked or conjugated directly or indirectly to the active agent. In some embodiments, the targeting signal is linked, conjugated, or associated directly, or indirectly, with a delivery vehicle such as a liposome or a nanoparticle. The targeting signal or sequence can be specific for a host, tissue, organ, cell, organelle, non-nuclear organelle, or cellular compartment.

In some embodiments, the targeting signal binds to its ligand or receptor which is located on the surface of a target cell such as to bring the composition or a delivery vehicle thereof and cell membranes sufficiently close to each other to allow penetration of the composition or delivery vehicle into the cell. In a preferred embodiment, the targeting molecule is selected from the group consisting of an antibody or antigen binding fragment thereof, an antibody domain, an antigen, a cell surface receptor, a cell surface adhesion molecule, a major histocompatibility locus protein, a viral envelope protein and a peptide selected by phage display that binds specifically to a defined cell.

Targeting the compositions or delivery vehicles to specific cells can be accomplished by modifying the disclosed compositions or delivery vehicles to express specific cell and tissue targeting signals. These sequences target specific cells and tissues, but in some embodiments the interaction of the targeting signal with the cell does not occur through a traditional receptor:ligand interaction. Eukaryotic cells have a number of distinct cell surface molecules. The structure and function of each molecule can be specific to the origin, expression, character and structure of the cell. Determining the unique cell surface complement of molecules of a specific cell type can be determined using techniques well known in the art.

One skilled in the art will appreciate that the tropism of the compositions or delivery vehicles described can be altered by merely changing the targeting signal. In one specific embodiment, compositions are provided that enable the addition of cell surface antigen specific antibodies to the composition or delivery vehicle for targeting the delivery the active agent to the target cells.

It is known in the art that nearly every cell type in a tissue in a mammalian organism possesses some unique cell surface receptor or antigen. Thus, it is possible to incorporate nearly any ligand for the cell surface receptor or antigen as a targeting signal. For example, peptidyl hormones can be used a targeting moieties to target delivery to those cells which possess receptors for such hormones. Chemokines and cytokines can similarly be employed as targeting signals to target delivery of the complex to their target cells. Compounds that bind to cancer antigens can be employed as targeting signals to target delivery of the complex to their target cancer cells. A variety of technologies have been developed to identify genes that are preferentially expressed in certain cells or cell states and one of skill in the art can employ such technology to identify targeting signals which are preferentially or uniquely expressed on the target tissue of interest.

In some embodiments, the targeting signal is or includes a protein transduction domain, also known as cell penetrating peptides (CPPS). PTDs are known in the art, and include but are not limited to small regions of proteins that are able to cross a cell membrane in a receptor-independent mechanism (Kabouridis, P., *Trends in Biotechnology* (11):498-503 (2003)). Two of the most commonly employed PTDs are derived from TAT (Frankel and Pabo, Cell, December 23; 55(6):1189-93 (1988)) protein of HIV and Antennapedia transcription factor from *Drosophila*, whose PTD is known as Penetratin (Derossi et al., J Biol Chem. 269(14):10444-50 (1994)).

The Antennapedia homeodomain is 68 amino acid residues long and contains four alpha helices. Penetratin is an active domain of this protein which consists of a 16 amino acid sequence derived from the third helix of Antennapedia. TAT protein consists of 86 amino acids and is involved in the replication of HIV-1. The TAT PTD typically consists of an 11 amino acid sequence domain of the parent protein that appears to be critical for uptake. Additionally, the basic domain Tat(49-57) has been shown to be a PTD.

Several modifications to TAT, including substitutions of Glutatmine to Alanine, i.e., Q-to-A, have demonstrated an increase in cellular uptake anywhere from 90% to up to 33 fold in mammalian cells. (Ho et al., Cancer Res. 61(2):474-7 (2001)) The most efficient uptake of modified proteins was revealed by mutagenesis experiments of TAT-PTD, showing that an 11 arginine stretch was several orders of magnitude more efficient as an intercellular delivery vehicle. Thus, some embodiments include PTDs that are cationic or amphipathic. Additionally exemplary PTDs include but are not limited to poly-Arg; PTD-5; Transportan; and KALA.

D. Formulations Pharmaceutical compositions including one or more active agents are also disclosed.

1. Pharmaceutical Compositions

Pharmaceutical compositions including an active agent, and optionally a targeting moiety, a delivery vehicle, or a combination thereof are provided. Pharmaceutical compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

The compositions can be administered systemically, by for example, injection or infusion. In certain embodiments, the compositions are administered locally, for example by injection directly into a site to be treated (e.g., a tumor). In some embodiments, the compositions are injected, topically applied, or otherwise administered directly into the vasculature. Typically, local administration causes an increased localized concentration of the compositions which is greater than that which can be achieved by systemic administration.

a. Formulations for Parenteral Administration

Compositions including an active agent can be administered in an aqueous solution, by parenteral injection. The formulation may also be in the form of a suspension or emulsion. In general, pharmaceutical compositions are provided including effective amounts of the active agent and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

b. Oral Formulations

Oral formulations may be in the form of chewing gum, gel strips, tablets or lozenges. Encapsulating substances for the preparation of enteric-coated oral formulations include cellulose acetate phthalate, polyvinyl acetate phthalate, hydroxypropyl methylcellulose phthalate and methacrylic acid ester copolymers. Solid oral formulations such as capsules or tablets are preferred. Elixirs and syrups also are well known oral formulations. The components of aerosol formulations include solubilized active ingredients, antioxidants, solvent blends and propellants for solution formulations, and micronized and suspended active ingredients, dispersing agents and propellants for suspension formulations. The oral, aerosol and nasal formulations of the invention can be distinguished from injectable preparations of the prior art because such formulations may be nonaseptic, whereas injectable preparations must be aseptic.

c. Formulations for Topical Administration

The active agent can be applied topically. Topical administration can include application to the lungs, nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acom® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

Transdermal formulations may also be prepared. These will typically be ointments, lotions, sprays, or patches, all of which can be prepared using standard technology. Transdermal formulations can include penetration enhancers.

2. Effective Amounts

In some in vivo approaches, the compositions are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect.

Therapeutically effective amounts of active agents used in the treatment of cancer will generally kill tumor cells or inhibit proliferation or metastasis of the tumor cells. Symptoms of cancer may be physical, such as tumor burden, or biological such as proliferation, resistance to apoptosis, migration, colony formation in soft agar, etc. The actual effective amounts of active agent can vary according to factors including the specific active agent administered, the particular composition formulated, the mode of administration, and the age, weight, condition of the subject being treated, as well as the route of administration and the disease or disorder.

An effective amount of the active agent can be compared to a control. Suitable controls are known in the art. A typical control is a comparison of a condition or symptom of a subject prior to and after administration of the active agent. The condition or symptom can be a biochemical, molecular, physiological, or pathological readout. In another embodiment, the control is a matched subject that is administered a different therapeutic agent. Accordingly, the compositions disclosed here can be compared to other art recognized treatments for the disease or condition to be treated.

The active agent can be administered in an amount effective to reduce the tumorigenicity of the cancer cells, reduce or reverse one or more phenotypes of the cancer cells, improve survival of a subject with cancer, or a combination thereof.

The precise dosage will vary according to a variety of factors such as subject-dependent variables (e.g., age, immune system health, etc.), the disease, and the treatment being effected. As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally, dosage levels of 0.001 to 10 mg/kg of body weight daily are administered to mammals. Generally, for intravenous injection or infusion, dosage may be lower.

IV. Methods of Use

A. Methods of Cancer Treatment

As introduced above, the methods of cancer treatment typically involve administering a subject in need thereof an effective amount of an active agent to alter the effect of an aberrantly expressed piRNA. The subject in need thereof typically has or is at an increased likelihood of developing a cancer. The method is typically carried out such that the composition enters affected or other target cells (e.g., cancer cells or cells likely to become cancerous) and alters the effect of the aberrantly expressed piRNA. Thus, the therapies disclosed herein often include transfection of target cells with the active agent such as a nucleic acid or an inhibitor thereof. Most typically a sufficient number of effect cells are treated to change to the course of the disease, for example, reduce, prevent, or reverse tumor or cancer progression, etc.

If the piRNA is increased in a tumor relative to normal tissue, the method can include administering the subject in need thereof an effective amount of an agent that reduces expression of piRNA to treat the cancer. If the piRNA is reduced in a tumor relative to normal tissue, or the subject exhibits a mutation in the piRNA (e.g., a SNP) relative to the consensus wildtype sequence, the method can include administering a subject in need thereof an effective amount of an agent that increases expression of piRNA to treat the cancer. The methods can be therapeutic or prophylactic.

As discussed in more detail above and exemplified below, specific piRNAs are linked to specific cancers and prognosis thereof. Thus, the cancer itself can drive selection of the piRNA to be administered or targeted to treat the cancer.

Pharmaceutical compositions including an active agent can be administered once or more than once, for example 2, 3, 4, 5, or more times. Serial administration of the composition may occur days, weeks, or months apart.

The compositions can be used in combination with one or more additional therapeutic agents. The term "combination" or "combined" is used to refer to either concomitant, simultaneous, or sequential administration of two or more agents. Therefore, the combinations can be administered either concomitantly (e.g., as an admixture), separately but simultaneously (e.g., via separate intravenous lines into the same subject), or sequentially (e.g., one of the compounds or agents is given first followed by the second). The additional therapeutic agents can be administered locally or systemically to the subject, or coated or incorporated onto, or into a device or graft.

Administration of the disclosed compositions may be coupled with surgical, radiologic, other therapeutic approaches to treatment of tumors and cancers.

1. Surgery

The disclosed compositions and methods can be used as an adjunct to surgery. Surgery is a common treatment for many types of benign and malignant tumors. As it is often not possible to remove all the tumor cells from during surgery, the disclosed compositions can be used subsequent to resection of the primary tumor mass to treat linger cancer cells.

In a preferred embodiment, the disclosed compositions and methods are used as an adjunct or alternative to neurosurgery. The compositions are particularly well suited to treat areas of the brain that is difficult to treat surgically, for instance high grade tumors of the brain stem, motor cortex, basal ganglia, or internal capsule. High grade gliomas in these locations are generally considered inoperable. An additional situation where the compositions may be helpful is in regions where the tumor is either wrapped around critical vasculature, or in an area that is difficult to treat surgically.

2. Therapeutic Agents

The compositions can be administered to a subject in need thereof alone or in combination with one or more additional therapeutic agents selected based on the condition, disorder or disease to be treated. A description of the various classes of suitable pharmacological agents and drugs may be found in Goodman and Gilman, *The Pharmacological Basis of Therapeutics*, (11 th Ed., McGraw-Hill Publishing Co.) (2005).

Additional therapeutic agents include conventional cancer therapeutics such as chemotherapeutic agents, cytokines, chemokines, and radiation therapy. The majority of chemotherapeutic drugs can be divided into: alkylating agents, antimetabolites, anthracyclines, plant alkaloids, topoisomerase inhibitors, and other antitumour agents. All of these drugs affect cell division or DNA synthesis and function in some way. Additional therapeutics include monoclonal antibodies and the tyrosine kinase inhibitors e.g., imatinib mesylate (GLEEVEC® or GLIVEC®), which directly targets a molecular abnormality in certain types of cancer (chronic myelogenous leukemia, gastrointestinal stromal tumors).

Representative chemotherapeutic agents include, but are not limited to, amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epipodophyllotoxins, epirubicin, etoposide, etoposide phosphate, fludarabine, fluorouracil, gemcitabine, hydroxycarbamide, idarubicin, ifosfamide, irinotecan, leucovorin, liposomal doxorubicin, liposomal daunorubicin, lomustine, mechlorethamine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, teniposide, tegafur-uracil, temozolomide, teniposide, thiotepa, tioguanine, topotecan, treosulfan, vinblastine, vincristine, vindesine, vinorelbine, taxol and derivatives thereof, trastuzumab (HERCEPTIN®), cetuximab, and rituximab (RITUXAN® or MABTHERA®), bevacizumab (AVASTIN®), and combinations thereof. Representative pro-apoptotic agents include, but are not limited to, fludarabinetaurosporine, cycloheximide, actinomycin D, lactosylceramide, 15d-PGJ(2), and combinations thereof.

Preferred chemotherapeutics will affect tumors or cancer cells, without diminishing the activity of the other active agent(s).

The compositions can be administered with an antibody or antigen binding fragment thereof specific for growth factor receptors or tumor specific antigens. Representative growth factors receptors include, but are not limited to, epidermal growth factor receptor (EGFR; HER1); c-erbB2 (HER2); c-erbB3 (HER3); c-erbB4 (HER4); insulin receptor; insulin-like growth factor receptor 1 (IGF-1R); insulin-like growth factor receptor 2/Mannose-6-phosphate receptor (IGF-II R/M-6-P receptor); insulin receptor related kinase (IRRK); platelet-derived growth factor receptor (PDGFR); colony-stimulating factor-ireceptor (CSF-1R) (c-Fms); steel receptor (c-Kit); Flk2/Flt3; fibroblast growth factor receptor 1 (Flg/Cek1); fibroblast growth factor receptor 2 (Bek/Cek3/K-Sam); Fibroblast growth factor receptor 3; Fibroblast growth factor eceptor 4; nerve growth factor receptor (NGFR) (TrkA); BDNF receptor (TrkB); NT-3-receptor (TrkC); vascular endothelial growth factor receptor 1 (Flt1); vascular endothelial growth factor receptor 2/Flk1/KDR; hepatocyte growth factor receptor (HGF-R/Met); Eph; Eck; Eek; Cek4/Mek4/HEK Cek5; Elk/Cek6; Cek7; Sek/Cek8; Cek9; Cek10; HEK11; 9 Ror1; Ror2; Ret; Ax1; RYK; DDR; and Tie.

V. Methods of Diagnosis and Prognosis Based on Aberrant piRNA Expression

Any of the aberrantly expressed piRNA can be used as biomarkers to diagnose or grade the severity and treatability of a cancer.

A. Dysregulated piRNA

The dysregulated piRNA disclosed herein can be used to detect, diagnose, or prognoses a cancer associated therewith. The methods typically include obtaining a measured valve for one of more of the dysregulated piRNA. The methods typically include measuring the level of one or more piRNAs in a biological sample and comparing it to a control or reference value. The biological sample can be tumor sample. Furthermore, as with miRNA, piRNAs remain largely undegraded in circulation and have the ability to resist a wide range of incubation and storage conditions regularly used in the laboratory (Ng, et al., *Molecular Cancer*, (2016) 15:5 DOI 10.1186/s12943-016-0491-9 (13 pages)). A recent study of piRNAs in gastric cancer found that, when compared to an existing miRNA-based biomarker detection system, piRNAs provided higher sensitivity and specificity. Thus, in some embodiments, the sample can be a blood sample. The blood sample can be derived from whole blood, serum or plasma.

In some embodiments, the measured level(s) is compared to a reference value to determine if the subject has the cancer or if the subject is likely to develop the cancer. When the reference level is the level of the piRNA in normal blood or tissue, the subject is diagnosed with cancer if the piRNA is over or underexpressed in the measured value relative to the reference value in accordance with the correlations discussed herein. For example, if the selected piRNA is increased in cancer relative to normal tissue as described herein, the subject can be diagnosed, selected, etc., when the level of the piRNA in the biological sample is increased relative to the control. Similarly, if the selected piRNA is decreased in cancer relative to normal tissue as described herein, the subject can be diagnosed, selected, etc. when the level of the piRNA in the biological sample is decreased relative to the control.

Additionally or alternatively, when the reference level is the level of the piRNA in the blood or tissue of a previous cancer diagnosis, the subject is diagnosed with cancer if the piRNA is the same or similar in the measured value relative to the reference value in accordance with the correlations discussed herein. The reference value can be an absolute value or range of absolute values. The reference value can be a relative value or range of relative values.

In some embodiments, the comparison of the measured value and the reference value includes calculating a fold difference between the measured value and the reference value. The some embodiments, the fold difference between normal reference value and a measured value is at least 2, 3, 4, or 5 fold.

In some embodiments, the level of piRNA is associated with overall survival and tumor progression, and thus provides a prognostic value. Methods of measuring piRNA levels are discussed in more detail below.

Exemplary methods are provided. For example, cancer in an individual can be diagnosed or detected by quantifying the amount of piRNA in a biological sample of the individual, wherein an increased or decreased amount of the piRNA in the individual's biological sample compared to a control or reference value is indicative of the cancer.

In some embodiments, a method for diagnosing a cancer in a subject can also include determining the levels of piRNA in a first biological sample and a second biological sample taken at a time period after the first sample wherein an increase or decrease in the level of piRNA in the second sample compared to the first sample is indicative of development or worsening of the cancer.

Methods for determining the severity of a cancer is also disclosed. A method can include (a) determining a piRNA in a biological sample from a subject; and (b) comparing the level of piRNA in the biological sample to reference levels of piRNA that correlate with disease severity of a cancer to determine the severity of the cancer in the subject.

Determining severity of a cancer can also be detected or assessed by quantifying the level of piRNA in an individual's biological sample and correlating the amount of piRNA in the individual's biological sample with amount(s) of piRNA indicative of different stages of the cancer.

Methods of selecting a subject for treatment are also provided. A method can include (a) determining the level of piRNA in a biological sample obtained from the subject; (b) comparing the level of piRNA in the biological sample to the level of the piRNA in a control; and (c) selecting the subject for treatment when the level of the piRNA in the biological sample is higher or lower than the level of the piRNA in the control. A method for selecting a subject for treatment can also include determining the levels of piRNA in a first biological sample and a second biological sample taken after the first sample, and selecting the subject for treatment when the level of piRNA in the second biological sample is higher or lower than the level of the piRNA in the first sample.

The amounts of piRNA that correlates with different stages of a cancer or different levels of severity can be predetermined by quantifying piRNA in patients at different stages of the cancer.

Any of the methods may include measuring the level of two or more piRNA. Any of the methods can be combined with a method of treatment. In some embodiments, a downstream target of the piRNA is measured in addition or alternative to measuring expression of the piRNA. Examples of downstream targets, including proteins express levels and signaling pathways affected by piRNA are exemplified below, known in the art, and/or can be determined by experimentation.

B. Expression of piRNA Variants (Mutants)

The mutant piRNA disclosed herein can be used to detect, diagnose, or prognoses or identify a subject likely to develop a cancer associated therewith. The methods typically include determining if the mutant or variant piRNA is expressed in a sample obtained from the subject or present in the genome of the subject.

When determining if the mutant or variant piRNA is expressed, the sample can be a tumor sample or a blood sample as discussed above. However, because the mutant or variant piRNA is encoded by a mutant or variant genomic sequence, the mutant or variant piRNA can also be identified by determining the genomic sequence of the piRNA. Any suitable sample can be utilized for sequencing.

For example, in some embodiments, a method for diagnosing a cancer in a subject or determining that a subject has an increased likelihood of developing a cancer by determining if a variant or mutant piRNA is expressed in a sample from the subject or encoded by the subject's genome.

Methods of selecting a subject for treatment are also provided. A method can include (a) determining if a mutant or variant piRNA is expressed in a biological sample obtained from the subject or encoded by the subject's genome; (b) selecting the subject for treatment when the level of the piRNA in the biological sample is higher or lower than the level of the piRNA in the control; and optionally (c) administering the subject the protective form of piRNA allele (wildtype or variant) identified from genetic association study (which can be directly used for cancer treatment).

Any of the methods may include detecting or determining the presence of two or more variant or mutant piRNAs. Any of the methods can be combined with the foregoing methods related to detection of dysfunctional piRNA, and/or a method of treatment. In some embodiments, a downstream target of the piRNA is measured in addition or alternative to measuring expression of the piRNA or detecting its presence genetically.

C. Methods of Determining Therapeutic Efficacy

In some embodiments, the compositions and methods disclosed herein are used to determine therapeutic efficicy of a treatment for cancer. An active agent can be found efficacious if it reduces, alleviates, or reverses a dysfunctional piRNA. For example, in some embodiments, a method for determining therapeutic efficacy of an active agent in a subject can includes determining the levels of a piRNA in a first biological sample before a treatment with an active agent and a second biological sample taken at a time period after one or more treatments with the active agent wherein an increase or decrease in the level of piRNA in the second sample compared to the first sample is indicative of an efficacious active agent. Typically, if the dysregulated piRNA is increased in the cancer relative to normal tissue, the treatment is efficacious if it reduces expression of the piRNA. Likewise, if the dysregulated piRNA is decreased in the cancer relative to normal tissue, the treatment is efficacious if it increases expression of the piRNA.

In some embodiments, the compositions and methods disclosed herein are used to establish, or modify a dosage regime. For example, the subject can be administered a first dose of the composition for a first dosing period; and a second dose of the composition for a second dosing period, optionally followed by one or more additional doses for one or more additional dosing periods. The first dosing period can be less than one week, one week, or more than one week.

In some embodiments the dosage regime is a dose escalating dosage regime. The first dose can be a low dose. Dose escalation can be continued until a satisfactory biochemical or clinical response is reached. Next, the dosages can be maintained or steadily reduced to a maintenance dose. The methods can be used to standardize, optimize, or customize the dose level, dose frequency, or duration of the therapy.

Methods of determining efficacy and dosing include, but are not limited to, the specific methods of treatment disclosed herein. The methods are also useful for exploring other active agents for the treatment of cancer, including, but not limited to chemotherapeutic agents, immunotherapies, ect.

Any of the methods may include detecting or determining the presence of two or more dysfunction and/or variant or mutant piRNAs. Any of the methods can be combined with and any of the foregoing methods of detecting dysfunctional and/or variant or mutant piRNAs, and/or a method of treatment. In some embodiments, a downstream target of the piRNA is measured in addition or alternative to measuring expression of the piRNA or detecting its presence genetically.

VI. Method of Screening for Aberrant piRNA

Methods of screening for aberrant piRNAs are also provided. Two preferred methods, exemplified in the working examples below, include (1) identifying piRNA that are increased in a cancer or tumor type relative to normal tissue (e.g., expression profiling), and (2) identifying mutations in piRNA of a cancer or tumor type relative to normal tissue (e.g., SNP profiling). These methods can be created out generally according to the methods exemplified below, using, for example, nucleic acid arrays, sequencing, and other laboratory and in silico tools. These methods apply not just to the cancer discussed above and below, but can also be used for exploring the role aberrant piRNA expression in other cancers including, but not limited to, bladder, brain, breast, cervical, colorectal, esophageal, kidney, liver, lung, nasopharyngeal, pancreatic, prostate, skin, stomach, uterine, ovarian, testicular and hematologic.

A. Expression Profiling

Expression profiling is typically carried out by first pooling total RNA in equal proportions by tissue type (tumor and normal). Expression levels can be determined using any suitable means known in the art, however, the most preferred methods is using a piRNA expression array. piRNA expression arrays are commercially available and include probes for thousands of mature human piRNAs.

B. Mutation Profiling

For example, piRNA variants (i.e., piRNA mutations) can be identified using genomic coordinates for experimentally observed piRNAs obtained from a resource such as piRNA-Bank database. Single nucleotide polymorphisms (SNPs), for example from a previously prepared reference set, can be identified within these coordinates.

SNPs in piRNAs that map to >100 genomic loci can be excluded, as these piRNAs are less likely to be involved in protein-coding gene regulation.

Identified SNPs can be investigated to determine if their expression correlates with prevalence of different cancer types (i.e., if the SNP is expressed in a cancer type relative where the corresponding normal tissue expresses wildtype piRNA).

For example, a method of identifying aberrant piRNAs associated with a cancer can include comparing the sequences of piRNA expressed in a normal tissue sample to the sequences of piRNA expressed in cancer tissue and identifying an aberrant piRNA associated with the cancer when the sequence of a piRNA from the cancer tissue is different (e.g., variant, mutant, etc.) from the corresponding piRNA in a normal tissue. The corresponding piRNA in the normal tissue typically means the piRNA encoded at the same genomic locations if the mutant or variant piRNA in the cancer tissue. In some embodiment the variation or mutation is a single nucleotide polymorphism (SNP). In some embodiments, the difference alters that ability of the cancer piRNA to bind to a target mRNA thereof. The mRNA can be an oncogene. In some embodiments, the expression of the wildtype piRNA reduces the tumorigenicity of the cancer.

VII. Methods of Detecting Candidate piRNA

Expressed piRNA can be detected and/or its sequence determined using any suitable means. The methods are typically similar or the same as those used to detect mRNA. Exemplary methods include, but are not limited to, quantitative polymerase chain reaction (qPCR), reverse transcription PCR (RT-PCR), reverse transcription real-time PCR (RT-qPCR), transcriptome analysis using next-generation sequencing, array hybridization analysis, digital PCR, Northern analysis, dot-blot, and in situ hybridization.

Likewise, the genomic sequence of a piRNA can be determined using any suitable means. Examples include, but are not limited to, sequencing and microarray.

The present invention will be further understood by reference to the following non-limiting examples.

EXAMPLES

Example 1: Glioma-Associated piRNAs Identified by Post-GWAS Analysis

It was estimated that nearly 23,400 new cases of primary malignant brain and central nervous system (CNS) tumors would be diagnosed in the United States in 2014; of those, approximately 2,240 would be diagnosed in children ages 0 to 14 years and 540 would be diagnosed in adolescents ages 15 to 19 years. Overall mortality rates have not changed significantly in the past decade. Both incidence and mortality rates are higher for whites than for people of other racial/ethnic groups. In all racial/ethnic groups, men have higher incidence and mortality rates than women. Brain tumors are the leading cause of death from solid tumor cancers in children. Brain and CNS tumors make up approximately 21 percent of all childhood cancers. The incidence rate of brain and CNS cancers in children has been relatively stable since the mid-1980s, but the death rate has dropped over this period.

The causes of most brain and CNS cancers are not known. However, factors that may increase the risk of developing certain types of brain tumors include exposure to radiation, exposure to vinyl chloride, and having certain genetic syndromes. There are no screening tests for brain and CNS cancers. Standard treatments for adult brain cancer include watchful waiting, surgery, radiation therapy, chemotherapy, and targeted therapy. Newer treatments for adult brain cancer, such as biological therapy and proton beam radiation therapy are being studied in clinical trials. Assuming that incidence and survival rates follow recent trends, it is estimated that $4.9 billion will be spent on brain cancer care in the United States in 2014.

Chemotherapy is a cancer treatment that uses drugs to stop the growth of cancer cells, either by killing the cells or by stopping them from dividing. When chemotherapy is taken by mouth or injected into a vein or muscle, the drugs enter the bloodstream and can reach cancer cells throughout the body (systemic chemotherapy). When chemotherapy is placed directly into the cerebrospinal fluid, an organ, or a body cavity such as the abdomen, the drugs mainly affect cancer cells in those areas (regional chemotherapy). Combination chemotherapy is treatment using more than one anticancer drug. To treat brain tumors, a wafer that dissolves can be used to deliver an anticancer drug directly to the brain tumor site after the tumor has been removed by surgery. The way the chemotherapy is given depends on the type and grade of tumor and where it is in the brain.

Anticancer drugs given by mouth or vein to treat brain and spinal cord tumors cannot cross the blood-brain barrier and enter the fluid that surrounds the brain and spinal cord. Instead, an anticancer drug is injected into the fluid-filled space to kill cancer cells there. This is called intrathecal chemotherapy.

Local, sustained drug release using biodegradable polyanhydride poly-(1,3 bis[p-carboxyphenoxy] propane-co-sebacic acid, or p[CPP:SA, 20:80], improves the anti-glioma efficacy of some chemotherapeutic agents for treatment of brain tumors. P[CPP:SA, 20:80] is an FDA-approved method of local drug delivery that has been shown to be biocompatible in the brain with no evidence of systemic or local toxicity and is currently clinically used for the local delivery of BCNU (GLIADEL®).

Despite vast improvements in overall survival rates in systemic cancers, primary brain malignancies still have some of the worst 5-year survival rates among all human cancers (Macmillan Cancer Support. *Living after diagnosis—median cancer survival times: An analysis of London School of Hygiene and Tropical Medicine,* 2011).

Arising from glial cells, gliomas are tumors of the nervous system that account for roughly 80% of all central nervous system malignancies. Glioblastoma multiforme (GBM), arising from astrocytic glial cells, is the most common and aggressive of these tumors and is typified by poorly differentiated astrocytes with highly infiltrative behavior. As of 2010, the median survival time for patients receiving standard-of-care treatment was only 15 months. Despite remarkable progress in the genomic characterization of GBM and the modest improvements in survival following the introduction of temozolomide, major breakthroughs in the treatment of this deadly tumor have remained elusive. Accordingly, the expansion of the understanding of the biology of GBM tumor progression and investigation of new therapeutic opportunities is of the utmost importance.

Materials and Methods

A post-GWAS (Genome-wide association analysis study) analysis was conducted to identify glioma-associated piRNAs. The study population comprised subjects of European ancestry drawn from 14 cohort studies, 3 case-control studies, and 1 population-based case-only study including 1,840 subjects with newly diagnosed glioma and 2,401 cancer-free controls from the GliomaScan consortium.

Study Subjects and Data

Individual-level genotype data and phenotypic subject characteristics for participants of the GliomaScan Cohort-based Genome-wide Association Study were downloaded from the Database of Genotypes and Phenotypes (dbGaP, Study Accession phs000652.v1.p1) after receiving data access authorization. There were 1,840 cases (ICDO-3 codes 9380-9480) and 2,401 controls included for final analysis.

Identification of piRNA Variants

Genomic coordinates for all experimentally observed human piRNAs were obtained from the piRNABank database. Single nucleotide polymorphisms (SNPs) included in the 1,000 Genomes Project Phase 3 reference variant set (n=77,818,332 biallelic SNPs) were identified within these coordinates. SNPs in piRNAs that map to >100 genomic loci were excluded, as these piRNAs are less likely to be involved in protein-coding gene regulation.

piRNA Variant Genotype Imputation

Genotype and phenotype data were downloaded to a secure server at Yale University and decrypted and extracted according to dbGaP guidelines. 1,000 Genomes Phase 3 haplotypes were downloaded for use as the reference panel for imputation using IMPUTE v2.3.1 software. Input data were restricted to SNPs with call rate ≥90% and HWE P>0.0001 using the PLINK toolset. Fine mapping was conducted via imputation of all SNPs with MAF>1% in 5-Mb chunks, and regional annotations were derived from the UCSC Genome Browser.

Statistical Analysis for Association Study

Odds ratios (OR) and 95% confidence intervals (CI) for variant-glioma associations were estimated with SNPTEST v2.5 software, applying an additive allelic logistic regression model adjusting for sex, age, study design, and the first two principal components as generated by the smartPCA algorithm in the EIGENSOFT v6.0 population genetics package. Associations surpassing a Bonferroni-corrected significance threshold were deemed statistically significant and associations yielding false discovery rate-adjusted P-values <0.10 were considered to be modest associations of interest.

Cell Lines and Reagents

Glioma cell lines U87 and A172, purchased from ATCC, and immortalized normal human astrocytes (NHA), purchased from the University of California, San Francisco Tissue Core, were maintained in EMEM (U87) or DMEM (A172, NHA) supplemented with 10% FBS. piRNA mimics were purchased from IDT, and single-stranded non-targeting RNA sequences of similar size were used as negative controls in in vitro experiments (QIAGEN). For in vitro assays, cells were reverse transfected according to the manufacturer's instructions using LipofectAMINE RNAiMAX transfection reagent (Invitrogen); transfection efficiency was confirmed using siGLO fluorescent transfection control oligo (GE Dharmacon).

Measurement of piRNA Expression

Total RNA was isolated from U87, A172, and NHA cell lysates using the miRNeasy Mini Kit (QIAGEN) and cDNA was converted using the NCode miRNA First Strand cDNA Synthesis Kit (Invitrogen). qPCR was performed on an ABI-7500 System (Applied Biosystems) using a SYBR FAST qPCR Kit (Kapa Biosystems). Amplification reactions were conducted in triplicate with custom short piRNA forward primers and a universal reverse primer targeting appended poly(A) tails. Expression levels were normalized to small nuclear RNA U6 expression. Predicted secondary structures of piRNAs were generated by the Mfold v3.6 RNA folding algorithm using default parameters.

Genome-Wide Expression Profiling

U87 cells were reverse transfected with either wild-type piR-598 or a non-target control (NC) RNA. Cells were harvested 24 hours after transfection, and total RNA was isolated and approximately 1 μg was submitted to the Yale Center for Genome Analysis for genome-wide expression profiling on the Illumina HumanHT-12 v4 Expression Bead-Chip platform in biological duplicate. Genes showing expression level differences between NC- and piR-598-WT-treatments beyond a significance threshold of FDR-adjusted P=0.05 were considered to be differentially expressed. Five genes were selected for expression validation by qPCR with input normalization to GAPDH. Network and pathway analyses were conducted using Ingenuity Pathway Analysis software; P-values for affected functional pathways were calculated using a Fisher's exact test for enrichment of affected genes with a particular functional annotation. Array data have been deposited in the NCBI Gene Expression Omnibus repository (accession number GSE78935).

Cell Viability Assay

Cell viability was evaluated in piRNA-598- and negative control RNA-treated cell populations using the CellTiter 96 AQueous One Solution Cell Proliferation Assay (MTS) kit (Promega). Briefly, cell viability was quantified at 48 and 96 hours after transfection. Color development was evaluated one hour after addition of MTS using a microplate spectrophotometer at an absorbance of 490 nm. Viability differences were analyzed using a Student's t-test using six replicates per condition.

Soft Agar Colony Formation Assay

U87 cells were reverse transfected with piRNA-598 or negative control oligos. Twenty-four hours after transfection, cells were trypsinized and re-suspended in warmed EMEM with 0.36% agar. The mixture was plated in 60 mm cell culture dishes above a pre-solidified base layer of 0.75% agar. Dishes were incubated at 37° C. with the addition of 500 μL complete media every five days. After three weeks, colonies were stained with 0.04% crystal violet-2% ethanol in PBS and photographed. Colonies were counted using ImageJ v1.48 software and compared between conditions using a Student's t-test. Experiments were performed in triplicate.

Results

In order to determine whether inherited variants in piRNA-encoding sequences are associated with the risk of adult glioma development, a genetic association analysis was conducted in 1,840 subjects with newly diagnosed glioma and 2,401 cancer-free controls included in the GliomaScan consortium. Approximately 67% of cases were diagnosed with high-grade glioma (grades III or IV), the majority of whom (82%) were of the glioblastoma multiforme (GBM) subtype, and 55.2% of subjects were male.

Of 2,514 SNPs of interest in piRNA-encoding sequences, 31 (1.2%) were directly genotyped on the Illumina HumanHap660W platform, and genotypes at 1,397 (55.6%) were imputed; 1,086 SNPs (43.2%) were excluded because they were unable to be imputed with sufficiently high quality due to low array coverage in piRNA-encoding intergenic regions. In total, 1,428 SNPs were analyzed for association with glioma risk adjusting for sex, age, study design, and the first two principal components. No evidence of systematic bias from underlying population substructure or other factors was detected in the input genotype data using this model (genomic inflation factor $\lambda=1.009$).

A Manhattan plot illustrates all 1,428 piRNA SNP-glioma association test results. Analysis revealed a Bonferroni-corrected (P<0.05/1,428 SNPs=$3.50\times10^{-5}$) statistically significant association between glioma risk and rare variant rs149336947 (P=$2.34\times10^{-5}$; FDR-adjusted P=0.033), located near the 3' end of piR-2799 on chromosome 2q33.1. piR-2799 is a 30 nucleotide piRNA that maps to the fourth intron of apoptosis inhibitor CFLAR, which is widely expressed in the human body including in the brain (FIG. 2A).

Four additional modest associations of interest were observed at rs62435800 in piR-18913 on chromosome 6q27 (P=$1.13\times10^{-4}$; FDR-adjusted P=0.054), rs147061479 in piR-598 on chromosome 8q13.1 (P=$1.69\times10^{-4}$; FDR-adjusted P=0.060), rs142742690 in piR-11714 on chromosome 9q22.1 (P=$1.10\times10^{-4}$; FDR-adjusted P=0.079), and rs35712968 in piR-3266 on chromosome 10q24.2 (P=$3.11\times10^{-4}$; FDR-adjusted P=0.089) (Table 1).

TABLE 1

Top piRNA SNPs associated with glioma risk by FDR-adjusted P-value

| rsID | piRNA | Chromosome band | Host gene | MAF (%)[1] | OR (95% CI)[2] | Nominal P-value[3] | FDR-adjusted P-value |
|---|---|---|---|---|---|---|---|
| rs149336947 | piR-2799 | 2q33.1 | CFLAR | 0.8/1.6 | 2.54 (1.65-3.91) | $2.34 \times 10^{-5}$ | 0.033 |
| rs62435800 | piR-18913 | 6q27 | — | 19.6/14.7 | 0.79 (0.70-0.89) | $1.13 \times 10^{-4}$ | 0.054 |
| rs147061479 | piR-598 | 8q13.1 | — | 1.7/3.1 | 1.80 (1.33-2.46) | $1.69 \times 10^{-4}$ | 0.060 |
| rs142742690 | piR-11714 | 9q22.1 | — | 7.2/5.1 | 0.69 (0.57-0.83) | $1.10 \times 10^{-4}$ | 0.079 |
| rs35712968 | piR-3266 | 10q24.2 | HPSE2 | 4.3/3.1 | 0.64 (0.51-0.82) | $3.11 \times 10^{-4}$ | 0.089 |

[1]Minor allele frequency (controls/cases)
[2]Associations were calculated by logistic regression under an additive allelic model adjusting for sex, age, study design, and the first two principal components
[3]Bonferroni-corrected P-value was $3.50 \times 10^{-5}$ To examine these associations at higher resolution, genotypes were impute for all SNPs in 300-kb regions surrounding the five associated SNPs. For piR-2799, this analysis revealed nearly 100 SNPs with associations of comparable magnitude to that of rs149336947 spanning a ~250-kb region of linkage disequilibrium (FIGS. 2B-2F). This region contains four genes and is upstream of one gene. In contrast, clusters of SNPs showing enhanced association signals were observed in more narrow regions of linkage disequilibrium surrounding rs62435800 in piR-18913, rs147061479 in piR-598, rs142742690 in piR-11714, and rs35712968 in piR-3266. Both piR-18913 and piR-598 map to genetic regions that encode a small number of piRNAs and are devoid of protein-coding genes. piR-11714 is located on a piRNA-dense haplotype that does not encode protein-coding genes and is ~50 kb upstream of SPIN1, and piR-3266 maps to the 3'UTR of HPSE2.

piRNA expression measurement was conducted using a qPCR-based method. Results showed expression of piR-18913, piR-598, piR-11714, and piR-3266 in all cell lines tested (U87, A172 and NHA). Expression of piR-2799 was not detected in any of the cell lines.

Figure 3A:
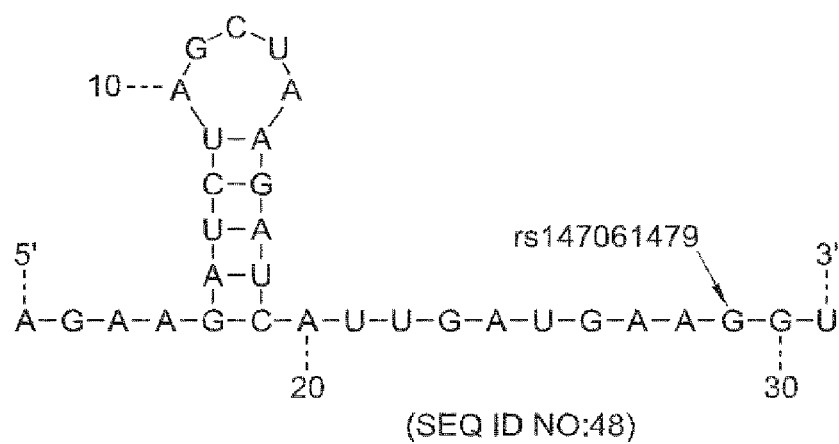
FIGS. 3A-3C illustrate the structure and transcriptional impact or piR-598.

Among the four candidate piRNAs (piR-18913, piR-598, piR-11714, and piR-3266) that were found to be expressed in the cell lines examined, piR-598 harbored the variant conferring the greatest magnitude of glioma risk or protection and therefore was the subject of additional in vitro functional analyses. The predicted secondary structure of piR-598 is illustrated in FIG. 3A. In the most thermodynamically stable structure, the piRNA forms a small hairpin loop from the 5th to 19th bases; variant rs147061479, located at the 29th of 31 bases, is not involved in the predicted loop structure. Transcriptome-wide expression profiling 24 hours was performed after transient upregulation of the piRNA in U87 cells to examine the impact of the expression of this piRNA in the context of glioma. Relative to non-targeting control-treated cells, a total of 518 transcripts were observed to be differentially expressed at FDR-adjusted P<0.05, the majority of which (71.2%) were observed to be underexpressed in piR-598-treated cell. Expression differences for five transcripts selected for validation of expression array data by qPCR were generally consistent with array results.

Figure 3B:
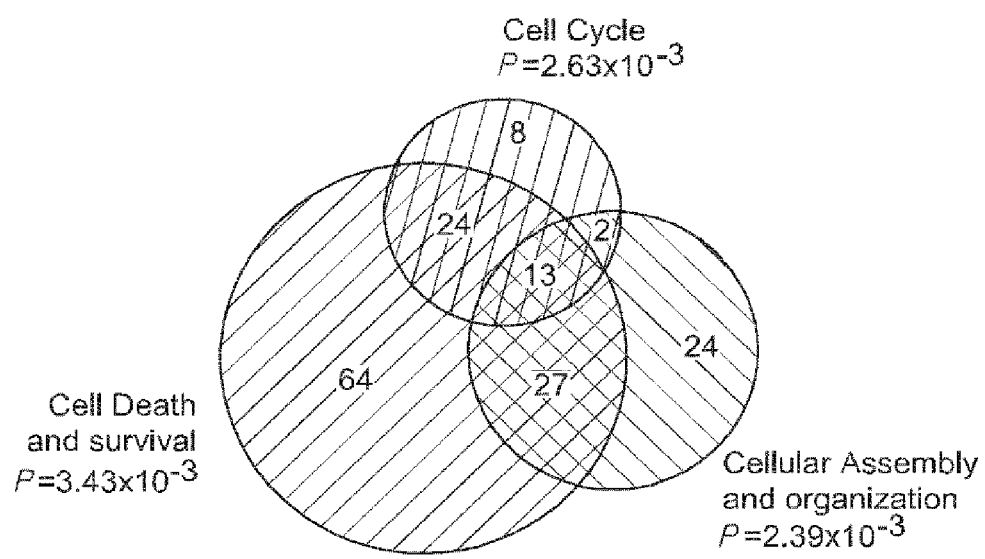
Figure 3C:
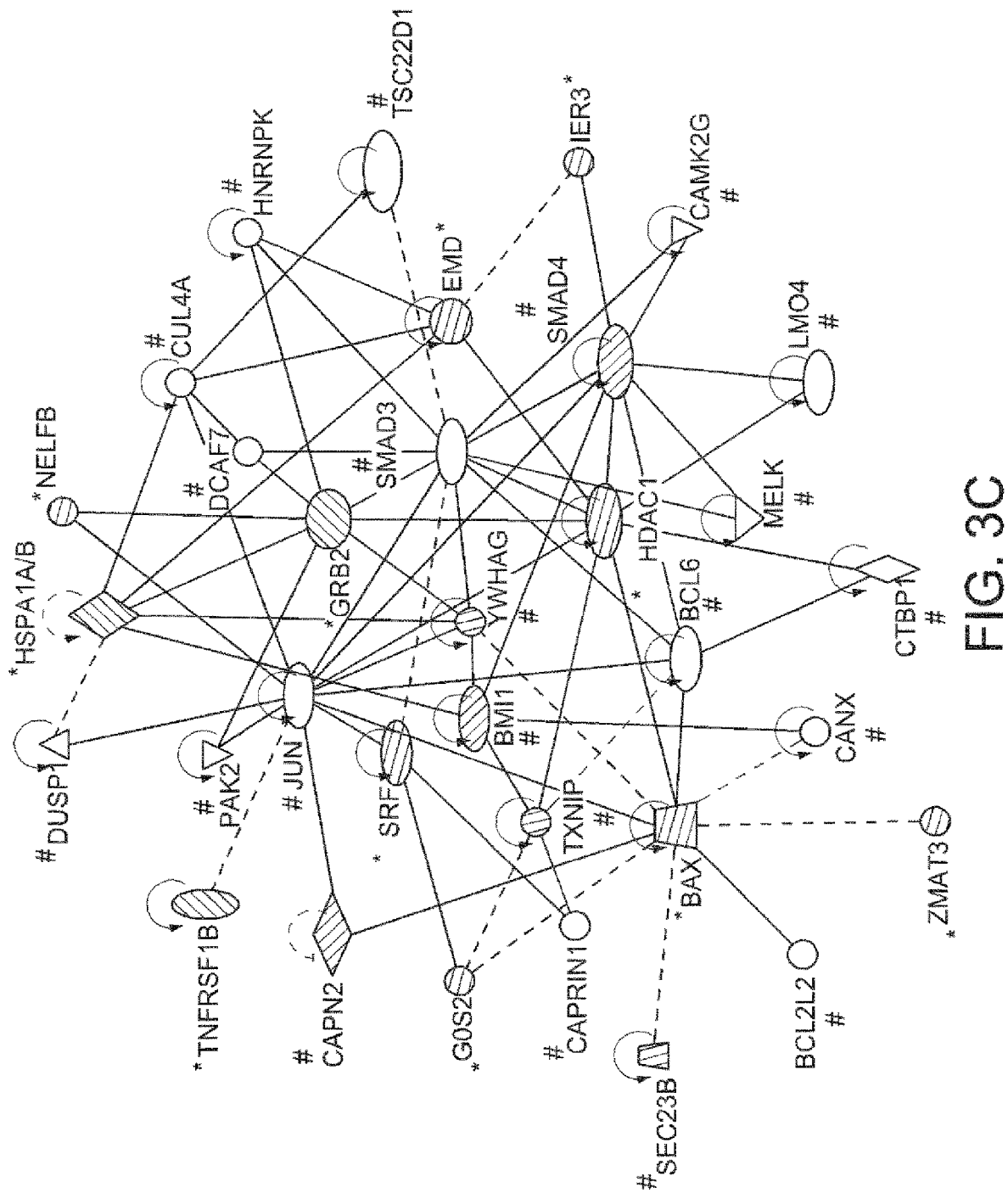

Subsequent Ingenuity Pathway Analysis showed that piR-598-affected genes were significantly enriched for those involved in cell death and survival ($P=3.43\times10^{-3}$), cell cycle progression ($P=2.63\times10^{-3}$), and cellular assembly and organization ($P=2.39\times10^{-3}$) (FIG. 3B). Network visualization analysis revealed a core of functionally interrelated molecules including BAX, a key regulator of p53-mediated apoptosis, and oncogenic transcription factor JUN (FIG. 3C).

Figure 4A:
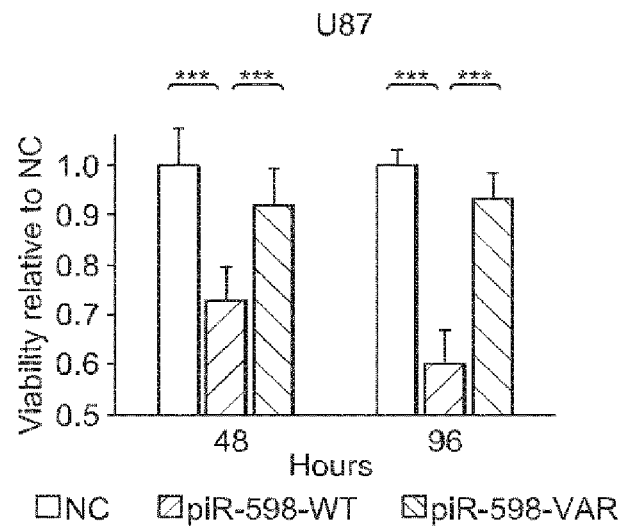
FIGS. 4A-4D are bar graphs illustrating glial cell viability and soft agar colony formation following wild-type (WT) or variant (V) piR-598 treatment.
Figure 4B:
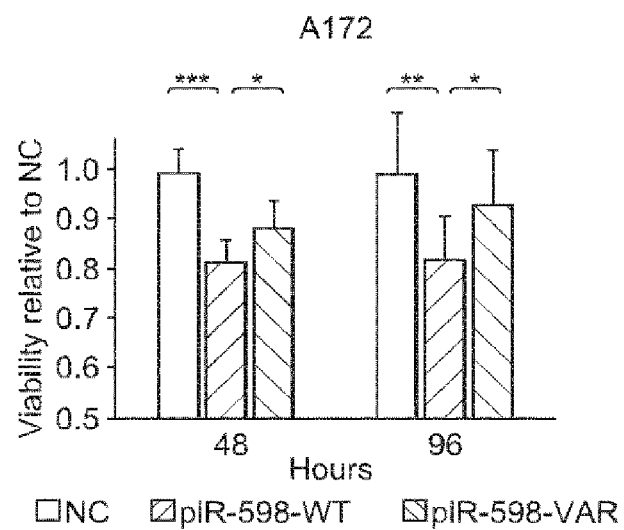
Figure 4C:
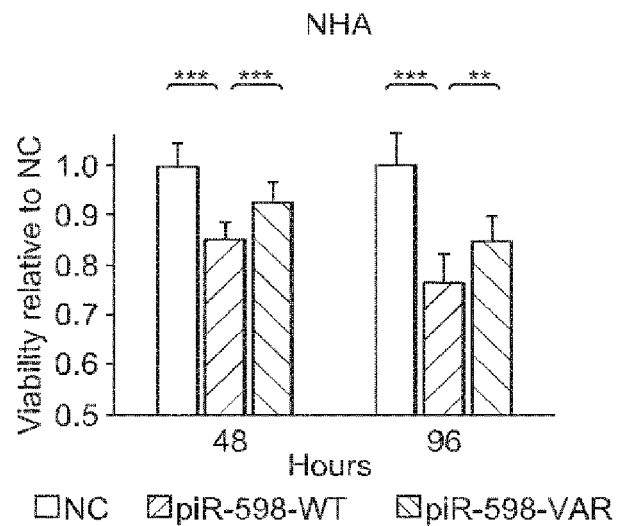

Wild-type and variant piR-598 mimics were independently overexpressed in glioma (U87 and A172) and normal human astrocyte (NHA) cell lines, and cell viability was measured. Relative to a non-targeting control RNA, transfection of wild type piR-598 sharply reduced proliferation of both U87 and A172 cells, notably with nearly 40% inhibition measured 96 hours after transfection in U87. However, transfection of the mutant rather than wild-type piR-598, containing the variant allele, significantly attenuated the anti-proliferative impact. The same pattern was observed in normal glial cell line NHA (FIG. 4A-4C).

Figure 4D:
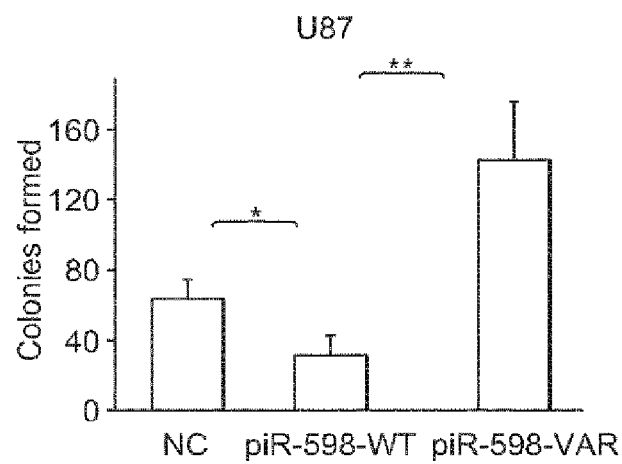

The functional impact of the piRNA variant was also examined on U87 colony formation in soft agar, which is a model of anchorage-independent growth potential. Treatment with wild-type piR-598 reduced the number of colonies formed to approximately half those formed following negative control treatment. However, treatment with the variant rather than wild-type piRNA was sufficient to not only eliminate the anti-proliferative effect of the piRNA, but to confer a more than four-fold increased colony forming potential relative to wild-type piR-598 treatment (FIG. 4D).

This post-GWAS study indicates that inherited variants at five piRNA loci (FDR-adjusted P<0.10) are associated with glioma risk in the GliomaScan Cohort, the largest publicly available glioma GWAS dataset. None of these associations has been reported in previous publications. Genomic loci at 8q24 and 9p21 have been linked to glioma in previous GWAS (38, 39); however, observed associations on these chromosomes at rs147061479 (piRNA-598 at 8q13) and rs142742690 (piRNA-1714 at 9q22) are unrelated to previous signals indicating genetic risk loci harboring piRNA variants have been identified from the post-GWAS approach.

A Bonferroni-adjusted significant association was detected between glioma risk and rs149336947 in piR-2799. Regional imputation showed that this association extended over a large region of linkage disequilibrium that harbors four genes including apoptosis regulator CFLAR as well as the promoter region for initiator caspases CASP10 and CASP8 that has been linked to susceptibility to several cancers. Thus, the association at rs149336947 may reflect a functional polymorphism that is unrelated to piR-2799, possibly representing a separate low-frequency biomarker of glioma risk that is itself worthy of further follow-up. The observation that piR-2799 expression was undetectable in U87, A172, or NHA cell lines further supports this notion.

In contrast, regional imputation of the other four regions harboring piRNAs piR-18913, piR-598, piR-11714, and piR-3266 revealed narrow clusters of SNPs with amplified association signals relative to surrounding areas. There are no protein-coding genes in the regions that encode piR-598, piR-18913 and piR-11714. Moreover, expressions of all four of these piRNAs were detectable in both normal glial- and glioma-cell lines. These findings indicate potential biological roles of these piRNAs and their variants in gliomagenesis that warrants further examination.

The functional significance of one of the identified piRNAs, piR-598, was explored in follow-up transcriptional profiling and network analyses, which indicated involvement of this piRNA in cell death and survival pathways. Of particular interest was the upregulated expression of the BAX transcript, which encodes a protein that promotes cell death by inhibiting apoptosis repressor Bcl-2. Expression of the closely related GOS2 gene, encoding another Bcl-2-interacting and apoptosis-promoting protein, was upregulated, as was HDAC1, which has been shown to induce BAX expression. Expression profiling was performed after a relatively short treatment period (24 hours) in order to detect early piRNA-induced transcriptional changes before cell viability was compromised; gene expression differences in this experiment did not tend to be large in magnitude as a result.

Subsequent in vitro assays confirmed the role of piR-598 in cellular growth identified from the expression profiling analysis, and further demonstrated the functional impact of the genetic variant. Delivery of the wild-type piRNA-598 mimic significantly diminished cell viability relative to control treatment. However, upregulation of the variant rather than wild-type piR-598 sharply attenuated the anti-proliferative response observed with the wild-type piRNA. Additional evidence comes from the observation that wild-type piR-598 treatment limited long-term colony formation of U87 cells seeded in soft-agar, yet treatment instead with the variant piRNA was sufficient to eliminate the anti-proliferative effect of piR-598 and in fact promoted colony formation. The discrepancy in the effect of the variant piRNA with respect to negative control treatment in the two assays was likely attributable to the difference in time period of cell growth after piRNA treatment (4 vs. 21 days), as an increased growth rate attributable to the variant piRNA was more readily revealed via the greater number of population doublings occurring in the longer-term colony formation assay. These results provide consistent functional support for the increased glioma risk associated with rs147061479.

Example 2: Glioma-Related piRNAs Identified by Expression Profiling Analysis

The PIWI-piRNA pathway has been demonstrated to play a highly conserved regulatory role in transposon suppression in germline stem cells. While its significance outside of this context remains largely enigmatic, there has been striking consistency in findings that PIWI-family proteins are ectopically expressed and associated with worse outcomes across a wide array of cancer types, and more recently that piRNAs are expressed in tumor type-specific patterns that differ markedly from corresponding normal tissues. However, no information has been reported to date on the nature of piRNA expression in many cancer types, including glioma, and the functional implications of dysregulated piRNA expression are largely unelucidated. The results in the following examples demonstrate that a subset of piRNAs are expressed in neuroglial tissue including some that are differentially expressed in GBM relative to normal brain tissue. The data further demonstrate that several tumor-underexpressed piRNAs show an anti-proliferative effect when transfected into GBM cell lines.

Materials and Methods

In order to examine piRNA expression levels and differences in GBM and the normal brain, seven pairs of GBM and normal brain tissue specimens were profiled for expression of 23,677 piRNAs using the ArrayStar hg19 piRNA microarray.

Study Specimens and Processing

Formalin-fixed paraffin-embedded (FFPE) primary GBM (n=7) and normal brain specimens (n=7; specimens collected post-mortem or from resection for epileptic management), matched by age, race, and gender, were purchased from the Cooperative Human Tissue Network. The study was approved by the institutional review board (IRB) of Yale University (HIC Protocol #: 1212011202) and written informed consent was received from participants. Subjects providing tumor specimens had not undergone radio- or chemotherapy at the time of resection. RNA was isolated from sections corresponding to approximately 8-10 mg of tissue from each specimen using the AllPrep DNA/RNA FFPE Kit (QIAGEN).

piRNA Expression Profiling

Total RNA was pooled in equal proportions by tissue type (tumor and normal) and samples were submitted to ArrayStar facilities for piRNA expression profiling in duplicate using the ArrayStar Human 4×44K piRNA Expression Array, which includes probes for 23,677 mature human piRNAs. Data were quantile normalized with Agilent GeneSpring GX 12.1 software and have been deposited to the Gene Expression Omnibus repository (GSE79438). piRNAs with signal intensity >2,000 were considered to be expressed and differences between sample types were calculated to assess biologically significant changes.

Cell Lines and Reagents

Glioma cell lines U87 and A172, purchased from ATCC, and immortalized normal human astrocytes (NHA), purchased from the University of California, San Francisco Tissue Core, were maintained in EMEM (U87) or DMEM (A172, NHA) supplemented with 10% FBS. All ATCC cell lines are tested for contaminants and authenticated prior to shipment; cells were not re-authenticated as they were passaged in for fewer than 6 months after resuscitation. piRNA mimics were purchased from IDT (Table 2), and single-stranded non-targeting RNA sequences of similar size were used as negative control. For in vitro assays, cells were reverse transfected according to the manufacturer's instructions using LipofectAMINE RNAiMAX transfection reagent (Invitrogen); transfection efficiency was confirmed using siGLO fluorescent transfection control oligo (GE Dharmacon).

Confirmation of piRNA Expression piR-8041 expression was quantified in individual patient specimens and U87, A172, and NHA total RNA by qPCR with locked nucleic acid probes for enhanced specificity and sensitivity. Briefly, RNA was reverse transcribed using an Exiqon Universal cDNA Synthesis Kit and targets were amplified in triplicate using custom piR-8041 primers with the ExiLENT SYBR Green PCR Kit (Exiqon) with normalization to small nuclear RNA U6 expression. Northern blotting was also performed.

piRNA-Induced Host Gene Expression and Methylation

Gene expression and DNA methylation of piR-8041 host gene SAPS2 were measured using U87 RNA and DNA, respectively, 48 hours after transfection with piR-8041 or negative control. Gene expression was measured by qPCR in triplicate with normalization to GAPDH. DNA methylation was evaluated by MS-PCR in the SAPS2 exon to which piR-8041 maps as well as an intronic CpG island that is approximately 1 kb downstream.

Results

Differentially Expressed piRNAs in GBM Tissue Specimens

Figure 5B:
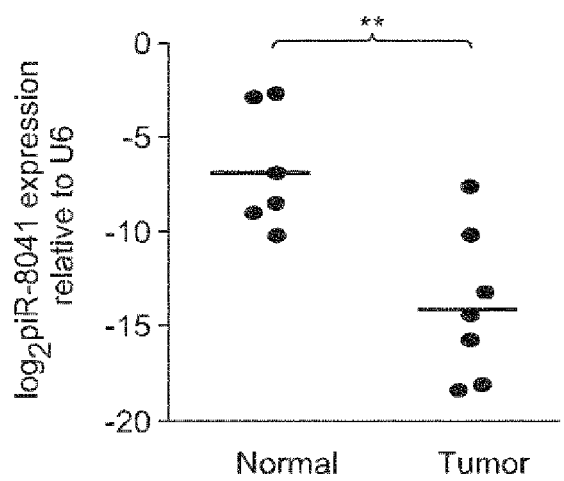
FIG. 5B is a dot plot showing validation of piR-8041 expression levels in individual normal vs. tumor tissue specimens by qPCR (piR-8041 expression relative to U6 (normal) and tumor cells). Data are presented as $\log_2$ (piR-8041 expression level) relative to small RNA U6 expression; lines denote mean expression level by tissue type.
Figure 5C:
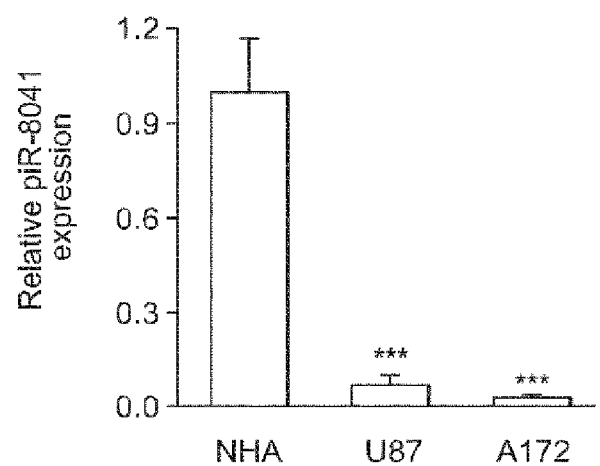
FIG. 5C is a bar graph showing measurement of piR-8041 expression in normal human astrocytes (NHA) and glioma cell lines U87 and A172 by qPCR. Expression levels from qPCR measurements were analyzed by Student's t-test for normal vs. tumor specimens and U87 and A172 cell lines relative to NHA. , P<0.01; *, P<0.001; error bars denote standard deviation of triplicate measurements.

Following array-based piRNA profiling, 353 piRNAs were observed to be expressed in both normal and tumor tissue (FIG. 5A). Expression differences of at least two-fold between comparison groups were observed for 145 piRNAs (Table 3). Among these differentially expressed piRNAs were two that have been previously found to be dysregulated in cancer, piR-651 and piR-823. Of particular interest was 10.3-fold GBM-underexpressed piR-8041, which is a 26-nt piRNA encoded by the $12^{th}$ exon of protein-coding gene SAPS2 on chromosome 22. The expression difference observed by array profiling was confirmed in individual samples by qPCR using a LNA probe (FIG. 5B). In agreement with the observation in clinical specimens, piR-8041 was found to be approximately 15- and 35-fold underexpressed in two GBM cell lines, U87 and A172, respectively, relative to NHA cells (FIG. 5C). piR-8041 expression was not detectable by northern blot in these cell lines.

Additionally, SAPS2 mRNA expression was measured to determine whether piR-8041 acts in cis to regulate host gene SAPS2 and observed a 4-fold reduction following piR-8041 upregulation. However, methylation levels at two CpG islands in proximity to the piR-8041 complementary sequence were found to be high and unchanged following piR-8041 transfection.

Example 3: In Vitro Anti-Tumor Effects of Identified piRNAs from Expression Analysis Materials and Methods Cell Viability and Soft Agar Assays For cell viability, cells were reverse transfected with piRNA or negative control oligos and color development was evaluated one hour after addition of MTS (Promega) using a microplate spectrophotometer. For soft agar assays, cells were reverse transfected with piRNA or negative control oligos. After 24 hours, cells were re-suspended in warmed culture medium with 0.36% agar and seeded in 60 mm dishes above a base layer of 0.75% agar. Colonies were stained with 0.04% crystal violet-2% ethanol in PBS after three weeks and counted using ImageJ v1.48 software. Experiments were performed in triplicate and differences of viability and colony number were analyzed using a Student's t-test.

Genome-Wide Transcriptome Profiling

RNA profiling of piR-8041- or control RNA-transfected U87 cells, 24 hours post-transfection, was performed on the Illumina HumanHT-12 v4 Expression BeadChip platform in biological duplicate. Genes with expression differences ≥|1.2|-fold and beyond a significance threshold of FDR-adjusted P=0.05 were considered to be differentially expressed, and 5 genes were selected for expression validation by qPCR with input normalization to GAPDH. Ingenuity Pathway Analysis software was used to perform network analyses and identify affected functional pathways using a Fisher's exact test for enrichment of genes with a specific functional annotation. Expression array data have been deposited to the Gene Expression Omnibus repository (GSE79438).

Cell Cycle and Apoptosis Assays

For cell cycle analyses, cells were fixed in 70% ethanol, washed, and incubated with RNase A (100 µg/ml) followed by propidium iodide (PI) (40 µg/ml) in PBS. Cells were then analyzed on a BD FACSCalibur flow cytometer, and G0/G1, S, and G2/M fractions were determined using FlowJo software v10. For apoptosis assays, cells were prepared using the Dead Cell Apoptosis Kit with Annexin V FITC and PI (ThermoFisher Scientific) according to the manufacturer's instructions. Cells were analyzed for Annexin V staining and PI exclusion using a BD Accuri C6 flow cytometer and accompanying software. Differences in apoptotic and cell cycle distributions were analyzed by Student's t-test for triplicate experiments.

Cell Invasion and Migration Assays

For cell invasion assays, piR-8041 or negative control-transfected cells were transferred to the top chamber of a BioCoat Matrigel Invasion Chamber (BD Biosciences) in serum-free media 48-hours post-transfection. After 24 hours, invading cells were fixed and stained, then counted using an Olympus BX51 microscope with a QImaging CCD digital camera. For cell migration assays, cells were reverse transfected in collagen-coated 6-well plates. At 48 hours post-transfection, a scratch was made using a sterile pipette tip and photographs were taken in three separate fields for each condition at baseline, 6 hours, and 12 hours post-scratch. The gap width was measured to calculate the closure percentage relative to baseline. Experiments were performed in triplicate. A two-sided Student's t-test was used to compare mean counts of invaded cells and mean closure percentages between piRNA-treated and control conditions in cell invasion and migration assays, respectively.

Restored Expression of GBM-Underexprssed piRNAs Reduces GBM Cell Proliferation

Figure 6A:
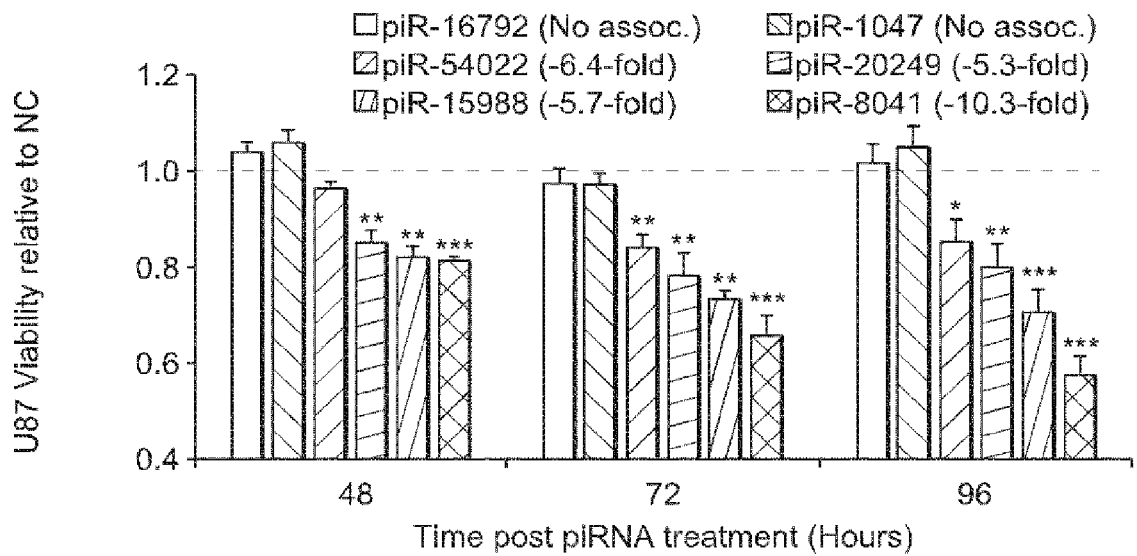
FIGS. 6A-6D are bar graphs showing piR-8041 and other GBM-underexpressed piRNAs reduce GBM cell proliferation.

To explore the biological significance of the findings, the impact on U87 cell proliferation was measured following exogenous overexpression of piR-8041 and other GBM-underexpressed piRNAs. More than a 30% reduction in cell population viability was observed 96 hours after piR-8041 transfection. The effect on cell viability of treatment with three other underexpressed piRNAs (piR-54022, piR-20249, and piR-15988) was also examined, and it was found that delivery of these piRNAs also reduced viability of U87 cells, though to a lesser degree than piR-8041. Notably, delivery of two piRNAs that were expressed to an equivalent degree between tumor and normal specimens (piR-16792 and piR-1047) did not significantly affect the viability of U87 cell populations (FIG. 6A).

Figure 6B:
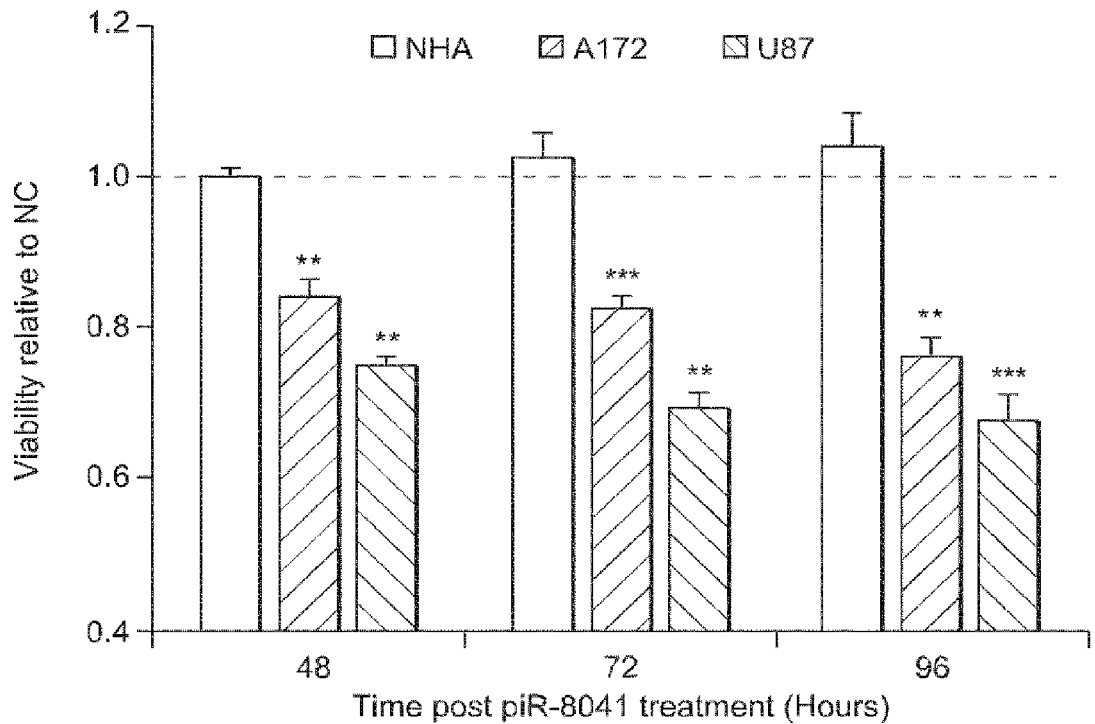
Figure 6C:
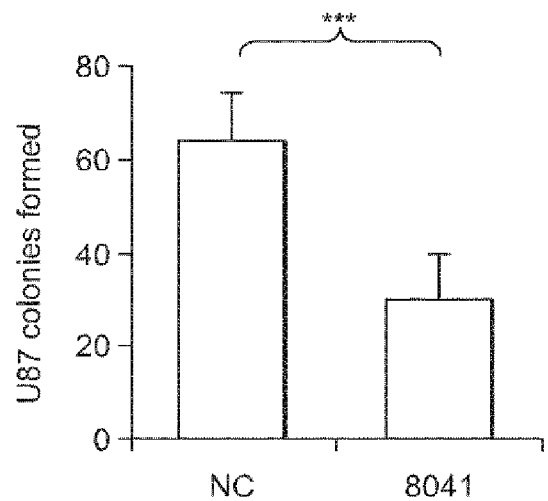
Figure 6D:
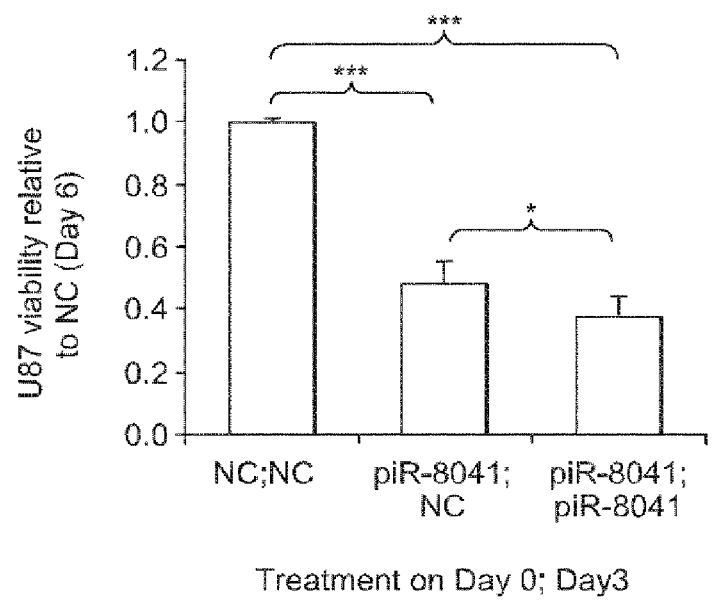
Figure 7A:
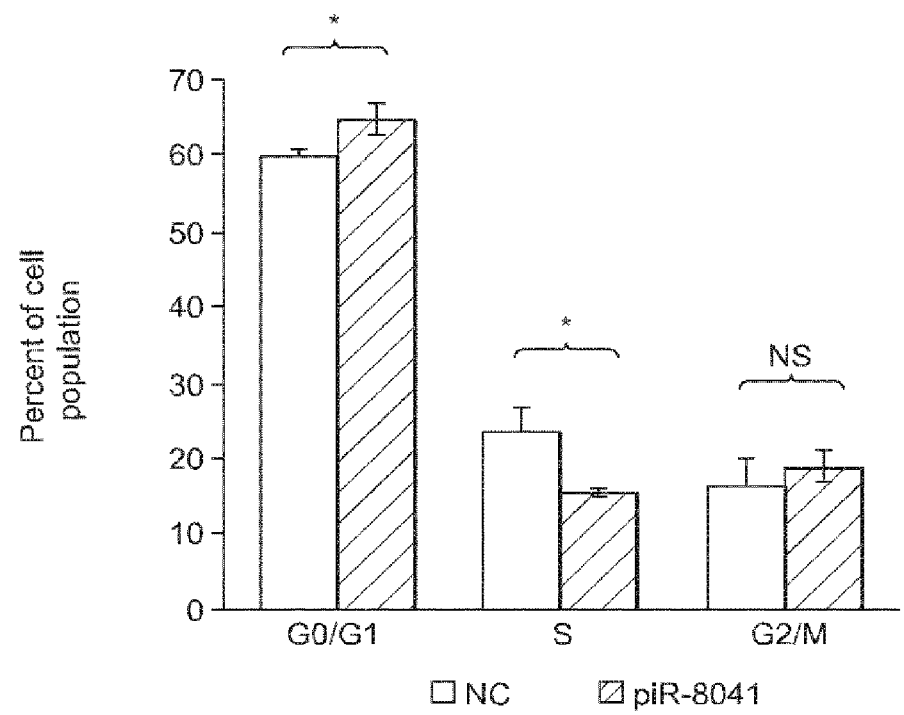
FIGS. 7A-7B show that piR-8041 inhibits cell cycle progression and induces apoptosis.
Figure 7B:
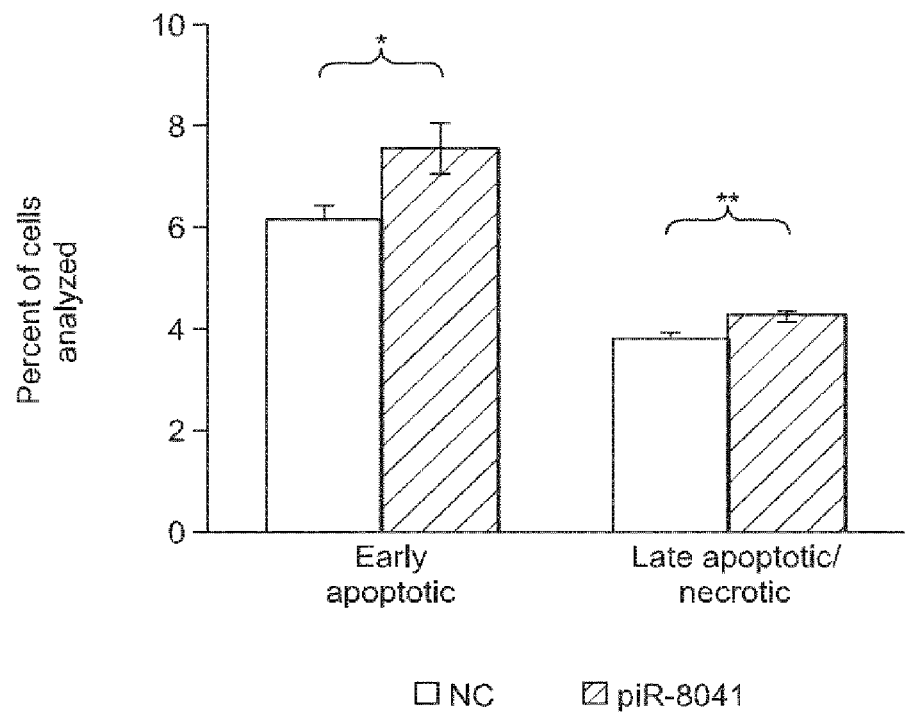

Experiments using two other glial cell lines indicated that piR-8041 also inhibited cell proliferation of glioma cell line A172, yet did not affect proliferation of normal human astrocytes (NHA) (FIG. 6B). Additionally, soft agar assays were performed to examine the effect of piR-8041 treatment on long-term U87 colony formation. Consistently, piR-8041 treatment significantly reduced the number of colonies (>50%) formed after three weeks (FIG. 6C). The effect of treating U87 cells a second time with piR-8041 three days after the initial transfection was also examined. U87 viability six days after the initial transfection was less than 40% of control-treated cell viability, and statistically significantly less than for cells treated only once. (FIG. 6D).

piR-8041 Overexpression Induces Cell Cycle Arrest and Apoptosis but does not Affect Invasion or Migration of GBM Cells To investigate the potential anti-proliferative mechanism of piR-8041 treatment, cell cycle and apoptosis assays were performed. DNA content analysis revealed an accumulation of U87 cells at the $G_0/G_1$ checkpoint and a concomitant decrease of the S-phase fraction 48 hours after piR-8041 treatment (FIG. 7A). No difference was observed in the proportion of cells in $G_2/M$. Additionally, piR-8041 treatment was found to induce statistically significant increases in the proportion of early apoptotic and late apoptotic/necrotic cells (FIG. 7B). However, it was observed that U87 and A172 cells were comparably invasive following piR-8041 or control oligo treatment. The migratory ability of GBM cells was also unaffected by piR-8041 treatment, as demonstrated by comparable wound-closure rates on a collagen-coated surface in both U87 and A172 cell lines.

piR-8041 Induces Transcriptional Changes in Cell Stress and Survival Pathways

To characterize the cellular response to piR-8041 treatment, genome-wide transcriptional profiling of piR-8041-exposed U87 cells was performed. The analysis yielded 214 transcripts that were differentially expressed; 108 were upregulated and 106 were downregulated in piR-8041-treated cells. Gene expression changes measured by qPCR for five top differentially expressed transcripts were found to be consistent with array results.

Figure 8A:
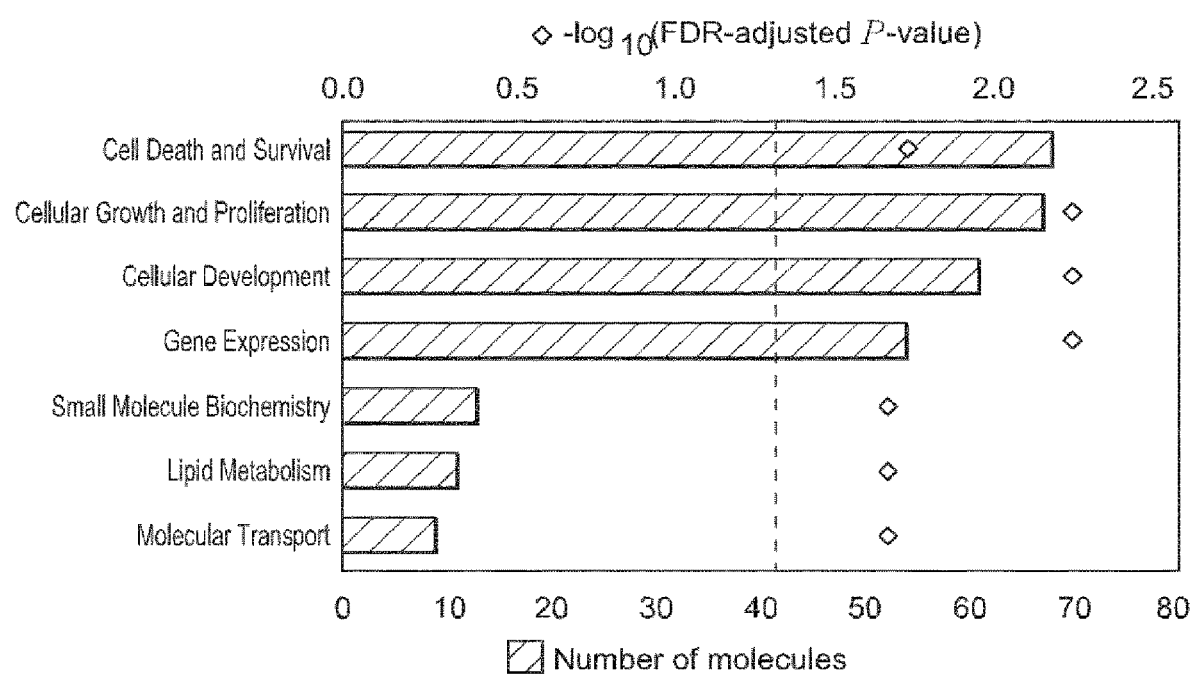
FIG. 8A is a histogram showing that piR-8041 upregulation impacts expression of genes related to protein synthesis, cellular survival, and other glioma-relevant functions. The listed biological functions are statistically significantly enriched among genes differentially expressed by piR-8041 upregulation in U87 cells after adjustment for multiple comparisons, according to Ingenuity Pathway Analysis. Bars indicate the number of genes impacted with a particular functional annotation; diamonds denote the log-transformed FDR-adjusted P-values (dotted line indicates an FDR-adjusted P-value of 0.05).
Figure 8B:
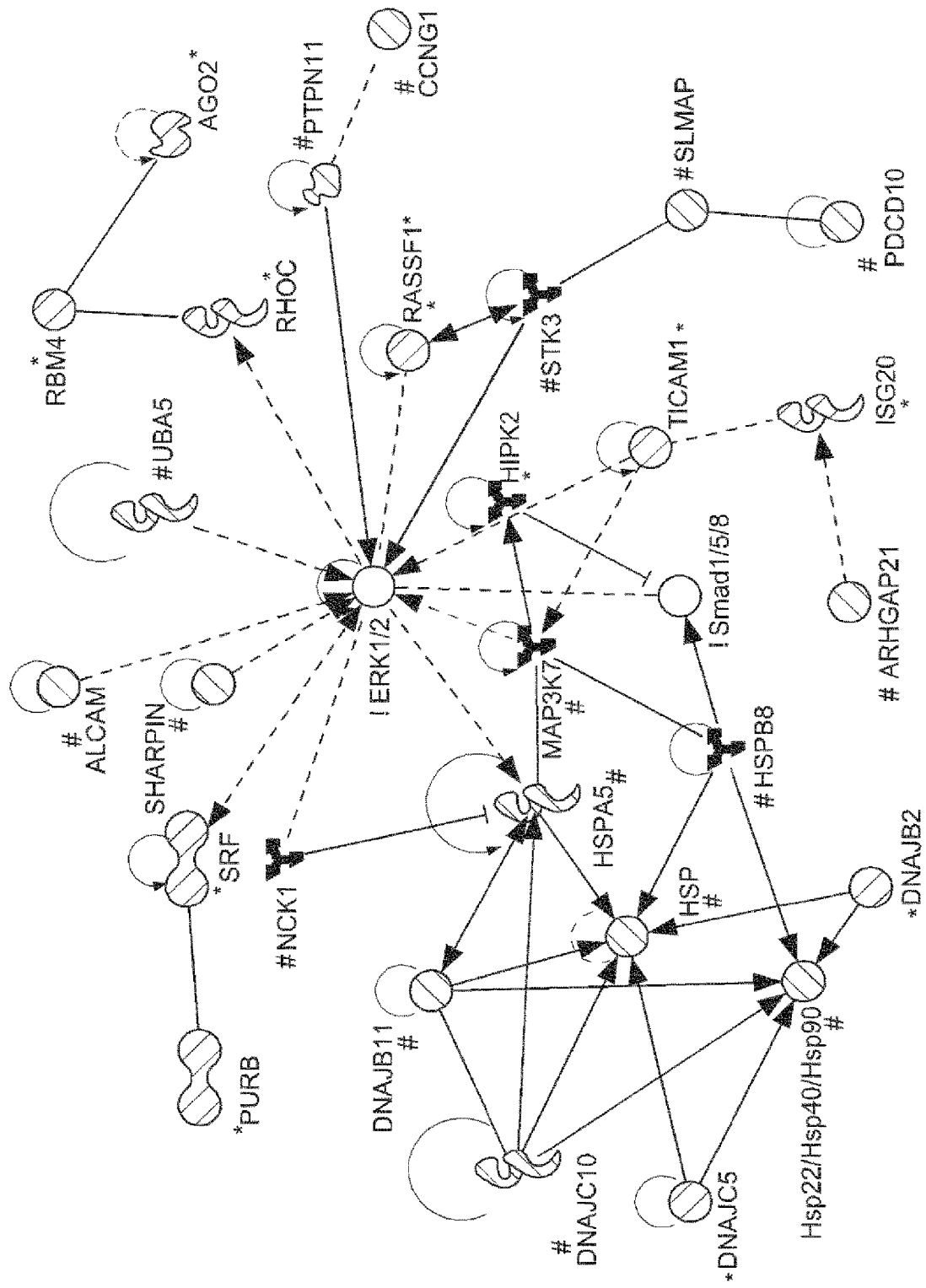
FIG. 8B is an illustration of top network of differentially expressed transcripts, related to "decreased cell viability of connective tissue cells" and "decreased synthesis of protein" following piR-8041 treatment of U87 cells. Shading denote transcript over-expression (noted by "*") and under-expression (noted by "#") relative to negative control after piR-8041 upregulation with color intensity corresponding to degree of change, and ("!") denotes predicted signaling pathway inhibition. Solid lines and dotted lines indicate direct and indirect relationships, respectively.

According to Ingenuity Pathway Analysis, piR-8041-affected transcripts were statistically significantly enriched, after adjustment for multiple comparisons, in seven major functional categories including cell death and survival, cellular growth and proliferation, and cellular development (FIG. 8A), and transcriptional changes were predicted to be consistent with "decreased cell viability of connective tissue cells" and "decreased synthesis of protein." Network analyses indicated that several members of the heat shock protein and related DNAJ Protein chaperone families were suppressed following piR-8041 treatment, as were several transcripts encoding MAPK/ERK signaling pathway proteins, indicating transcriptional impact on cellular stress and survival pathways (FIG. 8B).

Additionally, SAPS2 mRNA expression was measured to determine whether piR-8041 acts in cis to regulate host gene SAPS2 and observed a 4-fold reduction following piR-8041 upregulation. However, methylation levels at two CpG islands in proximity to the piR-8041 complementary sequence were found to be high and unchanged following piR-8041 transfection.

Example 4: In Vivo Anti-Tumor Effects of Identified piR-8041

Materials and Methods

The impact of piR-8041 transfection on U87 tumor progression in vivo was measured. U87 luc cells were transfected with piR-8041 using lipofectamine. Control U87 luc cells were transfected with non-targeting control RNA. Two days after transfection, $5\times10^4$ cells were administrated to the mouse brain. The development of U87 gliomas was monitored using an IVIS SpectrumCT Imaging System (PerkinElmer) following intravitreal luciferin injection. The tumor volumes were quantified based on the luminescence intensity.

Nude mice (n=9 per group) were anesthetized and placed in a stereotactic frame, and an incision was made and a hole drilled above the right striatum. Approximately $5\times10^4$ luciferase-expressing U87 cells suspended in phosphate buffered saline, transfected 24 hours prior to surgery with piR-8041 or control RNA, were injected into the brain and the hole was closed with bone wax and the scalp closed with surgical staples. Following surgery, tumors were imaged using an IVIS SpectrumCT Imaging System (PerkinElmer) following intravitreal luciferin injection, and bioluminescent intensity was measured and compared at each time point by Student's t-test. Mice were sacrificed when ethically necessary due to clinical symptoms or substantial loss in body weight. All animal work was approved by the Yale University Institutional Animal Care and Use Committee (IACUC).

Results

In Vivo Tumor Growth is Temporarily Restricted Following piR-8041 Treatment

Figure 9A:
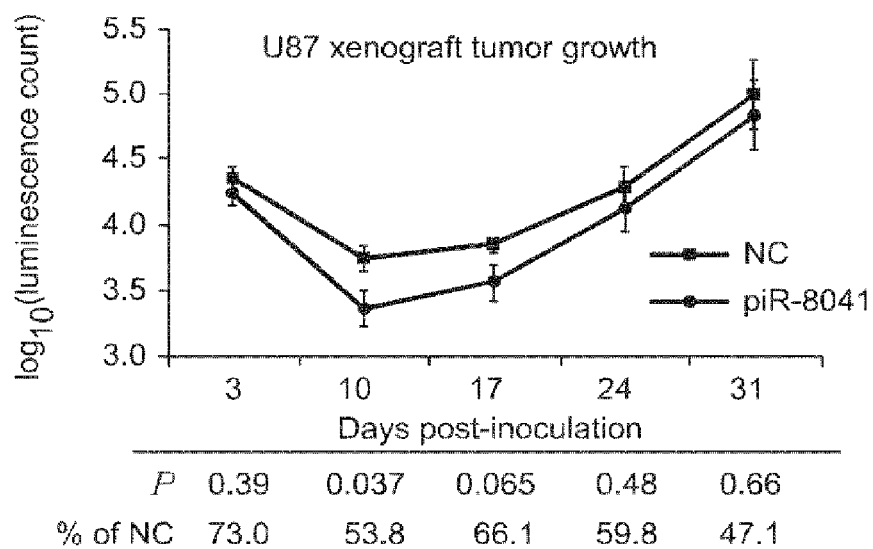
FIG. 9A is a line graph of luminescence over days (0 to 31) of xenograft tumor growth in a U87-luciferase (LUC) model treated with either piRNA-8041 or control normal cell RNA. Bioluminescence measurements of luciferase-expressing intracranial tumors at multiple timepoints. P-values are presented along with average piR-8041-treated tumor intensity as a percentage of control intensity. piR-8041 significantly reduces U87 cell growth by nearly 50% 10 days after treatment in an orthotopic xenograft model.
Figure 9B:
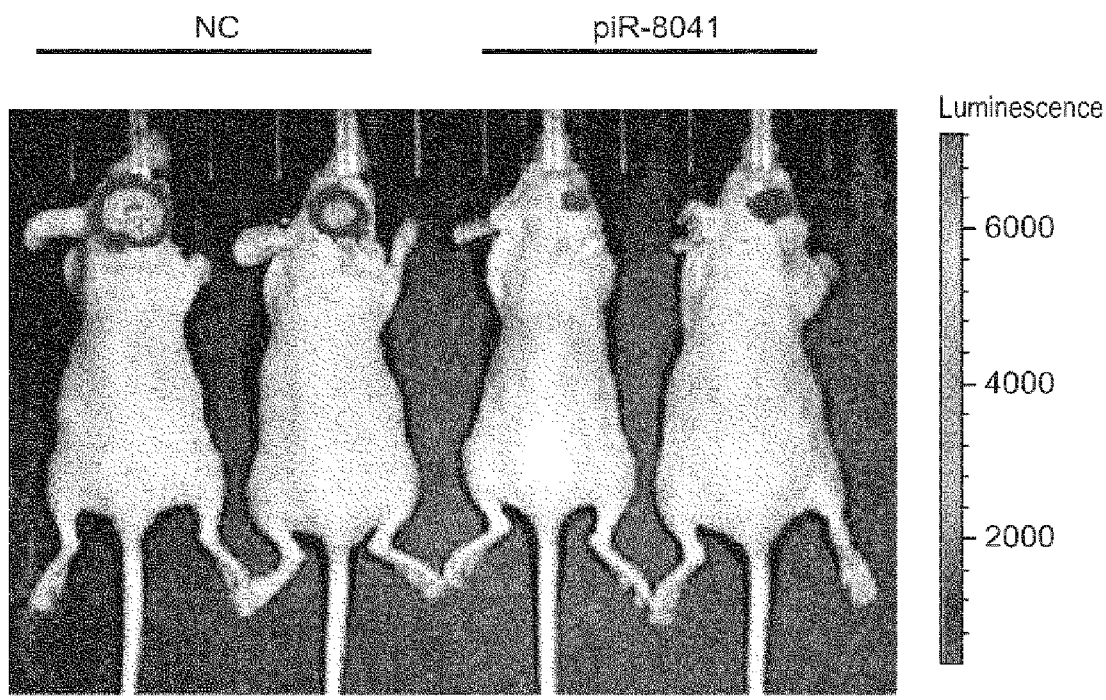
FIG. 9B shows images of representative mice from each treatment group on day 10 after tumor implantation.

To evaluate the ability of piR-8041 to restrain tumor growth in vivo, tumors were seeded intracranially in nude mice following pre-implantation transfection of luciferase-expressing U87 cells with piR-8041 or negative control RNA. Tumor growth was evaluated in live animals by bioluminescence imaging at 3, 10, 17, 24, and 31 days after implantation. See FIG. 9A. Ten days after implantation, piRNA-treated tumors were nearly half the size and statistically significantly smaller than control-treated tumors, and were marginally significantly smaller on day 17 (FIG. 9B). While piRNA-treated tumors were still reduced in size during the last two weeks for which measurements were taken, these differences were less pronounced and not statistically significant, indicating a diminishing impact of a single piR-8041 treatment after approximately ten days.

piR-8041 temporarily restricts U87 cell growth in an orthotopic xenograft model. Bioluminescence measurements of luciferase-expressing intracranial tumors were made at multiple timepoints. Luminescence intensity was measured as a proxy for tumor volume using an IVIS SpectrumCT Imaging System following intravitreal luciferin injection. Statistical significance was assessed by Student's t-test between treatment conditions at each time point; and associated P-values along with average piR-8041-treated tumor intensity as a percentage of control intensity. Images of representative mice from each treatment group were made on day 10 after tumor implantation. Colors correspond to the luminescence scale presented at right, with shading representing high and low luminescence intensity, respectively. The results demonstrated that transfection with piR-8041 significantly delayed tumor progression. By the end of three weeks after inoculation, the average tumor volume in the piR-8041 transfection group was about ⅓ of that of the control-treated group, indicating piR-8041 should be useful as a therapeutic agent for brain cancer treatment.

Conclusions from Examples 2-4

Array-based piRNA expression profiling results indicated that ~350 piRNAs are expressed in both normal and GBM brain tissue. A subset of piRNAs was differentially expressed in tumor tissue, raising the possibility that specific piRNAs may be involved in the tumorigenic process. While differential piR-8041 expression was confirmed by qPCR, the piRNA could not be resolved by northern blot, highlighting the low expression level of the RNA.

In vitro analyses revealed that several piRNAs are underexpressed in GBM tissue due to their tumor-suppressive properties, as demonstrated by significant reductions in cell population viability upon piRNA mimic transfection. Notably, the observed effects of piRNA delivery were both piRNA- and cell type-specific, which can likely be attributed to differences in piRNA targets and target function, the accessibility or abundance of the targets, and/or the expression of required PIWI proteins or associated machinery. GBM-underexpressed piR-8041 was shown to have the strongest anti-proliferative effect of the piRNAs tested (over 30% inhibition of U87 96 hours post-transfection, with even greater effect after a repeated treatment), yet delivery of the piRNA did not significantly affect the proliferation of a normal human astrocyte cell line. This observation may be attributable to differences in targets or machinery as aforementioned, or to the endogenously higher baseline expression of piR-8041 in the NHA cell line, which was found to be approximately 15-fold higher than in U87. In an intracranial xenograft mouse model, pre-implantation piR-8041 treatment significantly inhibited tumor growth relative to negative control treatment for approximately 10 days, however growth subsequently accelerated. This indicates that repeated treatments will be required to sustain a tumor-suppressive dose of piR-8041, which in clinical practice will depend heavily on the availability of drug delivery vehicles that can cross the blood-brain barrier and deliver an effective dose to the tumor site.

Further functional analyses indicated that piR-8041 reduces cell proliferation primarily via induction of cell cycle arrest at the $G_1/S$ checkpoint, as well as induction of apoptosis in a small proportion of cells. This is consistent with transcriptional profiling data indicating down-regulation of ERK1/2 mitogen-activated protein kinase (MAPK) signaling, the activation of which is required for $G_1/S$-phase cell cycle progression, as well as observed transcriptional down-regulation of related MAP3K7, which encodes a TGF-β-activated kinase whose inhibition has been shown to promote apoptosis in multiple cancer types. Also consistent with the phenotypic results was the observed transcriptional upregulation of RASSF1, which encodes a tumor suppressor shown to mediate cell cycle arrest at the $G_1/S$-phase transition via inhibition of cyclin D1 accumulation and also shown to induce apoptotic cell death. Furthermore, piR-8041 transcriptionally down-regulated several members of the heat shock protein (HSP) and DNAJ protein families, which facilitate proper protein folding and transport and have been extensively linked with cell stress and tumorigenesis via promotion of cell proliferation and inhibition of death pathways; small molecule inhibitors of HSPs (specifically, HSP90) have shown promise as anticancer therapeutics due to the disrupted activity of a large number of HSP-dependent oncoproteins. Together, transcriptional profiling indicates that the anti-proliferative properties of piR-8041 may be attributed to the direct or indirect inhibition of an array of oncogenic factors.

The results indicate that multiple aberrantly expressed piRNAs may play tumor suppressive roles in tumorigenesis, and specifically that down-regulation of piR-8041 (in GBM) support tumorigenesis due to its tumor-suppressive functions in regulating cell stress and survival pathways. Other identified differentially expressed piRNAs may also play tumor-suppressive or oncogenic roles in gliomagenesis, owing to their specific regulatory targets. It should be noted that piR-8041-mediated transcriptional changes observed may have been either direct or indirect in nature, and that future work will be required to determine the direct targets and detailed mechanism of action for piR-8041 and other piRNAs in a cancer context. The finding that piR-8041 host gene SAPS2 expression is reduced after piR-8041 transfection without an appreciable change in regional DNA methylation indicates that piR-8041 may act in an siRNA-like manner to silence complementary targets, which is consistent with recent studies indicating post-transcriptional piRNA activity. However, SAPS2 itself does not have an apparent relevance to tumorigenesis and thus the tumor-suppressive effect of piR-8041 is likely mediated by the targeting of other unknown sequences of imperfect complementarity.

Taken together, the functionally-relevant dysregulation of piRNA expression in GBM identified in these studies sheds new light on the biology of tumorigenesis and indicates that restoration of normal piRNA expression levels may be a viable therapeutic strategy, in a manner analogous to "microRNA replacement therapy" of down-regulated tumor-suppressive microRNAs.

Example 5: piRNA Dysfunction can be Tumorigenic in Liver Cancer

Hepatocellular carcinoma (HCC), arising from human hepatocytes, accounts for the majority of liver cancers. HCC is the sixth most common cancer type worldwide and is responsible for an estimated 25,000 deaths annually in the United States. HCC is a high-mortality malignancy and has the fastest rising cancer incidence in the United States, although it occurs prevalently in sub-Saharan Africa and eastern Asia. It was reported that there was an almost three-fold increase in HCC incidence between 1975 and 2005 in the US. Main risk factors for HCC include excessive alcohol consumption, hepatitis B virus (HBV), hepatitis C virus (HCV), aflatoxin contamination of food, obesity, diabetes, and some rare inherited metabolic disorders. Patients with HCC are usually asymptomatic in the early stages of the disease, whereas it is often diagnosed at an advanced stage with poor prognosis. The molecular factors involved in HCC tumorigenesis remain unclear.

Materials and Methods

In a piRNA expression profiling analysis, 12 pairs of HCC and matching non-malignant liver specimens were compared using an ArrayStar piRNA expression microarray covering 23,000 human piRNAs. Methods of functional assays are the same as described above.

Results

Figure 10:
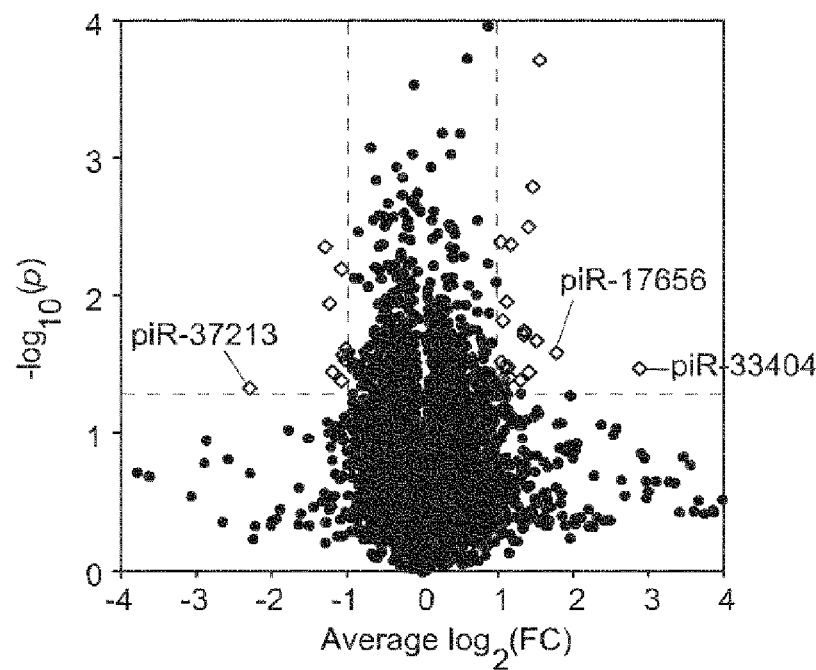
FIG. 10 is a volcano plot showing the results of piRNA expression profiling analysis for 12 pairs of liver cancer and matching non-malignant liver specimens using an ArrayStar piRNA expression microarray covering 23,000 human piRNAs. Dashed lines denote 2-fold differential expression between tumor and normal samples along the x-axis, and a significance threshold of P=0.05 along the y-axis. Dots in the top left and top right sections indicate piRNAs that exceed both of these thresholds (n=31 piRNAs). Of particular interest are three piRNAs, piR-37213, piR-17656 and piR33404 (labeled on the figure) that were ≥3-fold statistically significantly differentially expressed.

The results of the piRNA expression profiling analysis is illustrated in a volcano plot (FIG. 10). Dashed lines denote 2-fold differential expression between tumor and normal samples along the x-axis, and a significance threshold of P=0.05 along the y-axis. Dots in the top left and top right sections indicate piRNAs that exceed both of these thresholds (n=31 piRNAs). Of particular interest were three piR-NAs, noted on the figure, that were ≥3-fold statistically significantly differentially expressed.

Figure 11A:
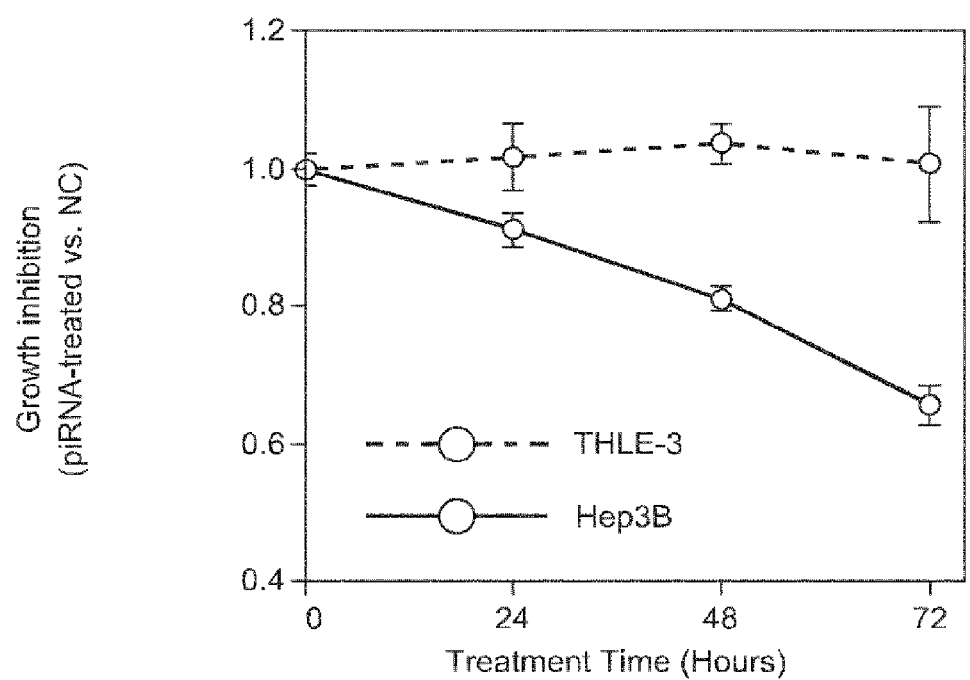
FIGS. 11A-11B show the in vitro anti-cancer effect of piR-37213. piR-37213 reduces Hep3B cell proliferation.

Among candidate piRNAs tested in vitro, the downregulated piR-37213 showed the strongest anti-cancer effect in several functional experiments. FIG. 11A shows cellular growth impact measured by Cell Proliferation Assay (MTS) in Hep3B liver tumor cells and THLE-3 normal liver cells after piR-37213 mimic transfection. Error bars represent standard error. Results showed that restoration of piRNA levels inhibited cell growth in liver cancer cells in a time-dependent manner, whereas it did not affect normal cell growth. Specifically, in piR-37213-transfected Hep3B cells, approximately 19% growth inhibition at 48 h and 35% inhibition at 72 h (P<0.01 versus NC) was observed. However, piRNAs that were not aberrantly expressed in liver tumor samples did not exhibit anti-proliferative effects when delivered.

Figure 11B:
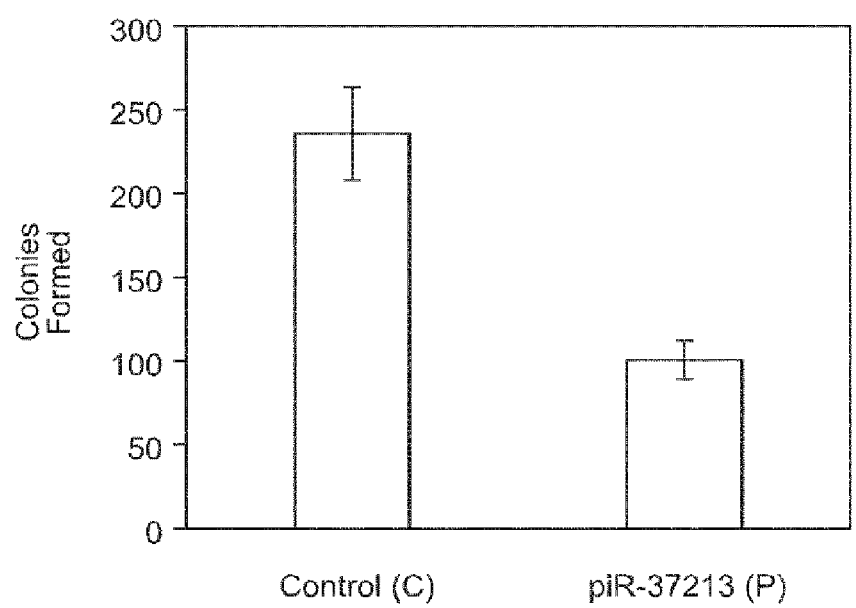

Colony formation assays were also performed to investigate the prolonged effect of restoration of HCC-associated piRNAs. Briefly, Hep3B cell colonies were stained with crystal violet 2 weeks after transfection and counted. FIG. 11B shows experimental results 2-weeks post-transfection with control small RNA (left) or piR-37213 (right) into Hep3B cells. The number of colonies in piR-37213 transfected Hep3B plates were reduced by approximately 70% relative to the number of colonies formed in control oligo treated plates (P<0.01). Similarly, soft agar assay showed that the anchorage-independent growth of Hep3B cells was reduced by about 65% after transfected with piR-37213.

Figure 12:
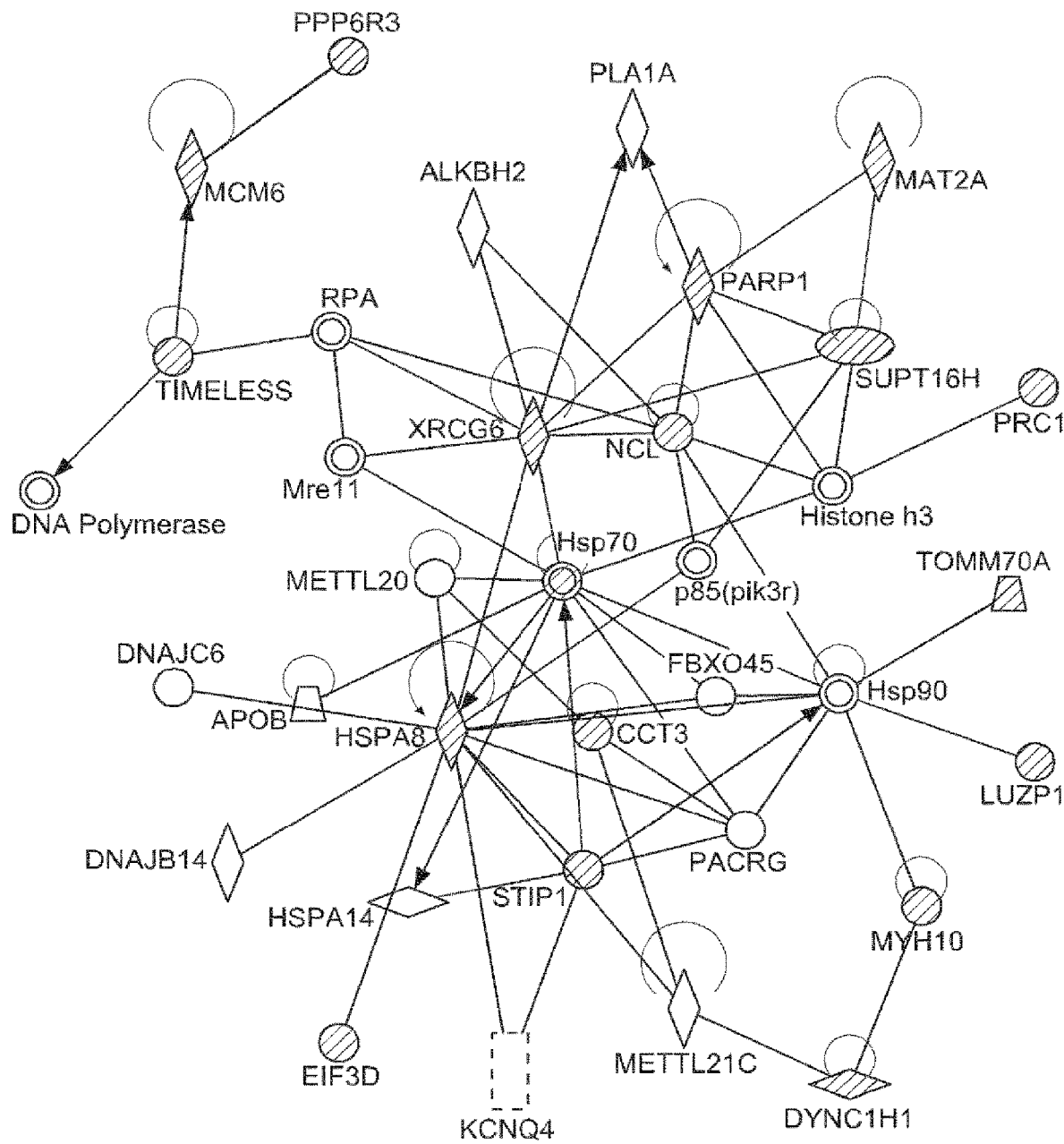
FIG. 12 is a chart showing a network of piR-37213-affected cell cycle and cell proliferation-related genes illustrates that piR-37213 induces transcriptional changes of cell cycle and cell proliferation-related genes.

Consistent with proliferation assay results, transcriptional profiling of piR-37213-treated Hep3B cells indicated that genes involved in cell cycle proliferation, replication, and DNA repair were significantly downregulated. A network of affected cell cycle and cell proliferation-related genes is illustrated in FIG. 12. Among the 55 transcripts significantly affected by the piRNA, 52 transcripts were downregulated more than 1.5-fold. Of particular interest were heat shock protein genes HSP70 and HSPA8. Intracellular heat shock proteins are usually highly expressed in liver cancer cells, thus piR-37213-induced downregulation of these proteins and related pathways shows indicates it usefulness as an anticancer treatment. In addition, XRCC6 and PARP1, major DNA repair genes, were significantly reduced ~2-fold, indicating induction of cell cycle arrest and limited survival in treated cancer cells. Based on these observations, it is believed that piR-37213-mediated regulation of its target gene(s) serves to limit cellular growth, survival and repair.

Taken together, these findings reveal a previously unidentified functional role for the underexpressed piRNAs as tumor suppressors in liver tumorigenesis, and indicate that restoration of normal piRNA levels is a strategy for the treatment of liver cancer.

Example 5: piRNA Sequence Variants are Prognostic of Prostate Cancer Risk

Prostate cancer is the most common cancer in men, with men facing a 15% lifetime risk of developing the cancer and it predicted to make up 26% of new cancer cases in males in 2015, for a total of 220,800 new cases. Additionally, it is predicted to account for 9% of cancer related deaths in men during 2015[1]. During the period of 2007-2011, the incidence of prostate cancer was about 1.65 times higher in African Americans than in Caucasians[1]. Additionally, recent research demonstrated that race modifies the risk of prostate cancer due to obesity, with obesity being a stronger risk factor in African Americans than Caucasians. Among other factors, it has been hypothesized that the difference in prostate cancer risk between these two races has a genetic component. By performing this study in both an African American and Caucasian sample, genetic contributions to these racial differences could be explored.

The discovery of PIWI proteins and PIWI-interacting RNA (piRNAs), a class of small non-coding RNAs, and the subsequent understanding of their biological role has spawned interest in the potential role of these small RNAs in disease.

The piwi gene was first identified in *drosophila* through a genetic screen for genes affecting asymmetric division of germline stem cells, and was then found to code for a highly-conserved protein present in the stem and somatic cells of the *drosophila* germline that is implicated in germline establishment and maintenance. PIWI proteins are members of the Argonaute family of proteins, which contain a PAZ domain that binds single-stranded RNA, a MID domain, and a PIWI domain that resembles the endonuclease RNase-H. Homologs of *drosophila* piwi were then identified in various other organisms including mice and humans. After the discovery of PIWIs, it was shown that the already characterized rasiRNAs and additional small RNAs interact with PIWI proteins, thus being named piRNA. The piRNAs identified primarily mapped to intergenic regions and are enriched in repetitive elements, with about 20% in vertebrates mapping to transposon sequences.

Work to determine the function of PIWI/piRNAs has shown that the two are involved in the repression of transposable elements through transcriptional and post-transcriptional mechanisms, likely to maintain genome integrity$_{15-24}$. In terms of transcriptional regulation, it has been shown that mutations in *drosophila* piwi and aub, two PIWIs, lead to a failure to establish
H3K9me2/3 marks, a repressive histone modification$_{25-27}$. In *drosophila*, this mechanism involves the interaction of PIWI proteins with Heterochromatin Protein-1 (HP1), demonstrating the ability of PIWI/piRNA complexes to recruit epigenetic modifiers to gene loci. The process of inducing epigenetic changes involves PIWI-bound piRNAs guiding PIWI in complex with epigenetic regulators to complementary DNA sequences or nascent transcripts where their action can take place.

Being of the same gene family as the proteins known to interact with miRNA, it is not surprising that evidence of a gene regulatory role for PIWI/piRNAs has also arisen. There is evidence in mice of PIWI/piRNAs directing the methylation of promoters, a DNA modification associated with decreased gene expression, in a sequence specific manner$_{31}$. In *drosophila*, cytoplasmic PIWIs participate in inhibiting maternal mRNA translation and maternal mRNA decay via CCR4 mediated deadenylation by complementarity with their 3' UTRs. Further, piRNAs can be generated from the 3' UTR of certain mRNAs in *Drosophila, Xenopus*, and mice, providing another possible method of regulation.

As these functions of PIWI proteins and piRNA have been elucidated, evidence of their association with cancers has come to light. PIWI expression has been demonstrated in a variety of human cancers, including colorectal, hepatic, brain, pancreatic, testicular, prostate, breast, gastrointestinal, ovarian, and endometrial cancers. Additionally, expression of piRNAs has been observed in cancer cell lines and tissue samples. Of these, specific piRNAs have been observed to be under- or over-expressed in tumor tissue as compared to adjacent normal tissue, and amelioration of this aberrant expression showed the effect of decreasing cell proliferation.

As discussed herein, it is believed that sequence variants within piRNAs may play a role in cancer risk by aberrant regulation of tumor suppressor or oncogene expression. As piRNAs serve as a sequence specific guide for PIWI proteins, their action at certain loci may be abolished or aberrantly target new loci. This idea is supported by the fact that single nucleotide changes in piRNAs can lead to a substantial loss of efficiency at intended target sites. The assays described below test this mechanism in relation to prostate cancer in an African American population derived from the Multi-ethnic Cohort (MEC) and Caucasian population from the Cancer Genetic Markers of Susceptibility (CGEMS) Prostate, Lung, Colorectal, and Ovarian Cancer Screening Trial (PLCO) by investigating associations with single nucleotide polymorphisms (SNPs) embedded in piRNA sequences. The analyses are concentrated on piRNAs derived from 100 or fewer genetic loci, as there is evidence that low copy number piRNAs are more likely to regulate protein-coding gene expression.

Materials and Methods

Data

Data for this study were obtained from the Database of Genotypes and Phenotypes (dbGaP) and includes genotype and phenotype data for African American subjects from the GENEVA Prostate Cancer study (phs000306.v4.p1) genotyped on the Illumina Human1MDuov3_B platform and Caucasian subjects from the CGEMS PLCO Prostate Cancer study(phs000207.v1.p1) genotyped on the Illumina HumanHap300v1.1 and HumanHap250Sv1.0 platforms. The subjects in the GENEVA study were derived from the MEC, as well as six additional studies as documented by Freedman et al. (*Proc. Natl. Acad. Sci. USA* 103, 14068-73, 2006). Subjects in the PLCO study were drawn from the PLCO Cohort by an incidence density sampling method.

Data Cleaning

All data cleaning/management was performed using PLINKv1.07. For both study populations, consent groups were all genotyped on the same platform and were merged to make a complete data set. However, prior to merging consent groups the data were cleaned to remove individuals with a call rate <90%, SNPs with a call rate <95%, and SNPs not following HWE (p<0.0001). SNPs of low MAF were not removed, as they were not to be used for association analyses and would help inform subsequent imputation. SNPs on the Y chromosome, from pseudo-autosomal regions, and mitochondrial SNPs were removed. The data was then lifted over to genome build 37, and variant coding was flipped as necessary to be on the (+) genomic strand in order to be compatible with the imputation reference panel. One sample was removed from each related or duplicate pair in the data, as determined by >>0.2 from IBS analysis in plink.

Individuals not self-declared for the ancestry of interest were also excluded. Ancestry checks were then performed by combining the genome-wide data with a HapMap reference panel followed by principal component analysis using EIGENSTRAT$_{50}$. All subjects in the Caucasian population clustered well with HapMap Caucasians, so no removals were made.

However, due to
African Americans being an admixed population and no clear clustering in relation to HapMap samples, PCA was performed using EIGENSTRAT$_{50}$ and subjects exceeding six standard deviations on any of the top ten principal components were removed with one iteration.

piRNA SNP Genotype Imputation piRNA Bank were used to determine the position, sequence, and copy number of all curated human piRNA sequences. This includes 32,149 unique piRNAs that map to 667,944 genomic loci. The 1,000 Genomes Phase 3 reference data available for IMPUTE2 and piRNA coordinates were used to determine all SNPs mapping to genomic coordinates covered by piRNAs encoded at 100 or fewer loci, as imputation is limited to variants in the reference panel.

Next, imputation was carried out using IMPUTE2 in 5 MB segments with the programs default settings. The program outputs a probability of having each of the three possible genotypes for each individual. SNPTEST then uses these probabilities to determine allele dosages for use in a logistic regression model as described in the subsequent section.

Association Analyses

Association analyses were carried out in SNPTESTv2.5 using unconditional logistic regression with an additive allelic model that inputs posterior genotype probabilities as dosages and accounts for uncertainty due to imputation$_{53}$. Prior to the analyses, monomorphic SNPs as well as those with MAF<1% or with an info score <0.9 from IMPUTE2 were excluded. For the analyses in African Americans, models were adjusted for 3 principal components, an ordinal variable representing age categories, and study. The analyses in Caucasians controlled for 3 principal components, an ordinal age category variable, and family history of prostate cancer.

For both analyses age was grouped by ten-year increments, and the number of principal components to control for was determined by calculating a genomic inflation factor (GIF) and inspecting QQ plots both generated using genome-wide data. Principal component analysis was carried out in EIGENSTRAT with LD-pruned data generated from plink$_{49}$ using a pairwise $R_2$ threshold of 0.5.

Fine Mapping

Fine mapping was performed on regions containing variants associated with prostate cancer. For this, all variants from the Thousand Genomes reference panel in the original 5 MB imputation window of the associated SNP were imputed using IMPUTE2 in the same manner as previously. Association testing was then carried out using SNPTEST for all variants in a 500 KB window centered on the SNP of interest while controlling for all of the same variables as in the piRNA variant association analyses. Imputed variants were limited based on an info quality metric of 0.6. P-values were then used to generate Manhattan plots for inspection of the distribution of the association signal.

Results

GENEVA Study

After data cleaning in preparation for piRNA variant imputation, the African American population consisted of 2,275 cases and 2,425 controls for a total of 4,700 individuals with genotype data at 1,121,335 SNPs. During cleaning, 48 individuals were removed following IBS analysis and 22 were removed due to being PCA outliers after it was determined this would be necessary by inspection of ancestry plots. Following this, piRNA SNP genotypes were imputed for each subject at all possible piRNA variants using IMPUTE2.

Prior to association testing, variants that were monomorphic, had a MAF<1%, or an IMPUTE2 quality info score <0.9 were removed. The association analyses were controlled for the study a subject was drawn from, age categorized in ten year increments, and the top three eigenvectors from PCA. The choice to control for three principal components was made based on the observation of a GIF of 1.00 from genome-wide association analyses and examination of QQ plots generated from these analyses.

Figure 13A:
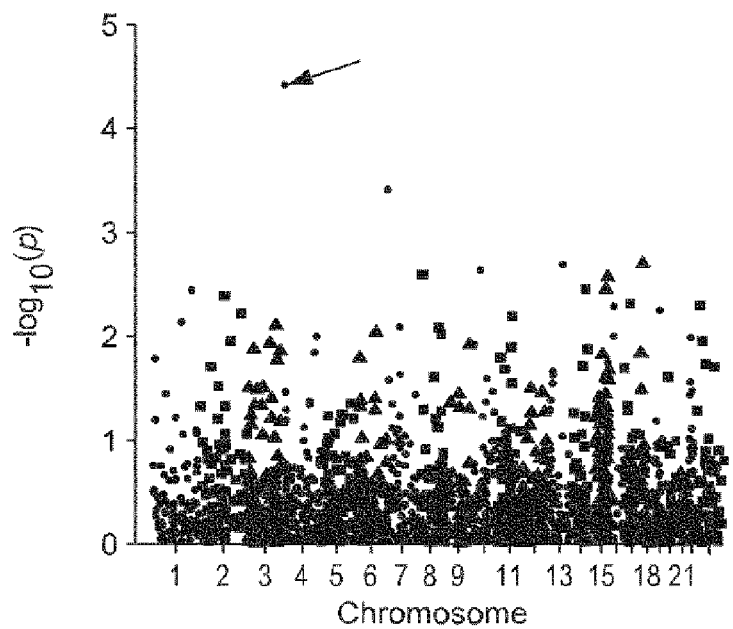
FIG. 13A is a Manhattan plot displaying the association results for imputed piRNA variants from the African American subjects of the GENEVA study of prostate cancer. The significantly associated variant, rs61101785 (located in piR-021163), is indicated with an arrow.
Figure 13B:
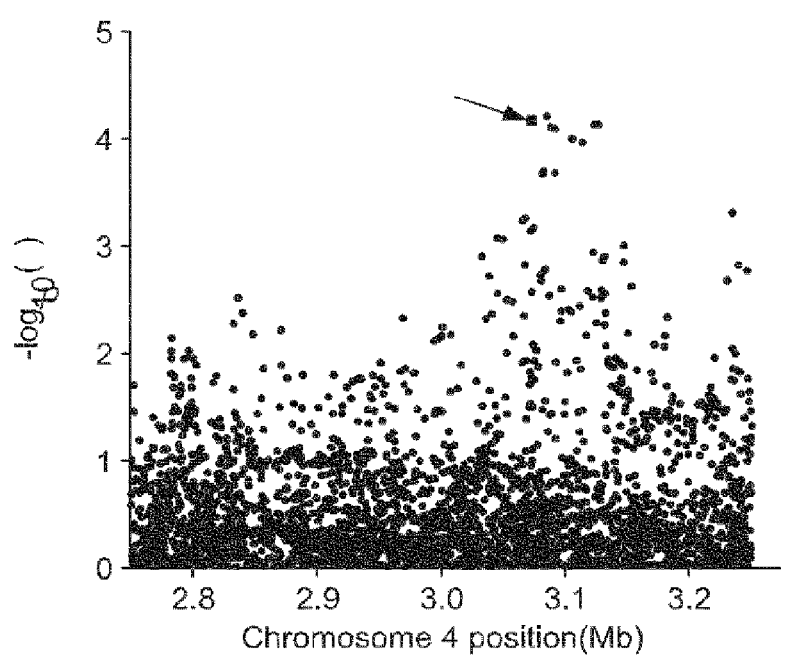
FIG. 13B is a Manhattan plot displaying the results of fine mapping of the region encompassing rs61101785, which is indicated with an arrow.

Association analyses, controlled as described above, were carried out for 1847 variants, the results of which are displayed in FIG. 13A. The variant rs61101785, located in piR-021163, was associated with an increased risk of prostate cancer [FDR-p=0.070], with an odds ratio of 1.63 [95% CI: 1.29-2.05] (Table 4). The MAF of the variant was 4.1% in cases and 2.6% in controls, and is located at Chr4: 3,074,158. The piRNA it falls within maps only to this locus. The locus lies within the first intron of the Huntingtin antisense 1 (HTT-AS1) transcript (UCSC Genome Browser). Fine mapping of the region encompassing rs61101785 revealed that the association signal peaks at that variant falling within piR-021163 (FIG. 13B).

TABLE 4

Summary of the top three hits from the GENEVA African American and PLCO Caucasian samples. FDR-adjusted p-values <0.10 and <0.20 were considered significant and suggestive, respectively.

| Variant | Location | piRNA | MAF Cases | MAF Controls | OR [95% CI] | P | FDR-Adjusted P |
|---|---|---|---|---|---|---|---|
| GENEVA (n = 4,700) | | | | | | | |
| rs61101785 | Chr4: 3,074,158 | piR-021163 | 4.1% | 2.6% | 1.63 [1.29, 2.05] | 3.80E−05 | 0.070 |
| rs62439721 | Chr7: 6,762,443 | piR-003123 | 16.8% | 19.3% | 0.84 [0.76, 0.94] | 3.89E−04 | 0.359 |
| rs11074184 | Chr15: 93,970,292 | piR-008061 | 9.6% | 11.6% | 0.81 [0.71, 0.93] | 3.55E−03 | 0.596 |
| PLCO (n = 2,240) | | | | | | | |
| rs8010969 | Chr14: 88,626,243 | piR-013783 piR-014246 | 19.6% | 16.0% | 1.28 [1.10, 1.49] | 1.18E−03 | 0.180 |
| rs11625907 | Chr14: 88,625,605 | piR-008286 | 19.7% | 16.0% | 1.28 [1.10, 1.49] | 1.17E−03 | 0.199 |
| rs8020378 | Chr14: 88,624,946 | piR-018495 | 19.7% | 16.0% | 1.28 [1.10, 1.50] | 1.15E−03 | 0.225 |

PLCO Study

After data cleaning, there were 1,142 cases and 1,098 controls for a total of 2,240 Caucasian subjects from the PLCO study genotyped at 541,721 variants. During cleaning, 7 samples were removed due to not being genotyped on both platforms and 53 were removed following IBS analysis. All remaining subjects clustered well with HapMap.

Figure 13C:
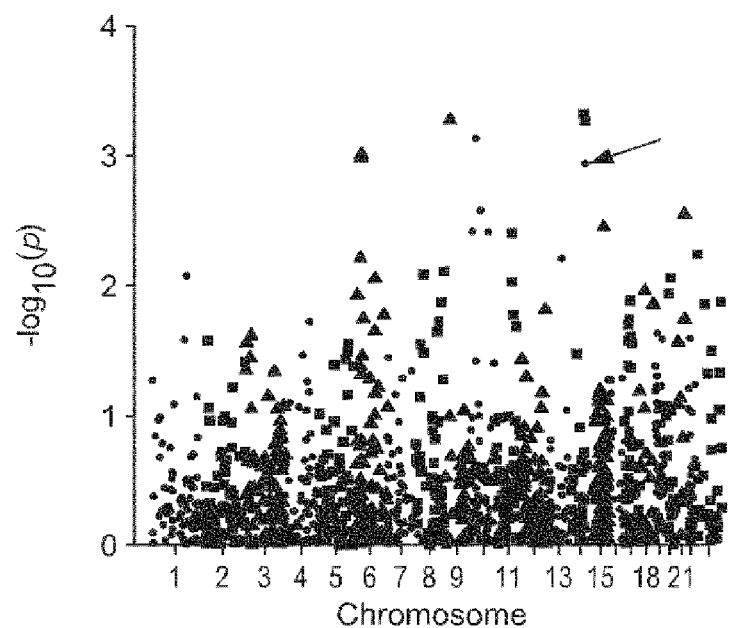
FIG. 13C is a Manhattan plot displaying the association results for imputed piRNA variants from the Caucasian subjects of the PLCO study. The variants rs8010969 and rs11625907 are indicated with an arrow.

Caucasians on the top two principal components, so no PCA outlier removal was performed. Next, all SNPs falling within piRNAs encoded at 100 or fewer loci were imputed for use in association analyses. The association tests were adjusted for family history of prostate cancer, age categorized in ten year increments, and the top three principal components from PCA based on a GIF of 1.00 and QQ plot inspection. As in the African American population, variants that were monomorphic, had a MAF<1%, or an IMPUTE2 info score <0.9 were removed. Associations were tested at 1,364 SNPs, the results of which are summarized in FIG. 13C. The top three hits are all located within the same piRNA cluster on Chromosome 14, which lies in an intergenic region. Interestingly, the hits within this single piRNA cluster all correspond to single copy piRNAs. The fine mapping carried out on the imputation region encompassing rs8010969 and rs11625907 revealed that they are likely tagging a causal SNP.

Conclusions

The foregoing experiments yielded a comprehensive analysis investigating the association between genetic variants within piRNAs and prostate cancer in both an African American and Caucasian sample. The study focused on an African American sample genotyped as part of the GENEVA study and Caucasian population drawn from the PLCO study, both available via dbGaP. Investigation of associations between imputed piRNA variants and prostate cancer revealed a highly interesting association in the African American study sample. A variant falling within the singly encoded piR-021163, rs61101785, was associated with an increased risk of prostate cancer in African Americans (FDR−p=0.0702).

Fine mapping of the region encompassing rs61101785 demonstrated that the association signal peaks at the variant. This supports the idea of a functional role for this variant given the signal is real. The location of the variant (Chr4: 3,074,158) and piRNA (Chr4: 3,074,147-3,074,178) falls within the first intron of the HT-AS1 transcript. HTT-AS1 is non-coding and antisense to the Huntingtin (HTT) gene, a gene causally linked to Huntington's disease when containing a PolyQ expansion, with the two being transcribed head-to-head. The HIT-AS1 transcript is known to regulate the expression of the HIT gene in a partially Dicer dependent manner. The normal HTT gene has been implicated in cell survival$_{57}$, an important aspect of cancer development and progression.

Interestingly, piRNAs typically target transposons by deriving from antisense transcripts and imprinting of the Rasgfr1 locus in mice involves the targeting of an adjacent antisense transcript by a specific piRNA. Although speculative, it is possible that this piRNA is derived from the antisense transcript and can then target the genomic locus. Another interesting aspect of this variant is that it was virtually monomorphic in the Caucasian sample, with only two cases being heterozygous at this position. This could partially account for the race differences observed in prostate cancer risk. The associations observed in the piRNA cluster on chromosome 14 in the Caucasian sample are all likely reflecting the same functional variant if one is truly present.

A strength of this study is the Thousand Genomes reference panel used for imputation, as this data has highly comprehensive coverage of an immense number of variants, thus coverage of many piRNA embedded SNPs was achieved. However, variants within piRNAs not included in the reference panel were not be investigated. Additionally, it cannot be definitively concluded that these variants are causal, as they may be tagging variants in linkage-disequilibrium with them. Finally, the results are limited to covariates provided in the dbGaP datasets, and could have potentially further controlled for confounding factors to bolster the results.

Overall these experiments provide the first evidence that piRNA sequence variants could be associated with prostate cancer, with a strong finding coming from the African American sample that could in part explain racial differences in prostate cancer risk. Fine mapping of the region strengthened this idea. Therefore, it is believed that not only aberrant expression of PIWIs or piRNAs can play a role in cancer, but piRNA sequence changes may also be a factor.

Example 6: piRNA Sequence Variants are Prognostic of Lung Cancer Risk

Lung cancer is the most frequently diagnosed cancer and the first and second leading cause of cancer death among males and females worldwide. In the United States, there will be an estimated 224,390 new cases and 158,080 new deaths of lung cancer in 2016. Moreover, the 5-year relative survival rate for lung cancer was only 18.4% from 2005 to 2011. Currently, for non-small-cell lung cancer patients, which accounts for 85% of lung cancer cases, the main treatment options are surgery, radiotherapy and adjuvant chemotherapy. However, since each treatment has its unavoidable side effects, a breakthrough in lung cancer treatment to increase the survival rate as well as improve the quality of life for lung cancer patients is needed. The advent of targeted therapy makes it possible to reduce the toxicity to patients compared to cytotoxic drugs. Therefore, to discover new agents with clinical significance that can be served as target for treatment of lung cancer in the future is especially important.

In recent years, increasing evidence indicates that the non-protein-coding portion of the genome is of functional importance for disease development, including cancer. Many studies show that non-coding RNAs (ncRNAs) function through modulation of transcriptional or posttranscriptional processes. Such transcriptional and posttranscriptional modifications would lead to a highly-conserved pathway in which the small non-coding RNAs (sncRNAs) bind to protein complexes (PPD or Argonaute) and form the RNA-induced silencing complexes (RISC) to inhibit the expression of its target sequences. The main small silencing RNAs can be classified into 3 categories: small interfering RNAs (siRNAs), microRNAs (miRNAs) and PIWI-interacting RNAs (piRNAs).

The length of piRNA sequence is between 26 and 31 nucleotides (nt), slightly longer than siRNAs and miRNAs (between 21 and 26 nt). The primary function of piRNAs is to stabilize the germ line genome by silencing the transposon elements (TEs) through a highly-conserved pathway which does not require Dicer during the process, while miRNAs or siRNAs-induced silencing pathways require Dicer. Besides the TE-silencing function of piRNAs in the germ line, a growing number of studies are investigating its role in somatic cells. The detection of 4 main types of PIWI proteins (PIWIL1/HIW1, PIWIL2/HILI, PIWIL 3, and PIWIL4) in mammalian somatic tissues provides evidence for the existence of somatic piRNAs. There are two pathways for the biogenesis of somatic piRNAs. In the primary processing pathway, long piRNA precursors are transcribed from piRNA clusters, cleaved and midified in the cytoplasma, and then transported into the nucleus loaded with Aubergine (AUB) or Piwi proteins. In the amplification loop (ping-pong cycle), which is activated by piRNA-induced silencing complexes (piRISCs) produced in the primary pathway, piRNAs are modified and amplified to target on active TEs through a slicer-mediated cleavage9. Moreover, the Piwi-piRNAs pathway can regulate the transposon loci or even non-transposon loci outside the germline tissues through histone modifications and DNA methylation.

Studies show that piRNAs and piRNA-like transcripts are involved in tumorigenesis in a range of tumor types. The oncogenic or tumor suppressor roles of piRNAs have both been found by microarray screening, next generation sequencing (NGS), and real-time quantitative reverse transcription-polymerase (PCR) chain reaction analyses. Several preliminary studies found the over-expression of Piwi proteins in several tumor types, such as seminomas, breast cancer, cervical cancer, glioma, colon cancer, etc. One possible mechanism proposed by was that the presence of piRNAs and Piwi proteins in the cancer tissues would result in aberrant DNA methylation and over-silencing of the promoting regions of tumor suppressor genes, and then trigger the tumorigenesis. Thus, piRNAs have high potential to be a new prognostic biomarker or new therapy target for various tumor types.

It is believed that there are very few previous studies investigating on the association between piRNAs/Piwi-expression and lung cancer risk. Therefore, the object of this study is to examine whether piRNAs variants are associated with lung cancer risk using the data of 3,817 cases and 3,921 controls from one case-control study and three cohort studies, and to further test the identified single nucleotide polymorphisms (SNPs) through in vitro functional analysis. Moreover, several piRNAs that are significantly different expressed in lung adenocarcinoma compared to normal lung tissues were also identified using the data derived from a scientific report of piRNAs expression in several tumor types through expression profiling.

Materials and Methods

Study Population and Data

The population of this study is derived from a genome-wide association study of lung cancer, in which the subjects are pooled from three cohort studies—Alpha-Tocopherol, Beta-Carotene Cancer Prevention Study (ATBC), the Prostate, Lung, Colon, Ovary Screening Trial (PLCO), and the Cancer Prevention Study II Nutrition Cohort (CPS-II). The accessible individual genotype and phenotype data are downloaded from Database of Genotypes and phenotypes (dbGaP, Study Accession: phs000336.v1.p1) to a secure server at Yale University and decrypted and extracted according to dbGaP guidelines. The total population of this study is 7738, with 3,817 cases and 3,921 controls.

The expression data of 252 piRNAs for 497 lung adenocarcinoma patients and 46 controls are obtained from the supplemental table 2 of the scientific report (*Sci Rep.* 275: 10423, 2015). The unit of piRNAs expression is defined as reads per kilobase per million mapped reads (RPKM) and all RPKM values are obtained from the scientific report.

Data Cleaning and Management

All processes of data cleaning and management are performed by PLINK v 1.07. Subjects from the 4 studies are genotyped on one of the four platforms (Illumina Human240K300K, HumanHap550K, Human610Quadv1, and Human1M-Duov3). The data of 539,000 SNPs in 3,817 cases and 3,921 controls are merged into one complete dataset. 124 pairs of subjects were found to have a familial relationship by identity by descent (IBD) analysis (pi-hat ($\pi$)>=0.2) and each member of the 124 pairs was excluded from the final analysis. The dataset was restricted to SNPs with call rate ≥90% and Hardy-Weinberg Equilibrium test (HWE) P>0.0001. Then, principal components analysis (PCA) was carried out using EIGENSTRAT and 173 subjects were excluded as outliers. Finally, the sample file contained 533,002 SNPs in 3702 cases and 3739 controls.

For the expression data, 52 piRNAs were excluded from the final analysis because 13 of these piRNAs are mapped with overlaps to microRNAs (miRNAs), 36 are mapped to small nucleolar RNAs (snoRNAs), and 3 are mapped to transfer RNAs (tRNAs). After confirming the correct mapping by piRNABank and UCSC genome browser, 200 piRNAs were included in the final analysis.

piRNA Variant Genotype Imputation and Fine Mapping

The piRNA SNP list including the copy number and genome loci is obtained from piRNABank. SNPs with copy number >100 were excluded because evidence showed that piRNAs with lower copy number are more likely to be involved in the regulation of protein-coding gene expression. The 1,000 Genomes Phase 3 haplotype variants were used as reference panel for imputation. The imputation was performed using IMPUTE v2.3.1 software. Fine mapping was performed through imputation of all SNPs with minor allele frequency (MAF)>1% in 5 MB segments and all the coordinates information are collected from Genome Reference Consortium GRCh37/hg19 on USCS genome browser.

Association Analyses

The statistical analysis of the association study was performed by SNPTEST v2.5 using unconditional regression regression and the additive allele model, controlling for sex, age, original study participation, genotyping platform, and the first two principal components. The number of the principal components to control is determined by the study-wide genomic inflation-factor (GIF) and the corresponding QQ plot. The odds ratio (OR), 95% confidence interval (95% CI), nominal p-value, and false discovery rate-adjusted (FDR) P-value is provided for every association. The Manhattan plot and QQ plot are generated by R using qqman package.

Comparison of piRNAs expression levels between normal and lung adenocarcinoma samples.

A scatter plot visualizing the different expression level of the 200 included piRNAs between samples from 497 lung adenocarcinoma patients and 46 controls was created by J-Express software. The 2-tail t-test was used to detect the difference of individual piRNA expression level between samples from 497 lung adenocarcinoma patients and 46 controls for the 200 included piRNAs. Bonferroni-adjustment for multiple comparisons has been applied.

Results

Two Identified piRNAs Associated with Lung Cancer Risk

Figure 14A:
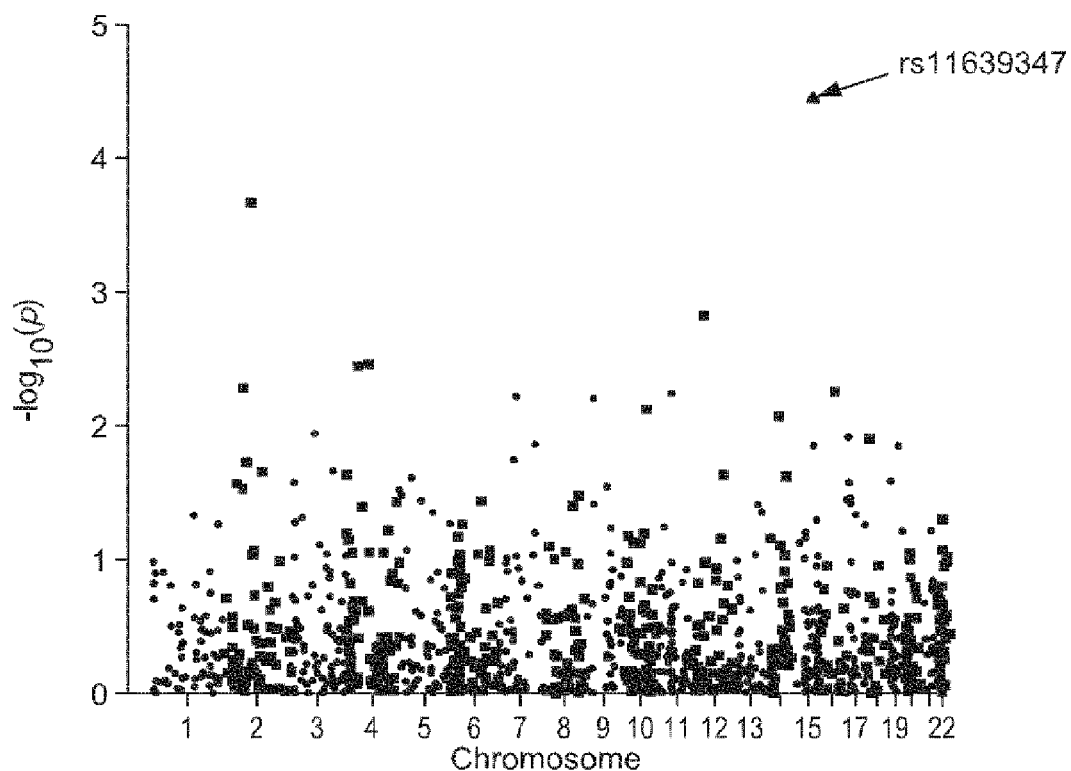
FIG. 14A is a Manhattan plot displaying the results from an association study of lung cancer for the 1,173 piRNAs variants. The variant rs1169347 is annotated in the plot.
Figure 14B:
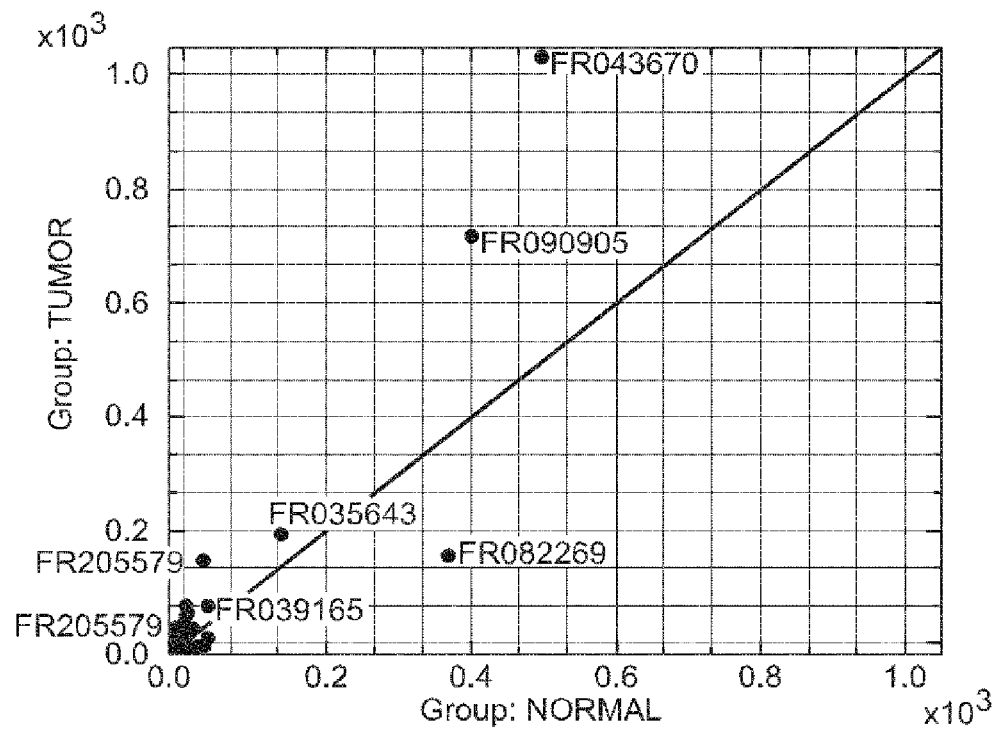
FIG. 14B is a scatter plot displaying the results of the secondary expression analysis of piRNA in lung cancer.

The baseline characteristics of the included 3,702 cases and 3,739 controls are shown in Table 4. There are more males in control group than case group. The age distribution is similar between the two groups. Higher proportion of controls are from PLCO study while more cases are from ATBC study. And samples from the cases are mostly genotyped on HumanHap550K and Human610Quadv1 array while controls are genotyped on all the four arrays. After all the data cleaning processes, genotype data of 533,002 SNPs in a total population of 7,441 have been included in the PCA analysis. A total of 1,173 SNPs that can be mapped to piRNAs of interest are successfully imputed and included into the final association studies. The association between these 1,173 variants and lung cancer risk is displayed in a Manhattan Plot (FIG. 14A). After adjusting for multiple comparisons by Bonferroni-correction, only one SNP (rs11639347) is statistically significant associated with lung cancer risk. rs11639347 can be mapped to two overlapping piRNAs, piR-5247 and piR-5671. As showed in Table 5, the minor allele of rs11639347 is a risky allele that increases lung cancer risk with an odds ratio (OR) of 1.17 (95% confidence interval (CI): 1.09, 1.27). Information about the SNP name, mapped piRNAs, position, allele, minor allele frequency, OR, nominal P-value, and FDR P-value for the top 3 identified SNPs are also included. The association analysis is controlled for sex, age, original study participation, genotyping platform, and the first two principal components.

Individual piRNAs Expression Level Difference

The scatter plot (FIG. 14A) shows the mean expression level of each individual piRNAs among 497 lung adenocarcinoma patients and 46 normal controls. Most piRNAs have very low expression level in both lung adenocarcinoma and normal samples. However, the expression level was detectable in several outlying piRNAs which showed different expression patterns in tumor samples compared to normal samples. The top-expressed 7 piRNAs in tumor samples have been listed in table 5. The information about the piRNA name, position, coding region, mean expression level in normal samples, mean expression level in lung tumor samples, nominal P-values generated by 2-tail t-test, and FDRP-values are provided. Table 5 includes top 5 piRNAs (piR-14620, piR-2732, piR-51809, piR-19521, and piR-15232) that are statistically significantly different between normal and tumor samples. Among them, piR-14620 is of the highest expression level and all of the 5 piRNAs are up-regulated in tumor samples. The only piRNA that is down-regulated in tumor samples of the top 7 piRNAs was piR-31637. However, after Bonferroni correction, the difference of its expression level was not statistically significant.

DISCUSSION

This is a comprehensive post-GWAS study combining the association results, expression profiling results, and the functional analysis results to explore the association between piRNAs variants and lung cancer risk. From the association analysis, a variant in one SNP (rs11639347) was identified that is significantly associated with the increase risk of lung cancer. The location of the variant (Chromosome 15: 79024350) and the 2 piRNAs, piR-5247 (Chromosome 15: 79024333-79024361) and piR-5671 (Chromosome 15: 79024327-79024355) is in intergenic region. This indicates that the functional changes caused by the 2 piRNAs may be attributed to the function of themselves.

From the expression analysis, 5 piRNAs were identified that are up-regulated in lung adenocarcinoma samples. Among which, piR-14620, the highest expressed piRNA, is located in the intron of gene KIAA0825. piR-2732 is located in the intron of gene RPL3, which encodes the ribosome proteins and is involved in DNA repair through regulation of p21 function. piR-51809 is located in the intron of gene CPA6. piR-19521 is located in the intergenic region. piR-15232 is located in the exon of HIST1H2BJ, which encodes H2B histone protein. Therefore, future studies are needed to explore the role of KIAA0825, CPA6 and HIST1H2BJ in lung cancer development. Functional analysis of piR-2732 should be further conducted since it seems be involved in cancer development through regulation of DNA repair and cell apoptosis.

There are several strengths of this study. First, in association study, the use of 1,000 Genome Phase 3 haplotype reference panel guarantees a wide coverage of piRNA embedded SNPs during imputation. Second, the result of cell viability assay shows rs11639347 only functions to promote the lung cancer cell growth, indicating it may be a good specific target for future lung cancer treatment. Third, from the association study and expression analysis, several piRNAs variants associated with lung cancer risk were identified and are located in protein-coding regions as well as intergenic regions. This finding provides further evidence that piRNAs play important roles in tumorigenesis through either their independent biological roles or interactions with oncogenes or tumor-suppressor genes. Lastly, the combination of association study, expression analysis, and functional analysis provides a comprehensive understanding of the identified SNPs that are associated with lung cancer risk.

Example 6: GWAS Study Identified piRNAs Associated with Breast Cancer Risk

Materials and Methods

Description of GWAS datasets for the study subjects for the primary imputation analysis will be participants of the Cancer Genetic Markers of Susceptibility (CGEMS) Breast Cancer GWAS, nested within the Nurses' Health Study cohort. Genome-wide genotype data have been made publicly available in the Database of Genotypes and Phenotypes (dbGaP) for 1,434 cases of European descent with confirmed invasive breast cancer and 1,142 controls matched on age, ethnicity, and time of blood collection (Table 6). Subjects are predominantly post-menopausal; however, a small number of pre-menopausal women are also included.

TABLE 6

| Study (Ethnicity) | cases | Controls | dbGaP Accession |
|---|---|---|---|
| Cancer Genetic Markers of Susceptibility (CGEMS) | | | phs000147.v2.p1 |
| Caucasian | 1,434 | 1,142 | |

In order to examine the association between piRNA variants and breast cancer risk in a preliminary set of piRNA SNPs, imputation was performed for 479 SNPs with MAF>10% harbored within single-copy piRNA sequences in the CGEMS population; 68 SNPs also meeting these criteria had been directly genotyped. Imputation was performed as described above based on genotypes at 531,549 SNPs after data cleaning as described. After restriction to genotypes that were imputed with quality >0.80, 483 SNPs remained for association analysis. Associations were adjusted for age, family history of breast cancer, and the first three principal components to adjust for potential population substructure.

Results

Association analysis results are presented in Table 7. As shown, four SNPs harbored in piRNAs piR-17319, piR-9422, piR-16556, and piR-3467 were observed to have associations with breast cancer risk with an effect size of at least 1.25 (0.80) and a significance level of P<0.01. The top SNP identified, rs28649125 in piR-17319, is of particular interest owing to the high MAF of the protective variant allele and the corresponding population attributable risk of 7.8%. Although the identified associations approach, but do not surpass, a strict correction for multiple comparisons (the Bonferroni-corrected significance threshold at $\alpha=0.05$ is approximately $1\times10^{-4}$), this by no means rules out the potential functional importance of these variants, which is reflected by the effect sizes and nominal significance levels observed. Studies show the functional implications of inherited variants identified by genetic association studies even in the absence of genome-wide significance, for example in the case of rs11614913 in miR-196a-2 and

TABLE 7

Results of piRNA variant association analyses

| rsID | piRNA | Chr: Position | OR (95% CI) | P-value | MAF | Genotyping method |
|---|---|---|---|---|---|---|
| rs28649125 | piR-17319 | 22: 48,003,769 | 0.79 (0.70-0.90) | $4.16 \times 10^{-4}$ | 0.34 | Imputed |
| rs11914017 | piR-9422 | 22: 17,442,223 | 1.33 (1.10-1.60) | $2.53 \times 10^{-3}$ | 0.12 | Imputed |
| rs10518263 | piR-16556 | 19: 51,954,722 | 0.80 (0.70-0.94) | $4.76 \times 10^{-3}$ | 0.18 | Directly genotyped |
| rs72755158 | piR-3467 | 15: 97,309,811 | 1.27 (1.07-1.51) | $7.02 \times 10^{-3}$ | 0.13 | Imputed |

Example 7: Next-Generation Sequencing Identified Differentially Expressed piRNAs in Breast Cancer Materials and Methods
Small RNA-Seq Datasets of Breast Cancer The small RNA-Seq raw data of 14 matched pair tissues (human triple-negative breast cancers and corresponding adjacent normal tissue) from 14 patients were downloaded from NCBI Gene Expression Omnibus (GEO) database (http://www.ncbi.nlm.nih.gov/geo/) with accession number GSE40049. These single-end raw reads were generated by the SOLiD 4 System (Applied Biosystems) (see table 8).

TABLE 8

General information of the small RNA-Seq data (GSE40049).

| No. | Experiment Title | sample name | Total Spots |
|---|---|---|---|
| 1 | GSM984354 | 291_N | 20162287 |
| 2 | GSM984330 | 291_T | 19388298 |
| 3 | GSM984355 | 357_N | 42560664 |
| 4 | GSM984331 | 357_T | 24119025 |
| 5 | GSM984356 | 477_N | 36143891 |
| 6 | GSM984334 | 477_T | 25228427 |
| 7 | GSM984357 | 507_N | 39845976 |
| 8 | GSM984335 | 507_T | 26240891 |
| 9 | GSM984358 | 557_N | 29001741 |
| 10 | GSM984337 | 557_T | 16899980 |
| 11 | GSM984359 | 574_N | 27158895 |
| 12 | GSM984338 | 574_T | 16594155 |
| 13 | GSM984360 | 582_N | 26898945 |
| 14 | GSM984339 | 582_T | 17480235 |
| 15 | GSM984361 | 602_N | 27579798 |
| 16 | GSM984341 | 602_T | 15729927 |
| 17 | GSM984362 | 673_N | 19138479 |
| 18 | GSM984344 | 673_T | 17311955 |
| 19 | GSM984363 | 677_N | 87465206 |
| 20 | GSM984345 | 677_T | 19005125 |
| 21 | GSM984364 | 881_N | 41677661 |
| 22 | GSM984346 | 881_T | 29904881 |
| 23 | GSM984365 | 887_N | 23755015 |
| 24 | GSM984347 | 887_T | 13857306 |
| 25 | GSM984366 | 918_N | 48831229 |
| 26 | GSM984351 | 918_T | 48368267 |
| 27 | GSM984367 | 922_N | 19542481 |
| 28 | GSM984352 | 922_T | 20143745 |

Bioinformatics Analysis

Figure 15A:
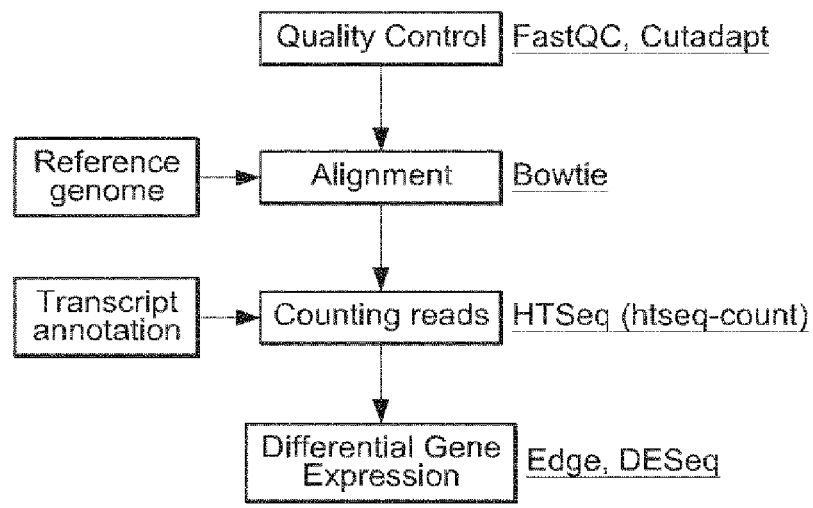
FIG. 15A is an overview of count-based differential expression pipeline for small RNA-seq data.

Quality control checks on raw data were performed using FastQC v 0.11.3. After that, the raw reads were trimmed and filtered using Cutadapt v 1.8.3 (https://pypi.python.org/pypi/cutadapt). Reads with a quality score lower than 20 and shorter than 16 were discarded. The clean reads were used for downstream analysis as potential piRNAs. Then, the bioinformatics analysis was processed using a protocol of RNA-seq analysis based on the read-count. The pipeline of data processing was showed in the FIG. 14A. In brief, quality reads were mapped to the reference genome hg18 using Bowtie v 1.1.2 (http://bowtie-bio.sourceforge.net/index.shtml). HTSeq (htseq-count) v 0.6.1 was used for counting reads according to the transcript annotation files, which were downloaded from piRNABank (http://pimabank.ibab.ac.in/) and converted to GTF/GFF format. The gene expression level was normalized by the number of uniquely mapped reads per million mapped reads (RPM). DESeq or Edge, the R package, was then used to analyze the output files from htseq-count and visualize the results of differential expression analysis. FIG. 15A is an overview of count-based differential expression pipeline for small RNA-seq data.

Real-Time qRT-PCR

Four total RNAs isolated from breast cell lines were used. It was polyadenylated and reversely transcribed using the NCode miRNA First-Strand Synthesis and qRT-PCR Kits (Invitrogen) according to the user manual. Then, the cDNA was subjected to two-step relative quantitative RT-PCR using NCode universal reverse primer in conjunction with a sequence-specific forward primer (see table 9) for piRNA. A master mix was prepared for each PCR reaction using the KAPA SYBR FAST qPCR kit (Kapa Biosystems), which included SYBR FAST qPCR Master Mix, Forward primer, Universal qPCR Primer, ROX Reference Dye and 1 μL template cDNA. RNU6B was used as reference gene for the relative quantification of piRNAs. The reactions were placed in a 96-well plate (ABI) using ABI 7500 Fast real-time PCR system. PCR cycling conditions are: 95° C. for 3 min, followed by 40 cycles of 95° C. for 3 s and 63° C. for 25 s. After cycling, The $C_T$ value was obtained from the ABI sequence detection software (v 1.3).

were transfected with piRNA mimics using Lipofectamine RNAiMAX (Invitrogen) following manufacturer's instructions. Mock transfections with nonspecific siRNA duplexes were used as the negative controls. Cells were treated for 48

TABLE 9

The list of piRNA forward primers.

| piRNABank Accession | NCBI Accession | Primer sequence (5'-3') | Length (bp) | GC Content (%) | Tm (° C.) |
|---|---|---|---|---|---|
| hsa_piR_018292 | DQ595186 | TTGCTGTGATGACTATCTTAGGACACCTTTG (SEQ ID NO: 49) | 31 | 41.9 | 59.7 |
| hsa_piR_016975 | DQ593415 | CGTCCATGATGTTCCGCAACTACCTACA (SEQ ID NO: 50) | 28 | 50.0 | 61.7 |
| hsa_piR_017178 | DQ593744 | CTGCAGTGATGACTTTCTTAGGACACCTTTG (SEQ ID NO: 51) | 31 | 45.2 | 60.5 |
| hsa_piR_019169 | DQ596314 | GACCAATGATGAGTATTCTGGGGTGTCTGAA (SEQ ID NO: 52) | 31 | 45.2 | 61.0 |

Cell Lines

Three breast cell lines, including MCF-10A, MCF-7 and MDA-MB-231, were purchased from the American Type Culture Collection (ATCC) and cultured using the following conditions. MCF-10A (ATCC®CRL 10317™) cells, a spontaneously immortalized normal human mammary epithelial cell line, were cultured in Mammary Epithelial Cell Growth Medium (MEGM) (Lonza) supplemented with 10% fetal bovine serum (FBS) and 100 ng/ml cholera toxin. MCF-7 (ATCC®HTB22™), a breast cancer cell lines, were cultured in Eagle's Minimum Essential Medium (EMEM) (ATCC® 302003™) supplemented with 10% FBS and 0.01 mg/ml human recombinant insulin. Above these cells were maintained at 37° C., 5% $CO_2$ in a humidified incubator (Thermo). MDA-MB-231 (ATCC®HTB-26™), were cultured at 37° C. without $CO_2$ in Leibovitz's L-15 Medium (ATCC®30-2008™) supplemented with 10% FBS.

piRNA Mimics Transfection and Cell Proliferation Assay

To study the possible effect of piR_018292 (DQ595186), its mimics were transfected into breast normal and tumor cells. The mimics were synthesized by integrated DNA technologies (IDT), Inc. Cells cultured in 96-well plates to 96 hours to allow maximum effects of transfection. After that, cell viability was determined by a CellTiter 96® Aqueous One Solution Cell Proliferation Assay (MTS) kit (Promega) according to manufacturer's instructions. The resulting formazan product was quantitated by a multi well spectrophotometer at 490 nm.

Results

Differential Expression of piRNA Based on RNA-Seq Analysis

Figure 15B:
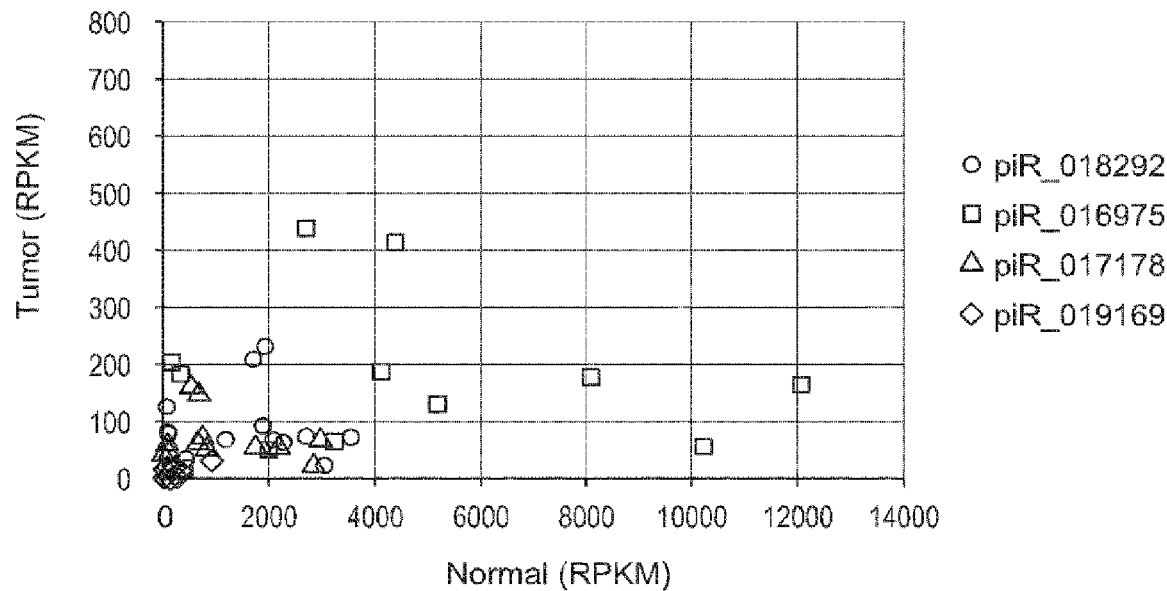
FIG. 15B is dot plot of differential expression of four piRNA genes in breast cancer.

To identify piRNAs expressed differentially between normal and malignant breast tissue, 14 matched pairs of triple-negative breast cancers and adjacent normal tissues were analyzed. Differentially expressed piRNAs were identified using matched-pair t-test. There were totally 201 piRNA gene loci differentially expressed (p<0.05) to be identified, and a list of the top 14 piRNAs (p<0.01) was shown in Table 10. Among the 14 piRNAs, four piRNAs (piR_016975, piR_019169, piR_018292 and piR_017178) were most significantly downregulated in breast tumor tissues (see FIG. 15B).

TABLE 10

A list of the top 14 piRNAs differentially expressed in 14 matched pairs breast normal and tumor tissues.

| piRNABank Accession | NCBI Accession | Gene Location | Mean_T/N (RPM) | Fold change (log2) | p-value (t-test) |
|---|---|---|---|---|---|
| piR_016975 | DQ593415 | chr19: 54685976-54686003 | 153.56/3802.94 | -4.63 | 3.92E-03 |
| piR_019169 | DQ596314 | chr14: 100466011-100466041 | 8.41/204.12 | -4.60 | 6.98E-03 |
| piR_018292 | DQ595186 | chr18: 45269646-45269676 | 87.87/1507.77 | -4.10 | 6.59E-04 |
| piR_017178 | DQ593744 | chr18: 45271685-45271715 | 63.28/984.53 | -3.96 | 5.54E-03 |
| piR_019368 | DQ596603 | chr1: 154156432-154156462 | 9.26/113.18 | -3.61 | 8.26E-03 |
| piR_019911 | DQ597340 | chr14: 20930222-20930253 | 18.13/124.91 | -2.78 | 1.61E-03 |
| piR_000560 | DQ570698 | chr17: 24071728-24071758 | 268.27/1758 | -2.71 | 3.96E-03 |
| piR_001207 | DQ571591 | chr16: 88155360-88155385 | 530.84/3078.92 | -2.54 | 6.86E-03 |
| piR_012753 | DQ587269 | chr2: 232029453-232029478 | 29.2/134.73 | -2.21 | 5.96E-03 |
| piR_003728 | DQ575064 | chr14: 20935370-20935400 | 39.48/148.77 | -1.91 | 4.89E-03 |
| piR_001078 | DQ571388 | chr6: 31616882-31616910 | 1028.11/3714.73 | -1.85 | 2.24E-03 |
| piR_012925 | DQ587514 | chr1: 31181176-31181205 | 6.26/21.67 | -1.79 | 2.85E-03 |
| piR_020582 | DQ598312 | chr15: 63948497-63948525 | 94.01/45.53 | 1.05 | 2.64E-04 |
| piR_004987 | DQ576872 | chr15: 43278139-43278169 | 63.71/30.04 | 1.08 | 9.07E-03 |
| piR_020582 | DQ598312 | chr6: 27623553-27623581 | 94.8/43.38 | 1.13 | 3.23E-04 |
| piR_020582 | DQ598312 | chr6: 29017400-29017428 | 95.39/43.19 | 1.14 | 7.55E-05 |

Validation of piRNAs Differentially Expressed by RT-qPCR

Figure 15C:
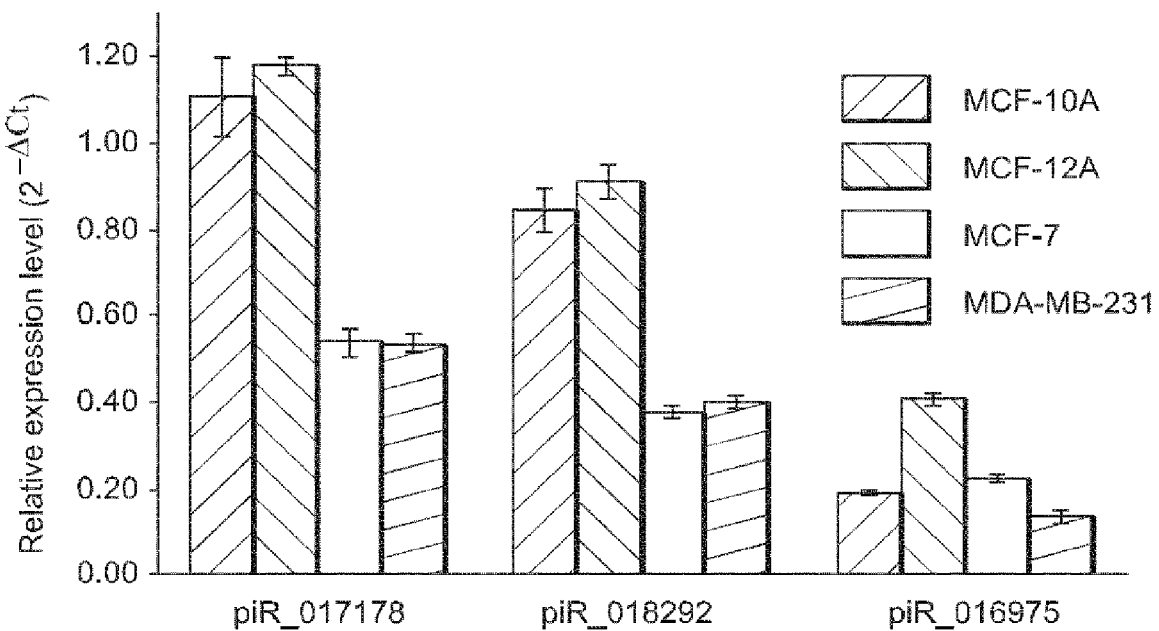
FIG. 15C is a bar graph showing validation of differential expression of four piRNA genes in breast normal and tumor cell lines by RT-qPCR.

To validate the differential expression of 4 piRNAs, total RNA isolated from 4 breast cell lines (MCF-10A, MCF-12A, MCF-7 and MDA-MB-231) was used to analysis by RT-qPCR (see FIG. 15C). Results showed that the expression level of both piR_017178 and piR_018292 in normal cell lines was significantly higher than in tumor cell lines, which was in accordance with the results from RNA-seq analysis. For piR_016975, its expression level was not coincident in two normal cell lines. Moreover, its expression level in MCF-10A was similar with two tumor cell lines. The expression of piR_019169 cannot be detected in four cell lines.

Biological Effect of piR_018292 Over-Expression in Breast Tumor Cells

Figure 15D:
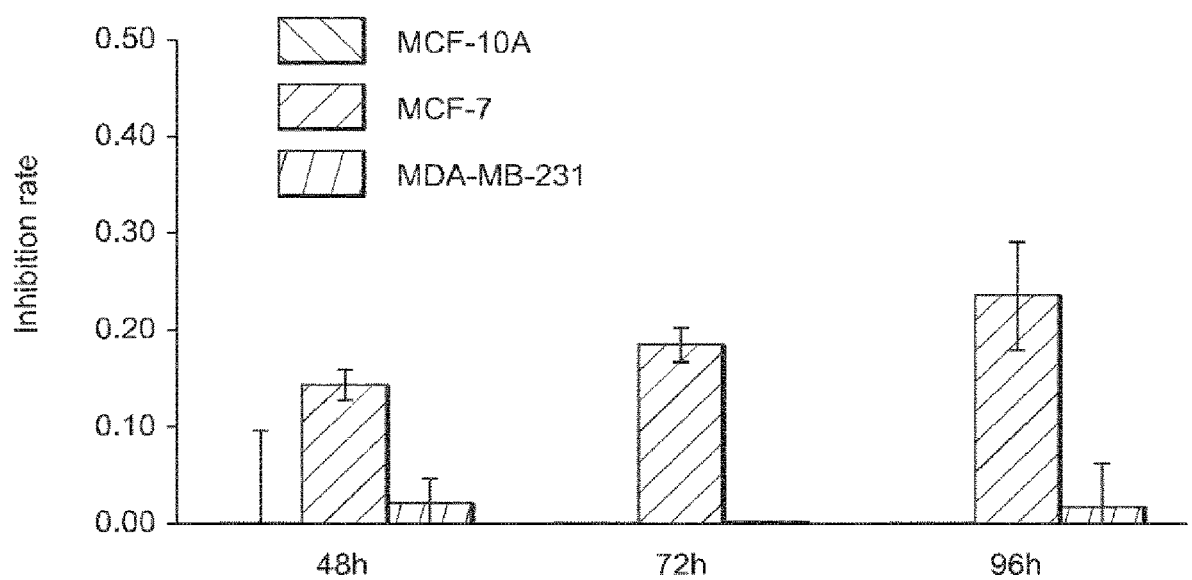
FIG. 15D is a bar graph showing the inhibition rate of breast cells after overexpression of piR_018292 (oligo concentration=30 nM).

To address the role of piR_018292 in breast tumor cells, it was over-expressed in three cell lines (MCF-10A, MCF-7 and MDA-MB-231) by transfection and the cell viability was detected by MTS tetrazolium assay. The results shown that, compared to the MCF-10A, overexpression of piR_018292 can significantly downregulate the proliferation rate of MCF-7. However, it was no significant impact on the proliferation and viability of MDA-MB-231 (see FIG. 15D).

TABLE 2

Primers used for qPCR and MS-PCR reactions and piRNA mimics used for in vitro functional analyses

| Amplification target[1] | Forward primer | Reverse primer |
| --- | --- | --- |
| TNFRSF10D | 5'-TTCTCCACAGTAGCCCAGTC-3' (SEQ ID NO: 53) | 5'-GGCCATCCCCTCCTAAAACT-3' (SEQ ID NO: 64) |
| ADAM19 | 5'-CACTTGCCCCAAAGTTTCCA-3' (SEQ ID NO: 54) | 5'-GCCAGACATGCTTCTTCAGG-3' (SEQ ID NO: 65) |
| YES1 | 5'-AGGCAGGAAAAGTTGATGGT-3' (SEQ ID NO: 55) | 5'-AGACACTGAAGACGAAAAGCTG-3' (SEQ ID NO: 66) |
| MIS12 | 5'-TGTGCCAAAGTCACAGGTTTT-3' (SEQ ID NO: 56) | 5'-TGCCATCCAGCTTCTTCAGA-3' (SEQ ID NO: 67) |
| MAP3K7 | 5'-ACAGAGAAAGCAAGAACTAGTTG-3' (SEQ ID NO: 57) | 5'-TTGTCGTTTCTGCTGCTGAC-3' (SEQ ID NO: 68) |
| GAPDH | 5'-GAAGGTGAAGGTCGGAGTCAAC-3' (SEQ ID NO: 58) | 5'-CAGAGTTAAAAGCAGCCCTGGT-3' (SEQ ID NO: 69) |
| SAPS2 | 5'-GCCCAAGAAGAAAGCGATCC-3' (SEQ ID NO: 59) | 5'-GTAAGTCCATCGTGTTGAGCC-3' (SEQ ID NO: 70) |
| SAPS2 Exon M | 5'-GTTTTTTGTGTTTGTAGAAGAAAGC-3' (SEQ ID NO: 60) | 5'-ACTTACCAACAATAAATCCATCGTA-3' (SEQ ID NO: 71) |
| SAPS2 Exon U | 5'-TTTTTTGTGTTTGTAGAAGAAAGTGA-3' (SEQ ID NO: 61) | 5'-ACTTACCAACAATAAATCCATCATA-3' (SEQ ID NO: 72) |
| SAPS2 CpG M | 5'-TTTAGTTTTAGAATTGGGTTCGAAG-3' (SEQ ID NO: 62) | 5'-AACAATACCCAAAACTCATACACG-3' (SEQ ID NO: 73) |
| SAPS2 CPG U | 5'-TAGTTTTAGAATTGGGTTTGAAG-3' (SEQ ID NO: 63) | 5'-AATACCCAAAACTCATACACACTAA-3' (SEQ ID NO: 74) |
| piRNA mimic | Sequence | |
| piR-8041 | 5'-UGAGGCGGGCGCCAUGCAGACGGGCA-3' (SEQ ID NO: 75) | |
| piR-16792 | 5'-CCUCCCAAAGUGCUGGGAUUACAGGCGUGAG-3' (SEQ ID NO: 76) | |
| piR-54022 | 5'-UGGACGGACGGAUGGCCAGAUGAAUCAAAACU-3' (SEQ ID NO: 77) | |
| piR-1047 | 5'-AGGGUAACUAUCAUCAUGUGUCUGGAGGUC-3' (SEQ ID NO 78) | |
| piR-20249 | 5'-GGAUAUGGAAAUGAGAGGACGGACAAGC-3' (SEQ ID NO: 79) | |
| piR-15988 | 5'-UGUGGACUGUCUCAGGAGGCAGAGGGGCACC-3' (SEQ ID NO: 80) | |

[1]M = methylated; U = unmethylated

TABLE 3 piRNAs differentially expressed at least 2-fold in malignant relative to normal brain tissue from piRNA expression profiling

| Accession number | Sequence | Control average signal | Tumor average signal | Fold change |
|---|---|---|---|---|
| DQ573352 | TCAGACATTTGGTGTATGTGCTTGGC (SEQ ID NO: 81) | 623 | 5,158 | +8.28 |
| DQ571823 | ATTTGGTGTATGTGCTTGGCTGAGGAGCCAA (SEQ ID NO: 82) | 1,943 | 13,182 | +6.78 |
| DQ595539 | TTGGTGTATGTGCTTGGCTGAGGAGCC (SEQ ID NO: 83) | 2,608 | 16,400 | +6.29 |
| DQ593270 | CGCACGTGTTAGGACCCGAAAGATGGTGAAC (SEQ ID NO: 84) | 5,140 | 32,133 | +6.25 |
| DQ590404 | TGGTGTATGTGCTTGGCTGAGGAGCCAATGG (SEQ ID NO: 85) | 2,232 | 12,488 | +5.59 |
| DQ574732 | TCCAGGTTCGACTCCTGGCTGGCTCGC (SEQ ID NO: 86) | 551 | 2,931 | +5.32 |
| DQ570812 | AGAGAGGGGCCCGTGCCTTGGAAAGCGTC (SEQ ID NO: 87) | 1,073 | 5,697 | +5.31 |
| DQ581012 | TGAGGGTTCGAGTCCCTTCGTGGTCGCC (SEQ ID NO: 88) | 1,404 | 6,380 | +4.55 |
| DQ588513 | TGGGAAGGAGATGGTCATGTGGCATGAGT (SEQ ID NO: 89) | 2,720 | 12,085 | +4.44 |
| DQ571333 | AGGGGCCCGTGCCTTGGAAAGCGTCGC (SEQ ID NO: 90) | 680 | 2,979 | +4.38 |
| DQ596744 | GAGGGGCCCGTGCCTTGGAAAGCGTCGCG (SEQ ID NO: 91) | 1,060 | 4,477 | +4.22 |
| DQ570513 | ACCGTCGTAGTTCCGACCATAAACGATGCC (SEQ ID NO: 92) | 3,482 | 14,671 | +4.21 |
| DQ598104 | GGGAGATGAAGAGGACAGTGACTGAGAGAC (SEQ ID NO: 93) | 5,523 | 22,086 | +4.00 |
| DQ571549 | ATCAGACCCCAGAAAAGGTGTTGGTTGA (SEQ ID NO: 94) | 2,515 | 9,979 | +3.97 |
| DQ594461 | TTCCGGGTTCGAGTCCCGGCGGAGTCGCC (SEQ ID NO: 95) | 1,114 | 4,049 | +3.64 |
| DQ582231 | CAGACCCCAGAAAAGGTGTTGGTTGAT (SEQ ID NO: 96) | 3,575 | 12,880 | +3.60 |
| DQ596992 | GCAATAACAGGTCTGTGATGCCCTTAGA (SEQ ID NO: 97) | 3,785 | 13,628 | +3.60 |
| DQ571550 | ATCAGACCCCAGAAAAGGTGTTGGTTGAT (SEQ ID NO: 98) | 3,451 | 12,380 | +3.59 |
| DQ596538 | GAGAGGGGCCCGTGCCTTGGAAAGCGTCGCG (SEQ ID NO: 99) | 1,522 | 5,422 | +3.56 |
| DQ584545 | TGCCATGGTAATCCTGCTCAGTACGAGA (SEQ ID NO: 100) | 2,744 | 9,513 | +3.47 |
| DQ572465 | TATTGATGCCGAACTCAGTGCGGACACCCCGT (SEQ ID NO: 101) | 21,156 | 72,873 | +3.44 |
| DQ580854 | TGAGGAGCCAATGGGGCGAAGCTACCATC (SEQ ID NO: 102) | 1,075 | 3,658 | +3.40 |
| DQ572464 | TATTGATGCCGAACTCAGTGCGGACACCCC (SEQ ID NO: 103) | 19,387 | 64,302 | +3.32 |
| DQ598675 | GTTTAGACGGGCTCACATCACCCCATAAACA (SEQ ID NO: 104) | 2,577 | 8,496 | +3.30 |
| DQ596183 | GAATGCAGCCCAAAGCGGGTGGTAAACT (SEQ ID NO: 105) | 5,590 | 18,220 | +3.26 |
| DQ593048 | CCGGCCCGGACACGGACAGGATTGACAGAT (SEQ ID NO: 106) | 5,841 | 18,632 | +3.19 |
| DQ575661 | TCCCTGGTTCGATCCCGGGTTTCGGCACC (SEQ ID NO: 107) | 994 | 3,161 | +3.18 |
| DQ598167 | GGGGCGAAGCTACCATCTGTGGGATT (SEQ ID NO: 108) | 985 | 3,072 | +3.12 |
| DQ577504 | TCTCCATGTAGGAGGGAGTATGGTGTTTC (SEQ ID NO: 109) | 4,922 | 15,092 | +3.07 |
| DQ598103 | GGGAGATGAAGAGGACAGTGACTGAGAGA (SEQ ID NO: 110) | 10,521 | 32,140 | +3.05 |
| DQ600105 | TACCACTCAGTGATGGAGGGAGACTGTGC (SEQ ID NO: 111) | 4,225 | 12,852 | +3.04 |
| DQ592970 | CCCGGCCCGGACACGGACAGGATTGACAGATT (SEQ ID NO: 112) | 7,233 | 21,883 | +3.03 |
| DQ588594 | TGGGAATGCAGCCCAAAGCGGGTGGTA (SEQ ID NO: 113) | 9,913 | 28,697 | +2.89 |
| DQ570926 | AGCAGGACGGTGGCCATGGAAGTCGGAATCC (SEQ ID NO: 114) | 3,657 | 10,585 | +2.89 |
| DQ598273 | GGTCGCTGGTTCGAATCCGGCTCGAAGGACC (SEQ ID NO: 115) | 1,125 | 3,209 | +2.85 |
| DQ570339 | ACAGGTCTGTGATGCCCTTAGATGTCCGG (SEQ ID NO 116) | 3,519 | 9,893 | +2.81 |
| DQ594983 | TTGATGCCGAACTCAGTGCGGACACCCCGTC (SEQ ID NO: 117) | 13,731 | 37,945 | +2.76 |

TABLE 3-continued piRNAs differentially expressed at least 2-fold in malignant relative to normal brain tissue from piRNA expression profiling

| Accession number | Sequence | Control average signal | Tumor average signal | Fold change |
|---|---|---|---|---|
| DQ593837 | CTGGGAATGCAGCCCAAAGCGGGTGGTAA (SEQ ID NO: 118) | 9,338 | 25,728 | +2.76 |
| DQ573683 | TCAGTGATGGAGGGAGACTGTGCCCCAA (SEQ ID NO: 119) | 8,416 | 22,650 | +2.69 |
| DQ591113 | TGTCCTCATAAGGAGAGGGAGATTTGAGC (SEQ ID NO: 120) | 12,238 | 32,336 | +2.64 |
| DQ596531 | GAGAGAGGGGCCCGTGCCTTGGAAAGTG (SEQ ID NO: 121) | 1,021 | 2,683 | +2.63 |
| DQ573097 | TCACCCGGCCCGGACACGGACAGGATTGACA (SEQ ID NO: 122) | 9,017 | 23,647 | +2.62 |
| DQ589647 | TGGGTGTTTCTCGCAGAGGGGGATTTGGC (SEQ ID NO: 123) | 1,426 | 3,730 | +2.62 |
| DQ584904 | TGCCTAGTGGGCCACTTTTGGTAAGCAGAA (SEQ ID NO: 124) | 5,330 | 13,882 | +2.60 |
| DQ576918 | TCGCTGGTTCGATTCCGGCTCGAAGGAC (SEQ ID NO: 125) | 1,002 | 2,565 | +2.56 |
| DQ591302 | TGTGAACTGAGACAGAGGGAGATAAAGCC (SEQ ID NO: 126) | 3,297 | 8,153 | +2.47 |
| DQ589262 | TGGGGAGATTCCCGTGGGAAATGGGA (SEQ ID NO: 127) | 13,046 | 32,161 | +2.47 |
| DQ574632 | TCCAGGAGGGAAATGAAATGACCTTGGCA (SEQ ID NO: 128) | 1,044 | 2,548 | +2.44 |
| DQ588691 | TGGGAGAATACATACGTTGCTGGCGGG (SEQ ID NO: 129) | 1,518 | 3,699 | +2.44 |
| DQ571272 | AGGGAAATTGCCATAGGACAGGTTTGGG (SEQ ID NO: 130) | 6,799 | 16,556 | +2.43 |
| DQ593311 | CGCTGGTTCGATTCCGGCTCGAAGGAC (SEQ ID NO: 131) | 1,225 | 2,965 | +2.42 |
| DQ588512 | TGGGAAGGAGATGGTCATGTGGCATGAGA (SEQ ID NO: 132) | 4,966 | 12,022 | +2.42 |
| DQ594964 | TTGATAGATGAAGATGGGAAGGAGATGG (SEQ ID NO: 133) | 3,201 | 7,632 | +2.38 |
| DQ598263 | GGTCAGTCGGTCCTGAGAGATGGGCGAGC (SEQ ID NO: 134) | 2,676 | 6,310 | +2.36 |
| DQ584096 | TGCCAAACTTAGTGCGGGCACCCGGTCGGC (SEQ ID NO: 135) | 2,918 | 6,874 | +2.36 |
| DQ572289 | TATGCCAGGAGGGAGGTTGACCCGCCAGGTC (SEQ ID NO: 136) | 5,844 | 13,752 | +2.35 |
| DQ571067 | AGCTGGAGTGCAGTGGTGCGATCACGGC (SEQ ID NO: 137) | 3,481 | 8,094 | +2.33 |
| DQ573083 | TCACCCAGGCTAGAGTGCAGTGGTGCA (SEQ ID NO: 138) | 22,062 | 51,125 | +2.32 |
| DQ598127 | GGGCAGAAGTTGGGTGTCAGTGATGGGA (SEQ ID NO: 139) | 4,592 | 10,489 | +2.28 |
| DQ590455 | TGGTGTGATCTCGGCTCACTGCAACCTCCT (SEQ ID NO: 140) | 1,310 | 2,982 | +2.28 |
| DQ601565 | TAGGCAAGAAGGAAGGGAGAAGACACAAGC (SEQ ID NO: 141) | 4,515 | 10,153 | +2.25 |
| DQ571270 | AGGGAAAGACAGGTTTTGGATAAGGGG (SEQ ID NO: 142) | 5,101 | 11,080 | +2.17 |
| DQ592292 | TGTTGATAGATGAAGATGGGAAGGAGATGT (SEQ ID NO: 143) | 3,914 | 8,476 | +2.17 |
| DQ584397 | TGCCAGGAGGGAGGTTGACCCGCCAGGTCC (SEQ ID NO: 144) | 4,113 | 8,788 | +2.14 |
| DQ594933 | TTGAGGAACTGAAACGACAGGAGGGCGA (SEQ ID NO: 145) | 1,695 | 3,578 | +2.11 |
| DQ586610 | TGGAAGCTCAGGTGTGAGGGAGACTCAGAA (SEQ ID NO: 146) | 1,865 | 3,906 | +2.09 |
| DQ591777 | TGTGCTGGGAGGAGAGTCTAACTGTAAC (SEQ ID NO: 147) | 2,372 | 4,927 | +2.08 |
| DQ580320 | TGAGAGAGGGAGACTCTGTGCACTCC (SEQ ID NO: 148) | 4,005 | 8,278 | +2.07 |
| DQ598310 | GGTTAGTTTTACCCTACTGATGATGTGTTGTT (SEQ ID NO: 149) | 4,348 | 8,938 | +2.06 |
| DQ589327 | TGGGGGAGACACTTAATGCAAAACGCAAGAAT (SEQ ID NO: 150) | 7,507 | 15,276 | +2.03 |
| DQ583328 | TGCAATGGTCTAGGGGGAGAAAACTCACTC (SEQ ID NO: 151) | 9,834 | 19,956 | +2.03 |
| DQ571408 | AGGTTAGTTTTACCCTACTGATGATGTGTT (SEQ ID NO: 152) | 2,302 | 4,671 | +2.03 |
| DQ571091 | AGGAAAGGCAAAGGGAAGAGAGATGC (SEQ ID NO: 153) | 1,241 | 2,514 | +2.03 |

TABLE 3-continued piRNAs differentially expressed at least 2-fold in malignant relative to normal brain tissue from piRNA expression profiling

| Accession number | Sequence | Control average signal | Tumor average signal | Fold change |
|---|---|---|---|---|
| DQ596374 | GACGAGGTGGCCGAGTGGTTAAGGCAATGGA (SEQ ID NO: 154) | 10,629 | 5,283 | -2.01 |
| DQ582108 | CACCTTGGGAGGCCAAGGCAGGCAGATCATC (SEQ ID NO: 155) | 3,037 | 1,494 | -2.03 |
| DQ596373 | GACGAGGTGGCCGAGTGGTTAAGGCAATGG (SEQ ID NO: 156) | 10,074 | 4,952 | -2.03 |
| DQ596624 | GAGCGGGAAGAGACTGGAGATGAGGA (SEQ ID NO: 157) | 3,698 | 1,814 | -2.04 |
| DQ579739 | TGACCCCAGGAGGCGGAAGTTGCAGTGAGC (SEQ ID NO: 158) | 2,457 | 1,201 | -2.05 |
| DQ598189 | GGGGGTGTAGCTCAGTGGTAGAGCGCGTGCT (SEQ ID NO: 159) | 6,969 | 3,341 | -2.09 |
| DQ591422 | TGTGACGTCAGGTGAGAAGGGAGGGCCCGT (SEQ ID NO: 160) | 2,639 | 1,265 | -2.09 |
| DQ571989 | TAGTTGGGTGCAAGGCTGGGGTGGGCGGG (SEQ ID NO: 161) | 16,151 | 7,632 | -2.12 |
| DQ598055 | GGGAAAGATACGGTCCTCATGAGGAGGGG (SEQ ID NO: 162) | 16,588 | 7,781 | -2.13 |
| DQ587132 | TGGAGGCGGGGATGAGTGTGAATTTA (SEQ ID NO: 163) | 1,976 | 926 | -2.13 |
| DQ599236 | TAAGAAGTGGGTGGGTGGGAGGAGAAAGAGC (SEQ ID NO: 164) | 16,364 | 7,637 | -2.14 |
| DQ575255 | TCCCAGTATAGGGTTGGAGGAGGAGCTTA (SEQ ID NO: 165) | 1,843 | 853 | -2.16 |
| DQ580937 | TGAGGCCTAGCAAAGGGTGGAGGGTGGGAG (SEQ ID NO: 166) | 23,342 | 10,702 | -2.18 |
| DQ598159 | GGGGATGTAGCTCAGTGGTAGAGCGCATGCT (SEQ ID NO: 167) | 13,709 | 6,214 | -2.21 |
| DQ598131 | GGGCATTGGAGGGACAATTTGGAAGGG (SEQ ID NO: 168) | 4,248 | 1,918 | -2.22 |
| DQ572620 | TCAAATAGGAACCAGGAGTACGGGAGGAGC (SEQ ID NO: 169) | 3,457 | 1,557 | -2.22 |
| DQ598188 | GGGGGTGTAGCTCAGTGGTAGAGCGCGTGC (SEQ ID NO: 170) | 7,091 | 3,186 | -2.23 |
| DQ598177 | GGGGGGTGTAGCTCAGTGGTAGAGCGCGTGCT (SEQ ID NO: 171) | 8,025 | 3,593 | -2.23 |
| DQ571031 | AGCGTTGGTGGTATAGTGGTGAGCATAGCTGC (SEQ ID NO: 172) | 9,927 | 4,437 | -2.24 |
| DQ596696 | GAGGAGGAGAACAGGGGTCCTGGTGGTC (SEQ ID NO: 173) | 2,127 | 948 | -2.24 |
| DQ593327 | CGGAAGGTCCTGGAAGAAGGGCGGGAGAGA (SEQ ID NO: 174) | 31,055 | 13,822 | -2.25 |
| DQ574893 | TCCATGGGGTGGGGGGTGAGTCACAGCA (SEQ ID NO: 175) | 28,348 | 12,534 | -2.26 |
| DQ596048 | GAACAAGGGAAGAGTGGGCGTGGAGGG (SEQ ID NO: 176) | 20,983 | 9,259 | -2.27 |
| DQ588632 | TGGGACAGGAGGCACTGGGGTGGGTGGA (SEQ ID NO: 177) | 5,740 | 2,527 | -2.27 |
| DQ570814 | AGAGATAGCAGAGTGGCGCAGCGGAAGC (SEQ ID NO: 178) | 3,185 | 1,394 | -2.29 |
| DQ596689 | GAGGAGCCACATGTCCTTATGGGGAGAGA (SEQ ID NO: 179) | 44,781 | 19,572 | -2.29 |
| DQ585360 | TGCGGTGAGGGGCGGAGCTGGAACCTCGG (SEQ ID NO: 180) | 1,597 | 692 | -2.31 |
| DQ598176 | GGGGGGTGTAGCTCAGTGGTAGAGCGCGTGC (SEQ ID NO: 181) | 9,700 | 4,176 | -2.32 |
| DQ571030 | AGCGTTGGTGGTATAGTGGTGAGCATAGC (SEQ ID NO: 182) | 9,241 | 3,971 | -2.33 |
| DQ598240 | GGGTTTGGGGTGGATGGAGGGTGTGGGATGGA (SEQ ID NO: 183) | 4,774 | 2,050 | -2.33 |
| DQ597216 | GCATTGGTGGTATAGTGGTGAGCATA (SEQ ID NO: 184) | 5,038 | 2,134 | -2.36 |
| DQ598190 | GGGGGTGTAGCTCAGTGGTAGAGCGCGTGCTT (SEQ ID NO: 185) | 7,775 | 3,284 | -2.37 |
| DQ576697 | TCCTTGGGCAGGGGAAGGGCAGCACC (SEQ ID NO: 186) | 4,992 | 2,100 | -2.38 |
| DQ590830 | TGTAGTCGTGGCCGAGTGGTTAAGGC (SEQ ID NO: 187) | 2,819 | 1,177 | -2.40 |
| DQ570091 | AAGAGCTGCAGGGGAACTGGGAGAGGGT (SEQ ID NO: 188) | 10,084 | 4,195 | -2.40 |
| DQ601502 | TAGGAGGATGACATGGAGGAGGACGACGA (SEQ ID NO: 189) | 2,340 | 967 | -2.42 |
| DQ587670 | TGGCAGTGAGCTGGGCAGGGAGGAAGGGGT (SEQ ID NO: 190) | 56,770 | 23,180 | -2.45 |

TABLE 3-continued piRNAs differentially expressed at least 2-fold in malignant relative to normal brain tissue from piRNA expression profiling

| Accession number | Sequence | Control average signal | Tumor average signal | Fold change |
|---|---|---|---|---|
| DQ584284 | TGCCACGCCAATGGGAGGACACAGGTGGGCGG (SEQ ID NO: 191) | 4,462 | 1,819 | -2.45 |
| DQ596730 | GAGGCTGAAGCTGGATAGGGAGGTCGG (SEQ ID NO: 192) | 6,506 | 2,628 | -2.48 |
| DQ597033 | GCACAGGTGAAAGTGGCCGAGGTGGAGGGC (SEQ ID NO: 193) | 3,309 | 1,327 | -2.49 |
| DQ588631 | TGGGACAGGAGGCACTGGGGTGGGTGAA (SEQ ID NO: 194) | 2,594 | 1,036 | -2.50 |
| DQ597215 | GCATTGGTGGTATAGTGGTAAGCATAGC (SEQ ID NO: 195) | 2,374 | 945 | -2.51 |
| DQ572571 | TCAAAGCCTGATGCAGAAGGAAGGAGGGGT (SEQ ID NO: 196) | 5,073 | 2,014 | -2.52 |
| DQ572857 | TCAATTCTGTAGAGTCAGGGGTGAGGAGGA (SEQ ID NO: 197) | 2,071 | 809 | -2.56 |
| DQ588514 | TGGGAAGGAGGAGGACAAGCAGAGCTGGG (SEQ ID NO: 198) | 16,508 | 6,436 | -2.56 |
| DQ572813 | TCAATAAGGGTGGAAGCGACGGGGAAAGA (SEQ ID NO: 199) | 1,804 | 703 | -2.57 |
| DQ597217 | GCATTGGTGGTATAGTGGTGAGCATAGC (SEQ ID NO: 200) | 6,986 | 2,696 | -2.59 |
| DQ590798 | TGTAGAGATAAAGCTGAGGAGGAGGC (SEQ ID NO: 201) | 2,952 | 1,120 | -2.63 |
| DQ571029 | AGCGTTGGTGGTATAGTGGTGAGCATA (SEQ ID NO: 202) | 8,210 | 3,099 | -2.65 |
| DQ597767 | GGAGAGGGTGTGGGGGGCGTGTGGGATGTC (SEQ ID NO: 203) | 18,667 | 6,983 | -2.67 |
| DQ588489 | TGGGAAGAGAGAGCAAGGAGCTGGAGGG (SEQ ID NO: 204) | 23,735 | 8,754 | -2.71 |
| DQ578685 | TGAAATGGACAGGAAGGGTGGGCGGGCCT (SEQ ID NO: 205) | 16,830 | 6,196 | -2.72 |
| DQ598997 | TAACAAGTACGGGGAAGAGAGGGTGATC (SEQ ID NO: 206) | 6,678 | 2,448 | -2.73 |
| DQ578686 | TGAAATGGACAGGAAGGGTGGGCGGGCCTT (SEQ ID NO: 207) | 13,907 | 5,052 | -2.75 |
| DQ598375 | GTAGTCGTGGCCGAGTGGTTAAGGCTATGGA (SEQ ID NO: 208) | 1,936 | 701 | -2.76 |
| DQ595434 | TTGGGGAAGACACGGACGGGGCCCAGACC (SEQ ID NO: 209) | 6,806 | 2,447 | -2.78 |
| DQ576177 | TCCTCAGCATCGGTGAGAAGGGGCGGC (SEQ ID NO: 210) | 12,202 | 4,247 | -2.87 |
| DQ588872 | TGGGATGAGAAGTCTGGAGGGCACGG (SEQ ID NO: 211) | 2,286 | 786 | -2.91 |
| DQ599789 | TACACAGAACGAACGGGGCAGAGAGGTGG (SEQ ID NO: 212) | 3,055 | 985 | -3.10 |
| DQ579061 | TGAAGGAACTGAGGGGCAGGGAAAGA (SEQ ID NO: 213) | 6,869 | 2,156 | -3.19 |
| DQ598641 | GTTAAGATGGCAGAGCCCGGTAATCGCATAA (SEQ ID NO: 214) | 1,543 | 443 | -3.48 |
| DQ598225 | GGGTGGAAGCGATGAGTTCTCCAGGGGC (SEQ ID NO: 215) | 4,990 | 1,424 | -3.50 |
| DQ570976 | AGCCATAAATACAACGCAGGGGGCC (SEQ ID NO: 216) | 6,686 | 1,748 | -3.83 |
| DQ581919 | CAAGAGTTCGGGGAAAGACGGACAGGAC (SEQ ID NO: 217) | 2,881 | 749 | -3.85 |
| DQ572471 | TATTGGACTGAACAAAGGGGGGCAAACAC (SEQ ID NO: 218) | 2,667 | 684 | -3.90 |
| DQ599788 | TACACAGAACGAACGGGGCAGAGAGGTG (SEQ ID NO: 219) | 2,339 | 598 | -3.91 |
| DQ597566 | GCTGAGGAAGAGTGGACGGACGGATGGCA (SEQ ID NO: 220) | 22,672 | 5,475 | -4.14 |
| DQ582069 | CACCAGGGGGTAGGGCCCAAAGGGA (SEQ ID NO: 221) | 14,763 | 3,401 | -4.34 |
| DQ597805 | GGATATGGAAATGAGAGGACGGACAAGC (SEQ ID NO: 222) | 1,380 | 261 | -5.29 |
| DQ591832 | TGTGGACTGTCTCAGGAGGCAGAGGGGCACC (SEQ ID NO: 223) | 4,483 | 789 | -5.68 |
| DQ586910 | TGGACGGACGGATGGCCAGATGAATCAAAACT (SEQ ID NO: 224) | 1,370 | 215 | -6.38 |
| DQ580941 | TGAGGCGGGCGCCATGCAGACGGGCA (SEQ ID NO: 225) | 2,385 | 231 | -10.32 |

TABLE 4

A table for summary of top-3 identified piRNAs embedded SNPs that are associated with lung cancer risk.

| SNP | piRNAs[1] | Position | Minor/Common Allele | MAF (cases/controls) | OR[2] | 95% CI | Nominal P-value | FDR P-value[3] |
|---|---|---|---|---|---|---|---|---|
| rs11639347 | piR-5247 piR-5671 | Chr15: 79024350 | T/C | 0.41/0.38 | 1.17 | (1.09, 1.27) | 3.560E−05 | 0.042 |
| rs13382748 | piR-21626 | Chr2: 95450931 | C/T | 0.11/0.10 | 1.26 | (1.12, 1.43) | 2.190E−04 | 0.257 |
| rs60534722 | piR-16828 | Chr12: 24554473 | A/G | 0.17/9.19 | 0.85 | (0.77, 0.94) | 1.498E−03 | 1.757 |

[1]Identified SNPs are located within the genome loci of the piRNAs;
[2]Odds ratio for the minor allele associated with lung cancer;
[3]Bonferroni-correction for 1173 comparisons.

TABLE 5

A table for summary data of top-7 identified piRNAs from the expression analysis.

| piRNAs[1] | Name | Position | Strand | Gene[2] | Mean-Normal[3] | Mean-Tumor[4] | Nominal P-Value | FDR P-Value[5] |
|---|---|---|---|---|---|---|---|---|
| FR043670 | piR-14620 | Chr5: 93905174-93905200 | − | Intron of KIAA0825 | 486.94 | 1025.32 | 6.280E−05 | 0.001 |
| FR090905 | piR-20009 | Chr7: 145694484-145694511 | + | Intergenic | 389.33 | 711.72 | 0.047 | 9.391 |
| FR082269 | piR-31637 | ChrM: 619-650 | + | Intergenic | 358.28 | 149.19 | 0.005 | 1.090 |
| FR205579 | piR-2732 | Chr22: 39709883-39709914 | − | Intron of RPL3 | 26.71 | 140.45 | 1.06E−18 | 2.120E−16 |
| FR038165 | piR-51809 | Chr8: 68497704-68497734 | − | Intron of CPA6 | 3.22 | 59.26 | 2.300E−16 | 4.610E−14 |
| FR111727 | piR-19521 | Chr11: 10530940-10530967 | − | Intergenic | 6.07 | 48.22 | 6.540E−23 | 1.310E−20 |
| FR197889 | piR-15232 | Chr6: 27100537-27100567 | + | Exon of HIST1H2BJ | 4.56 | 40.98 | 5.720E−41 | 1.140E−38 |

[1]piRNAs name used in the scientific report;
[2]The genome region where piRNAs are located;
[3,4]The mean expression level (RPKM) of tumor and control samples.
[5]Bonferroni-correction for 200 comparisons.

TABLE 11

Primers used for qPCR reactions and piRNA mimics used for in vitro functional analyses.

| Amplification target | Forward Primer | Reverse Primer |
|---|---|---|
| piR-598 | 5'-CTAGCTAAGATCATTGATGAAGG-3' (SEQ ID NO: 226) | Universal |
| piR-2799 | 5'-CAGCTATGAAGTCTATGAATCC-3' (SEQ ID NO: 227) | Universal |
| piR-3266 | 5'-CTCCAGTAGTATCCTCTGTTTTC-3' (SEQ ID NO: 228) | Universal |
| piR-11714 | 5'-TGCTGAAGTTTGCTGCTG-3' (SEQ ID NO: 229) | Universal |
| piR-18913 | 5'-TGGATTGAAGGACGCAAAGTT-3' (SEQ ID NO: 230) | Universal |
| snRNA U6 | 5'-ACGCAAATTCGTGAAGCGTT-3' (SEQ ID NO: 231) | Universal |
| BAX | 5'-TTCATCCAGGATCGAGCAGG-3' (SEQ ID NO: 232) | 5'-GCAATCATCCTCTGCAGCTC-3' (SEQ ID NO: 238) |
| HSPA1B | 5'-ACGGCAAGGTGGAGATCATC-3' (SEQ ID NO: 233) | 5'-GCTTGTCTCCGTCGTTGATC-3' (SEQ ID NO: 239) |
| JUN | 5'-AGCAGCAAAGAACTTTCCCG-3' (SEQ ID NO: 234) | 5'-CACGTCCTTCTTCTCTTGCG-3' (SEQ ID NO: 240) |
| SMAD4 | 5'-GCTATCAGTCTGTCAGCTGC-3' (SEQ ID NO: 235) | 5'-CTTCGTCTAGGAGCTGGAGG-3' (SEQ ID NO: 241) |
| YY1 | 5'-GTTCAGGGATAACTCGGCCA-3' (SEQ ID NO: 236) | 5'-TTCGAACGTGCACTGAAAGG-3' (SEQ ID NO: 242) |
| GAPDH | 5'-GAAGGTGAAGGTCGGAGTCAAC-3' (SEQ ID NO: 237) | 5'-CAGAGTTAAAAGCAGCCCTGGT-3' (SEQ ID NO: 243) |

TABLE 11-continued

Primers used for qPCR reactions and piRNA mimics used for in vitro functional analyses.

| Amplification target | Forward Primer | Reverse Primer |
|---|---|---|
| piR-598 (Wild-type) | 5'-AGAAGAUCUAGCUAAGAUCAUUGAUGAAGGU-3' (SEQ ID NO: 48) | |
| piR-598 (Variant) | 5'-AGAAGAUCUAGCUAAGAUCAUUGAUGAAAGU-3' (SEQ ID NO: 244) | |

I claim:

1. A method of treating a subject for liver cancer comprising administering the subject an effective amount of a pharmaceutical composition comprising a compound that increases the level of piR-37213 or a mimic thereof in cells of the liver cancer.

2. The method of claim 1, wherein the compound is wildtype piR-37213 or a close variant thereof with the same or similar activity to wildtype, or a stimulator of expression thereof.

3. The method of claim 1, wherein piR-37213 is underexpressed in the cancer relative to normal tissue.

4. The method of claim 1, wherein the liver cancer is hepatocellular carcinoma (HCC), fibrolamellar carcinoma, cholangiocarcinoma, angiosarcoma, or hepatoblastoma.

5. The method of claim 1, wherein the compound is a nucleic acid comprising the nucleic acid sequence of wildtype piR-37213.

6. The method of claim 1, wherein the compound is incorporated into or encapsulated by nanoparticles, microparticles, micelles, synthetic lipoprotein particles, or carbon nanotubes.

7. The method of claim 1, wherein the compound is incorporated into or encapsulated by liposomes.

8. The method of claim 1, wherein the pharmaceutical composition is administered parenterally, orally, or topically.

9. The method of claim 1, wherein the pharmaceutical composition is administered systemically.

10. The method of claim 1, wherein the pharmaceutical composition is administered locally.

11. The method of claim 1, further comprising administering the subject one or more additional therapeutic agents.

12. The method of claim 1, wherein the compound is a nucleic acid encoding wildtype piR-37213, wildtype piR-37213, or a piR-37213 mimic.

13. A method of treating a subject for liver cancer comprising administering the subject an effective amount of a pharmaceutical composition comprising a compound selected from a nucleic acid encoding wildtype piR-37213, wildtype piR-37213, or a piR-37213 mimic.

14. The method of claim 13, wherein the compound is wildtype piR-37213 or a piR-37213 mimic.

15. The method of claim 13, wherein the compound is incorporated into or encapsulated by nanoparticles, microparticles, micelles, synthetic lipoprotein particles, or carbon nanotubes.

16. The method of claim 13, wherein the compound is incorporated into or encapsulated by liposomes.

17. The method of claim 13, wherein piR-37213 is underexpressed in the cancer relative to normal tissue.

18. The method of claim 13, wherein the liver cancer is hepatocellular carcinoma.

19. A method of treating a subject for liver cancer comprising administering the subject an effective amount of a pharmaceutical composition comprising wildtype piR-37213 or a mimic thereof incorporated into or encapsulated by liposomes.

20. The method of claim 19, wherein piR-37213 is underexpressed in the cancer relative to normal tissue, the liver cancer is hepatocellular carcinoma, or a combination thereof.

* * * * *

SEQUENCE LISTING

<160> NUMBER OF SEQ ID NOS: 244

<210> SEQ ID NO 1
<211> LENGTH: 26
<212> TYPE: DNA
<213> ORGANISM: Homo sapiens

<400> SEQUENCE: 1
tcaaagagaa ggggtcctag atgttc                                      26

<210> SEQ ID NO 2
<211> LENGTH: 29
<212> TYPE: DNA
<213> ORGANISM: Homo sapiens

<400> SEQUENCE: 2
tgggaatgtg acccgcgaat attgttgcc                                   29

<210> SEQ ID NO 3
<211> LENGTH: 31
<212> TYPE: DNA
<213> ORGANISM: Homo sapiens

<400> SEQUENCE: 3
acactgcaat gagccagtca aatgggagtt c                                31

<210> SEQ ID NO 4
<211> LENGTH: 28
<212> TYPE: DNA
<213> ORGANISM: Homo sapiens

<400> SEQUENCE: 4
tgatagtcac acagacaggc cttcatga                                    28

<210> SEQ ID NO 5
<211> LENGTH: 30
<212> TYPE: DNA
<213> ORGANISM: Homo sapiens

<400> SEQUENCE: 5
tcacagcatg gagcgtcacg atagggatc                                   30

<210> SEQ ID NO 6
<211> LENGTH: 26
<212> TYPE: DNA
<213> ORGANISM: Homo sapiens

<400> SEQUENCE: 6
tgaggcgggc gccatgcaga cgggca                                      26

<210> SEQ ID NO 7
<211> LENGTH: 32
<212> TYPE: DNA
<213> ORGANISM: Homo sapiens

<400> SEQUENCE: 7
tggacggacg gatggccaga tgaatcaaaa ct         32

<210> SEQ ID NO 8
<211> LENGTH: 28
<212> TYPE: DNA
<213> ORGANISM: Homo sapiens

<400> SEQUENCE: 8
ggatatggaa atgagaggac ggacaagc              28

<210> SEQ ID NO 9
<211> LENGTH: 31
<212> TYPE: DNA
<213> ORGANISM: Homo sapiens

<400> SEQUENCE: 9
tgtggactgt ctcaggaggc agaggggcac c          31

<210> SEQ ID NO 10
<211> LENGTH: 31
<212> TYPE: DNA
<213> ORGANISM: Homo sapiens

<400> SEQUENCE: 10
taacgccaag gtcgcgggtt cgaaccccgt a          31

<210> SEQ ID NO 11
<211> LENGTH: 26
<212> TYPE: DNA
<213> ORGANISM: Homo sapiens

<400> SEQUENCE: 11
tggatgtctg cctctactaa ctggga                26

<210> SEQ ID NO 12
<211> LENGTH: 31
<212> TYPE: DNA
<213> ORGANISM: Homo sapiens

<400> SEQUENCE: 12
cgccatcttc agcaaaccct gatgaaggct a          31

<210> SEQ ID NO 13
<211> LENGTH: 26
<212> TYPE: DNA
<213> ORGANISM: Homo sapiens

<400> SEQUENCE: 13
tgtatgtgtt ccaatgttta gtcggc                26

<210> SEQ ID NO 14
<211> LENGTH: 27
<212> TYPE: DNA
<213> ORGANISM: Homo sapiens

<400> SEQUENCE: 14
tcaagtgttt tggttcaatg aatggtc               27

<210> SEQ ID NO 15
<211> LENGTH: 31
<212> TYPE: DNA
<213> ORGANISM: Homo sapiens

<400> SEQUENCE: 15
tctgatctac catcattgtt taatgttcgg c					31

<210> SEQ ID NO 16
<211> LENGTH: 30
<212> TYPE: DNA
<213> ORGANISM: Homo sapiens

<400> SEQUENCE: 16
tgcactgaca tggaccccga gccgcagacc					30

<210> SEQ ID NO 17
<211> LENGTH: 30
<212> TYPE: DNA
<213> ORGANISM: Homo sapiens

<400> SEQUENCE: 17
tgcatgtgga gacgcagatg cctgacaaag					30

<210> SEQ ID NO 18
<211> LENGTH: 28
<212> TYPE: DNA
<213> ORGANISM: Homo sapiens

<400> SEQUENCE: 18
tctggcaagg acggcttggt gtgcacgc					28

<210> SEQ ID NO 19
<211> LENGTH: 30
<212> TYPE: DNA
<213> ORGANISM: Homo sapiens

<400> SEQUENCE: 19
tggcttttgt agaatgtagg tcttcactgt					30

<210> SEQ ID NO 20
<211> LENGTH: 29
<212> TYPE: DNA
<213> ORGANISM: Homo sapiens

<400> SEQUENCE: 20
tgtgaatgaa tcgcctttgt cttgttggt					29

<210> SEQ ID NO 21
<211> LENGTH: 29
<212> TYPE: DNA
<213> ORGANISM: Homo sapiens

<400> SEQUENCE: 21
tggaacagga aagaaagcca agacctgta					29

<210> SEQ ID NO 22
<211> LENGTH: 29
<212> TYPE: DNA
<213> ORGANISM: Homo sapiens

<400> SEQUENCE: 22
tccattaggg tcctgctggg atggagtgt					29

<210> SEQ ID NO 23
<211> LENGTH: 29
<212> TYPE: DNA
<213> ORGANISM: Homo sapiens

<400> SEQUENCE: 23
tccccatgac tcaatcaagg actgtgcta					29

<210> SEQ ID NO 24
<211> LENGTH: 26
<212> TYPE: DNA
<213> ORGANISM: Homo sapiens

<400> SEQUENCE: 24
tgcctaagat gattgagttc ccgagg					26

<210> SEQ ID NO 25
<211> LENGTH: 29
<212> TYPE: DNA
<213> ORGANISM: Homo sapiens

<400> SEQUENCE: 25
tggtaacagt gtgcaaagct ctagggtga					29

<210> SEQ ID NO 26
<211> LENGTH: 26
<212> TYPE: DNA
<213> ORGANISM: Homo sapiens

<400> SEQUENCE: 26
tagcttcgat cgttcgaatt cagagc					26

<210> SEQ ID NO 27
<211> LENGTH: 27
<212> TYPE: DNA
<213> ORGANISM: Homo sapiens

<400> SEQUENCE: 27
tatttcagga atgcaagaag gtggttc					27

<210> SEQ ID NO 28
<211> LENGTH: 30
<212> TYPE: DNA
<213> ORGANISM: Homo sapiens

<400> SEQUENCE: 28
tggggaatct gatcgcctgt atcctacctc					30

<210> SEQ ID NO 29
<211> LENGTH: 27
<212> TYPE: DNA
<213> ORGANISM: Homo sapiens

<400> SEQUENCE: 29
tgcctatgtg gtgtttggca aaacatg					27

<210> SEQ ID NO 30
<211> LENGTH: 32
<212> TYPE: DNA
<213> ORGANISM: Homo sapiens

<400> SEQUENCE: 30

|  |  |
|---|---|
| tggagagatt attacatact tgccttttct gc | 32 |

<210> SEQ ID NO 31
<211> LENGTH: 27
<212> TYPE: DNA
<213> ORGANISM: Homo sapiens

<400> SEQUENCE: 31

|  |  |
|---|---|
| tgaagtcaac gtacatggta gcagagt | 27 |

<210> SEQ ID NO 32
<211> LENGTH: 27
<212> TYPE: DNA
<213> ORGANISM: Homo sapiens

<400> SEQUENCE: 32

|  |  |
|---|---|
| tggaaaaaac gccgaaactg atggccc | 27 |

<210> SEQ ID NO 33
<211> LENGTH: 29
<212> TYPE: DNA
<213> ORGANISM: Homo sapiens

<400> SEQUENCE: 33

|  |  |
|---|---|
| tcacgtccag tttgatctgg tggatgtgt | 29 |

<210> SEQ ID NO 34
<211> LENGTH: 27
<212> TYPE: DNA
<213> ORGANISM: Homo sapiens

<400> SEQUENCE: 34

|  |  |
|---|---|
| tggaagtgga tttccggtga aggatgg | 27 |

<210> SEQ ID NO 35
<211> LENGTH: 26
<212> TYPE: DNA
<213> ORGANISM: Homo sapiens

<400> SEQUENCE: 35

|  |  |
|---|---|
| tgggatgaga agtctggagg gcacgg | 26 |

<210> SEQ ID NO 36
<211> LENGTH: 30
<212> TYPE: DNA
<213> ORGANISM: Homo sapiens

<400> SEQUENCE: 36

|  |  |
|---|---|
| tggcgcacga tgtagggcac cttggacctc | 30 |

<210> SEQ ID NO 37
<211> LENGTH: 27
<212> TYPE: DNA
<213> ORGANISM: Homo sapiens

<400> SEQUENCE: 37

|  |  |
|---|---|
| tggacccagt catggacctg ttagtgc | 27 |

<210> SEQ ID NO 38
<211> LENGTH: 27
<212> TYPE: DNA
<213> ORGANISM: Homo sapiens

<400> SEQUENCE: 38

```
tgggccctcc cctagagtgt tcctgca                                          27

<210> SEQ ID NO 39
<211> LENGTH: 26
<212> TYPE: DNA
<213> ORGANISM: Homo sapiens

<400> SEQUENCE: 39
tgggtgttgc ccaattggtg gccaac                                           26

<210> SEQ ID NO 40
<211> LENGTH: 26
<212> TYPE: DNA
<213> ORGANISM: Homo sapiens

<400> SEQUENCE: 40
acacacactt gattgttctg gatgaa                                           26

<210> SEQ ID NO 41
<211> LENGTH: 31
<212> TYPE: DNA
<213> ORGANISM: Homo sapiens

<400> SEQUENCE: 41
agcattggtg gttcagtggt agaattctcg c                                     31

<210> SEQ ID NO 42
<211> LENGTH: 29
<212> TYPE: DNA
<213> ORGANISM: Homo sapiens

<400> SEQUENCE: 42
catctgtgca gtgcaagtga tccacgcct                                        29

<210> SEQ ID NO 43
<211> LENGTH: 28
<212> TYPE: DNA
<213> ORGANISM: Homo sapiens

<400> SEQUENCE: 43
tcagatgcca gccaaaggtt tgtggatc                                         28

<210> SEQ ID NO 44
<211> LENGTH: 27
<212> TYPE: DNA
<213> ORGANISM: Homo sapiens

<400> SEQUENCE: 44
agagagtaca atggtggtta ccagaga                                          27

<210> SEQ ID NO 45
<211> LENGTH: 26
<212> TYPE: DNA
<213> ORGANISM: Homo sapiens

<400> SEQUENCE: 45
tgcagtttgc tgatggctag tagggt                                           26

<210> SEQ ID NO 46
<211> LENGTH: 31
<212> TYPE: DNA
<213> ORGANISM: Homo sapiens
```

```
<400> SEQUENCE: 46
tggtgggaaa atttcagttt catgagaagt g                                31

<210> SEQ ID NO 47
<211> LENGTH: 28
<212> TYPE: DNA
<213> ORGANISM: Homo sapiens

<400> SEQUENCE: 47
tccaggatgt aactagagag ctacgggt                                    28

<210> SEQ ID NO 48
<211> LENGTH: 31
<212> TYPE: RNA
<213> ORGANISM: Homo sapiens

<400> SEQUENCE: 48
agaagaucua gcuaagauca uugaugaagg u                                31

<210> SEQ ID NO 49
<211> LENGTH: 31
<212> TYPE: DNA
<213> ORGANISM: Artificial Sequence
<220> FEATURE:
<223> OTHER INFORMATION: synthetic polynucleotide primer

<400> SEQUENCE: 49
ttgctgtgat gactatctta ggacaccttt g                                31

<210> SEQ ID NO 50
<211> LENGTH: 28
<212> TYPE: DNA
<213> ORGANISM: Artificial Sequence
<220> FEATURE:
<223> OTHER INFORMATION: synthetic polynucleotide primer

<400> SEQUENCE: 50
cgtccatgat gttccgcaac tacctaca                                    28

<210> SEQ ID NO 51
<211> LENGTH: 31
<212> TYPE: DNA
<213> ORGANISM: Artificial Sequence
<220> FEATURE:
<223> OTHER INFORMATION: synthetic polynucleotide primer

<400> SEQUENCE: 51
ctgcagtgat gactttctta ggacaccttt g                                31

<210> SEQ ID NO 52
<211> LENGTH: 31
<212> TYPE: DNA
<213> ORGANISM: Artificial Sequence
<220> FEATURE:
<223> OTHER INFORMATION: synthetic polynucleotide primer

<400> SEQUENCE: 52
gaccaatgat gagtattctg gggtgtctga a                                31

<210> SEQ ID NO 53
<211> LENGTH: 20
<212> TYPE: DNA
<213> ORGANISM: Artificial Sequence
<220> FEATURE:
<223> OTHER INFORMATION: synthetic polynucleotide primer
```

```
<400> SEQUENCE: 53
ttctccacag tagcccagtc                                        20

<210> SEQ ID NO 54
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 54
cacttgcccc aaagtttcca                                        20

<210> SEQ ID NO 55
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 55
aggcaggaaa agttgatggt                                        20

<210> SEQ ID NO 56
<211> LENGTH: 21
<212> TYPE: DNA
<213> ORGANISM: Artificial Sequence
<220> FEATURE:
<223> OTHER INFORMATION: synthetic polynucleotide primer

<400> SEQUENCE: 56
tgtgccaaag tcacaggttt t                                      21

<210> SEQ ID NO 57
<211> LENGTH: 23
<212> TYPE: DNA
<213> ORGANISM: Artificial Sequence
<220> FEATURE:
<223> OTHER INFORMATION: synthetic polynucleotide primer

<400> SEQUENCE: 57
acagagaaag caagaactag ttg                                    23

<210> SEQ ID NO 58
<211> LENGTH: 22
<212> TYPE: DNA
<213> ORGANISM: Artificial Sequence
<220> FEATURE:
<223> OTHER INFORMATION: synthetic polynucleotide primer

<400> SEQUENCE: 58
gaaggtgaag gtcggagtca ac                                     22

<210> SEQ ID NO 59
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 59
gcccaagaag aaagcgatcc                                        20

<210> SEQ ID NO 60
```

-continued

```
<211> LENGTH: 25
<212> TYPE: DNA
<213> ORGANISM: Artificial Sequence
<220> FEATURE:
<223> OTHER INFORMATION: synthetic polynucleotide primer

<400> SEQUENCE: 60 gtttttgtg tttgtagaag aaagc                                          25

<210> SEQ ID NO 61
<211> LENGTH: 26
<212> TYPE: DNA
<213> ORGANISM: Artificial Sequence
<220> FEATURE:
<223> OTHER INFORMATION: synthetic polynucleotide primer

<400> SEQUENCE: 61 tttttgtgt tgtagaaga agtga                                           26

<210> SEQ ID NO 62
<211> LENGTH: 25
<212> TYPE: DNA
<213> ORGANISM: Artificial Sequence
<220> FEATURE:
<223> OTHER INFORMATION: synthetic polynucleotide primer

<400> SEQUENCE: 62 tttagttta gaattgggtt cgaag                                          25

<210> SEQ ID NO 63
<211> LENGTH: 23
<212> TYPE: DNA
<213> ORGANISM: Artificial Sequence
<220> FEATURE:
<223> OTHER INFORMATION: synthetic polynucleotide primer

<400> SEQUENCE: 63
tagttttaga attgggtttg aag                                           23

<210> SEQ ID NO 64
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 64
ggccatcccc tcctaaaact                                               20

<210> SEQ ID NO 65
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 65
gccagacatg cttcttcagg                                               20

<210> SEQ ID NO 66
<211> LENGTH: 22
<212> TYPE: DNA
<213> ORGANISM: Artificial Sequence
<220> FEATURE:
<223> OTHER INFORMATION: synthetic polynucleotide primer

<400> SEQUENCE: 66
```

```
agacactgaa gacgaaaagc tg                                              22

<210> SEQ ID NO 67
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 67
tgccatccag cttcttcaga                                                 20

<210> SEQ ID NO 68
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 68
ttgtcgtttc tgctgctgac                                                 20

<210> SEQ ID NO 69
<211> LENGTH: 22
<212> TYPE: DNA
<213> ORGANISM: Artificial Sequence
<220> FEATURE:
<223> OTHER INFORMATION: synthetic polynucleotide primer

<400> SEQUENCE: 69
cagagttaaa agcagccctg gt                                              22

<210> SEQ ID NO 70
<211> LENGTH: 21
<212> TYPE: DNA
<213> ORGANISM: Artificial Sequence
<220> FEATURE:
<223> OTHER INFORMATION: synthetic polynucleotide primer

<400> SEQUENCE: 70
gtaagtccat cgtgttgagc c                                               21

<210> SEQ ID NO 71
<211> LENGTH: 25
<212> TYPE: DNA
<213> ORGANISM: Artificial Sequence
<220> FEATURE:
<223> OTHER INFORMATION: synthetic polynucleotide primer

<400> SEQUENCE: 71
acttaccaac aataaatcca tcgta                                           25

<210> SEQ ID NO 72
<211> LENGTH: 25
<212> TYPE: DNA
<213> ORGANISM: Artificial Sequence
<220> FEATURE:
<223> OTHER INFORMATION: synthetic polynucleotide primer

<400> SEQUENCE: 72
acttaccaac aataaatcca tcata                                           25

<210> SEQ ID NO 73
<211> LENGTH: 24
<212> TYPE: DNA
```

```
<213> ORGANISM: Artificial Sequence
<220> FEATURE:
<223> OTHER INFORMATION: synthetic polynucleotide primer

<400> SEQUENCE: 73
aacaataccc aaaactcata cacg                                              24

<210> SEQ ID NO 74
<211> LENGTH: 25
<212> TYPE: DNA
<213> ORGANISM: Artificial Sequence
<220> FEATURE:
<223> OTHER INFORMATION: synthetic polynucleotide primer

<400> SEQUENCE: 74
aatacccaaa actcatacac actaa                                             25

<210> SEQ ID NO 75
<211> LENGTH: 26
<212> TYPE: RNA
<213> ORGANISM: Artificial Sequence
<220> FEATURE:
<223> OTHER INFORMATION: synthetic polynucleotide piRNA mimic

<400> SEQUENCE: 75
ugaggcgggc gccaugcaga cgggca                                            26

<210> SEQ ID NO 76
<211> LENGTH: 31
<212> TYPE: RNA
<213> ORGANISM: Artificial Sequence
<220> FEATURE:
<223> OTHER INFORMATION: synthetic polynucleotide piRNA mimic

<400> SEQUENCE: 76
ccucccaaag ugcugggauu acaggcguga g                                      31

<210> SEQ ID NO 77
<211> LENGTH: 32
<212> TYPE: RNA
<213> ORGANISM: Artificial Sequence
<220> FEATURE:
<223> OTHER INFORMATION: synthetic polynucleotide piRNA mimic

<400> SEQUENCE: 77
uggacggacg gauggccaga ugaaucaaaa cu                                     32

<210> SEQ ID NO 78
<211> LENGTH: 30
<212> TYPE: RNA
<213> ORGANISM: Artificial Sequence
<220> FEATURE:
<223> OTHER INFORMATION: synthetic polynucleotide piRNA mimic

<400> SEQUENCE: 78
aggguaacua ucaucaugug ucuggagguc                                        30

<210> SEQ ID NO 79
<211> LENGTH: 28
<212> TYPE: RNA
<213> ORGANISM: Artificial Sequence
<220> FEATURE:
<223> OTHER INFORMATION: synthetic polynucleotide piRNA mimic

<400> SEQUENCE: 79
ggauauggaa augagaggac ggacaagc                                          28
```

```
<210> SEQ ID NO 80
<211> LENGTH: 31
<212> TYPE: RNA
<213> ORGANISM: Artificial Sequence
<220> FEATURE:
<223> OTHER INFORMATION: synthetic polynucleotide piRNA mimic

<400> SEQUENCE: 80
uguggacugu cucaggaggc agaggggcac c                               31

<210> SEQ ID NO 81
<211> LENGTH: 26
<212> TYPE: DNA
<213> ORGANISM: Homo sapiens

<400> SEQUENCE: 81
tcagacattt ggtgtatgtg cttggc                                     26

<210> SEQ ID NO 82
<211> LENGTH: 31
<212> TYPE: DNA
<213> ORGANISM: Homo sapiens

<400> SEQUENCE: 82
atttggtgta tgtgcttggc tgaggagcca a                               31

<210> SEQ ID NO 83
<211> LENGTH: 27
<212> TYPE: DNA
<213> ORGANISM: Homo sapiens

<400> SEQUENCE: 83
ttggtgtatg tgcttggctg aggagcc                                    27

<210> SEQ ID NO 84
<211> LENGTH: 31
<212> TYPE: DNA
<213> ORGANISM: Homo sapiens

<400> SEQUENCE: 84
cgcacgtgtt aggacccgaa agatggtgaa c                               31

<210> SEQ ID NO 85
<211> LENGTH: 31
<212> TYPE: DNA
<213> ORGANISM: Homo sapiens

<400> SEQUENCE: 85
tggtgtatgt gcttggctga ggagccaatg g                               31

<210> SEQ ID NO 86
<211> LENGTH: 27
<212> TYPE: DNA
<213> ORGANISM: Homo sapiens

<400> SEQUENCE: 86
tccaggttcg actcctggct ggctcgc                                    27

<210> SEQ ID NO 87
<211> LENGTH: 29
<212> TYPE: DNA
<213> ORGANISM: Homo sapiens
```

```
<400> SEQUENCE: 87 agagagggc ccgtgccttg gaaagcgtc                                      29

<210> SEQ ID NO 88
<211> LENGTH: 28
<212> TYPE: DNA
<213> ORGANISM: Homo sapiens

<400> SEQUENCE: 88
tgagggttcg agtcccttcg tggtcgcc                                      28

<210> SEQ ID NO 89
<211> LENGTH: 29
<212> TYPE: DNA
<213> ORGANISM: Homo sapiens

<400> SEQUENCE: 89
tgggaaggag atggtcatgt ggcatgagt                                     29

<210> SEQ ID NO 90
<211> LENGTH: 27
<212> TYPE: DNA
<213> ORGANISM: Homo sapiens

<400> SEQUENCE: 90
aggggcccgt gccttggaaa gcgtcgc                                       27

<210> SEQ ID NO 91
<211> LENGTH: 29
<212> TYPE: DNA
<213> ORGANISM: Homo sapiens

<400> SEQUENCE: 91
gaggggcccg tgccttggaa agcgtcgcg                                     29

<210> SEQ ID NO 92
<211> LENGTH: 30
<212> TYPE: DNA
<213> ORGANISM: Homo sapiens

<400> SEQUENCE: 92
accgtcgtag ttccgaccat aaacgatgcc                                    30

<210> SEQ ID NO 93
<211> LENGTH: 30
<212> TYPE: DNA
<213> ORGANISM: Homo sapiens

<400> SEQUENCE: 93
gggagatgaa gaggacagtg actgagagac                                    30

<210> SEQ ID NO 94
<211> LENGTH: 28
<212> TYPE: DNA
<213> ORGANISM: Homo sapiens

<400> SEQUENCE: 94
atcagacccc agaaaaggtg ttggttga                                      28

<210> SEQ ID NO 95
<211> LENGTH: 29
<212> TYPE: DNA
<213> ORGANISM: Homo sapiens
```

<400> SEQUENCE: 95
ttccgggttc gagtcccggc ggagtcgcc                                    29

<210> SEQ ID NO 96
<211> LENGTH: 27
<212> TYPE: DNA
<213> ORGANISM: Homo sapiens

<400> SEQUENCE: 96 cagacccag aaaaggtgtt ggttgat                                       27

<210> SEQ ID NO 97
<211> LENGTH: 28
<212> TYPE: DNA
<213> ORGANISM: Homo sapiens

<400> SEQUENCE: 97
gcaataacag gtctgtgatg cccttaga                                     28

<210> SEQ ID NO 98
<211> LENGTH: 29
<212> TYPE: DNA
<213> ORGANISM: Homo sapiens

<400> SEQUENCE: 98
atcagacccc agaaaaggtg ttggttgat                                    29

<210> SEQ ID NO 99
<211> LENGTH: 31
<212> TYPE: DNA
<213> ORGANISM: Homo sapiens

<400> SEQUENCE: 99
gagaggggcc cgtgccttgg aaagcgtcgc g                                 31

<210> SEQ ID NO 100
<211> LENGTH: 28
<212> TYPE: DNA
<213> ORGANISM: Homo sapiens

<400> SEQUENCE: 100
tgccatggta atcctgctca gtacgaga                                     28

<210> SEQ ID NO 101
<211> LENGTH: 32
<212> TYPE: DNA
<213> ORGANISM: Homo sapiens

<400> SEQUENCE: 101
tattgatgcc gaactcagtg cggacacccc gt                                32

<210> SEQ ID NO 102
<211> LENGTH: 29
<212> TYPE: DNA
<213> ORGANISM: Homo sapiens

<400> SEQUENCE: 102
tgaggagcca atggggcgaa gctaccatc                                    29

<210> SEQ ID NO 103
<211> LENGTH: 30
<212> TYPE: DNA

```
<213> ORGANISM: Homo sapiens

<400> SEQUENCE: 103
tattgatgcc gaactcagtg cggacacccc                                    30

<210> SEQ ID NO 104
<211> LENGTH: 31
<212> TYPE: DNA
<213> ORGANISM: Homo sapiens

<400> SEQUENCE: 104
gtttagacgg gctcacatca ccccataaac a                                  31

<210> SEQ ID NO 105
<211> LENGTH: 28
<212> TYPE: DNA
<213> ORGANISM: Homo sapiens

<400> SEQUENCE: 105
gaatgcagcc caaagcgggt ggtaaact                                      28

<210> SEQ ID NO 106
<211> LENGTH: 30
<212> TYPE: DNA
<213> ORGANISM: Homo sapiens

<400> SEQUENCE: 106
ccggcccgga cacggacagg attgacagat                                    30

<210> SEQ ID NO 107
<211> LENGTH: 29
<212> TYPE: DNA
<213> ORGANISM: Homo sapiens

<400> SEQUENCE: 107
tccctggttc gatcccgggt ttcggcacc                                     29

<210> SEQ ID NO 108
<211> LENGTH: 26
<212> TYPE: DNA
<213> ORGANISM: Homo sapiens

<400> SEQUENCE: 108
ggggcgaagc taccatctgt gggatt                                        26

<210> SEQ ID NO 109
<211> LENGTH: 29
<212> TYPE: DNA
<213> ORGANISM: Homo sapiens

<400> SEQUENCE: 109
tctccatgta ggagggagta tggtgtttc                                     29

<210> SEQ ID NO 110
<211> LENGTH: 29
<212> TYPE: DNA
<213> ORGANISM: Homo sapiens

<400> SEQUENCE: 110
gggagatgaa gaggacagtg actgagaga                                     29

<210> SEQ ID NO 111
<211> LENGTH: 29
```

<212> TYPE: DNA
<213> ORGANISM: Homo sapiens

<400> SEQUENCE: 111
taccactcag tgatggaggg agactgtgc                                29

<210> SEQ ID NO 112
<211> LENGTH: 32
<212> TYPE: DNA
<213> ORGANISM: Homo sapiens

<400> SEQUENCE: 112
cccggcccgg acacggacag gattgacaga tt                            32

<210> SEQ ID NO 113
<211> LENGTH: 27
<212> TYPE: DNA
<213> ORGANISM: Homo sapiens

<400> SEQUENCE: 113
tgggaatgca gcccaaagcg ggtggta                                  27

<210> SEQ ID NO 114
<211> LENGTH: 31
<212> TYPE: DNA
<213> ORGANISM: Homo sapiens

<400> SEQUENCE: 114
agcaggacgg tggccatgga agtcggaatc c                             31

<210> SEQ ID NO 115
<211> LENGTH: 31
<212> TYPE: DNA
<213> ORGANISM: Homo sapiens

<400> SEQUENCE: 115
ggtcgctggt tcgaatccgg ctcgaaggac c                             31

<210> SEQ ID NO 116
<211> LENGTH: 29
<212> TYPE: DNA
<213> ORGANISM: Homo sapiens

<400> SEQUENCE: 116
acaggtctgt gatgccctta gatgtccgg                                29

<210> SEQ ID NO 117
<211> LENGTH: 31
<212> TYPE: DNA
<213> ORGANISM: Homo sapiens

<400> SEQUENCE: 117
ttgatgccga actcagtgcg gacacccgt c                              31

<210> SEQ ID NO 118
<211> LENGTH: 29
<212> TYPE: DNA
<213> ORGANISM: Homo sapiens

<400> SEQUENCE: 118
ctgggaatgc agcccaaagc gggtggtaa                                29

<210> SEQ ID NO 119

<211> LENGTH: 28
<212> TYPE: DNA
<213> ORGANISM: Homo sapiens

<400> SEQUENCE: 119
tcagtgatgg agggagactg tgccccaa                                          28

<210> SEQ ID NO 120
<211> LENGTH: 29
<212> TYPE: DNA
<213> ORGANISM: Homo sapiens

<400> SEQUENCE: 120
tgtcctcata aggagaggga gatttgagc                                         29

<210> SEQ ID NO 121
<211> LENGTH: 28
<212> TYPE: DNA
<213> ORGANISM: Homo sapiens

<400> SEQUENCE: 121
gagagagggg cccgtgcctt ggaaagtg                                          28

<210> SEQ ID NO 122
<211> LENGTH: 31
<212> TYPE: DNA
<213> ORGANISM: Homo sapiens

<400> SEQUENCE: 122
tcacccggcc cggacacgga caggattgac a                                      31

<210> SEQ ID NO 123
<211> LENGTH: 29
<212> TYPE: DNA
<213> ORGANISM: Homo sapiens

<400> SEQUENCE: 123
tgggtgtttc tcgcagaggg ggatttggc                                         29

<210> SEQ ID NO 124
<211> LENGTH: 30
<212> TYPE: DNA
<213> ORGANISM: Homo sapiens

<400> SEQUENCE: 124
tgcctagtgg gccacttttg gtaagcagaa                                        30

<210> SEQ ID NO 125
<211> LENGTH: 28
<212> TYPE: DNA
<213> ORGANISM: Homo sapiens

<400> SEQUENCE: 125
tcgctggttc gattccggct cgaaggac                                          28

<210> SEQ ID NO 126
<211> LENGTH: 29
<212> TYPE: DNA
<213> ORGANISM: Homo sapiens

<400> SEQUENCE: 126
tgtgaactga gacagaggga gataaagcc                                         29

```
<210> SEQ ID NO 127
<211> LENGTH: 26
<212> TYPE: DNA
<213> ORGANISM: Homo sapiens

<400> SEQUENCE: 127
tggggagatt cccgtgggaa atggga                                          26

<210> SEQ ID NO 128
<211> LENGTH: 29
<212> TYPE: DNA
<213> ORGANISM: Homo sapiens

<400> SEQUENCE: 128
tccaggaggg aaatgaaatg accttggca                                       29

<210> SEQ ID NO 129
<211> LENGTH: 27
<212> TYPE: DNA
<213> ORGANISM: Homo sapiens

<400> SEQUENCE: 129
tgggagaata catacgttgc tggcggg                                         27

<210> SEQ ID NO 130
<211> LENGTH: 28
<212> TYPE: DNA
<213> ORGANISM: Homo sapiens

<400> SEQUENCE: 130
agggaaattg ccataggaca ggtttggg                                        28

<210> SEQ ID NO 131
<211> LENGTH: 27
<212> TYPE: DNA
<213> ORGANISM: Homo sapiens

<400> SEQUENCE: 131
cgctggttcg attccggctc gaaggac                                         27

<210> SEQ ID NO 132
<211> LENGTH: 29
<212> TYPE: DNA
<213> ORGANISM: Homo sapiens

<400> SEQUENCE: 132
tgggaaggag atggtcatgt ggcatgaga                                       29

<210> SEQ ID NO 133
<211> LENGTH: 28
<212> TYPE: DNA
<213> ORGANISM: Homo sapiens

<400> SEQUENCE: 133
ttgatagatg aagatgggaa ggagatgg                                        28

<210> SEQ ID NO 134
<211> LENGTH: 29
<212> TYPE: DNA
<213> ORGANISM: Homo sapiens

<400> SEQUENCE: 134
ggtcagtcgg tcctgagaga tgggcgagc                                       29
```

<210> SEQ ID NO 135
<211> LENGTH: 30
<212> TYPE: DNA
<213> ORGANISM: Homo sapiens

<400> SEQUENCE: 135
tgccaaactt agtgcgggca cccggtcggc                                    30

<210> SEQ ID NO 136
<211> LENGTH: 31
<212> TYPE: DNA
<213> ORGANISM: Homo sapiens

<400> SEQUENCE: 136
tatgccagga gggaggttga cccgccaggt c                                  31

<210> SEQ ID NO 137
<211> LENGTH: 28
<212> TYPE: DNA
<213> ORGANISM: Homo sapiens

<400> SEQUENCE: 137
agctggagtg cagtggtgcg atcacggc                                      28

<210> SEQ ID NO 138
<211> LENGTH: 27
<212> TYPE: DNA
<213> ORGANISM: Homo sapiens

<400> SEQUENCE: 138
tcacccaggc tagagtgcag tggtgca                                       27

<210> SEQ ID NO 139
<211> LENGTH: 28
<212> TYPE: DNA
<213> ORGANISM: Homo sapiens

<400> SEQUENCE: 139
gggcagaagt tgggtgtcag tgatggga                                      28

<210> SEQ ID NO 140
<211> LENGTH: 30
<212> TYPE: DNA
<213> ORGANISM: Homo sapiens

<400> SEQUENCE: 140
tggtgtgatc tcggctcact gcaacctcct                                    30

<210> SEQ ID NO 141
<211> LENGTH: 30
<212> TYPE: DNA
<213> ORGANISM: Homo sapiens

<400> SEQUENCE: 141
taggcaagaa ggaagggaga agacacaagc                                    30

<210> SEQ ID NO 142
<211> LENGTH: 27
<212> TYPE: DNA
<213> ORGANISM: Homo sapiens

<400> SEQUENCE: 142
agggaaagac aggttttgga taagggg                                       27

```
<210> SEQ ID NO 143
<211> LENGTH: 30
<212> TYPE: DNA
<213> ORGANISM: Homo sapiens

<400> SEQUENCE: 143
tgttgataga tgaagatggg aaggagatgt                              30

<210> SEQ ID NO 144
<211> LENGTH: 30
<212> TYPE: DNA
<213> ORGANISM: Homo sapiens

<400> SEQUENCE: 144
tgccaggagg gaggttgacc cgccaggtcc                              30

<210> SEQ ID NO 145
<211> LENGTH: 28
<212> TYPE: DNA
<213> ORGANISM: Homo sapiens

<400> SEQUENCE: 145
ttgaggaact gaaacgacag gagggcga                                28

<210> SEQ ID NO 146
<211> LENGTH: 30
<212> TYPE: DNA
<213> ORGANISM: Homo sapiens

<400> SEQUENCE: 146
tggaagctca ggtgtgaggg agactcagaa                              30

<210> SEQ ID NO 147
<211> LENGTH: 28
<212> TYPE: DNA
<213> ORGANISM: Homo sapiens

<400> SEQUENCE: 147
tgtgctggga ggagagtcta actgtaac                                28

<210> SEQ ID NO 148
<211> LENGTH: 26
<212> TYPE: DNA
<213> ORGANISM: Homo sapiens

<400> SEQUENCE: 148
tgagagaggg agactctgtg cactcc                                  26

<210> SEQ ID NO 149
<211> LENGTH: 32
<212> TYPE: DNA
<213> ORGANISM: Homo sapiens

<400> SEQUENCE: 149
ggttagtttt accctactga tgatgtgttg tt                           32

<210> SEQ ID NO 150
<211> LENGTH: 32
<212> TYPE: DNA
<213> ORGANISM: Homo sapiens

<400> SEQUENCE: 150
```
tgggggagac acttaatgca aaacgcaaga at                32

<210> SEQ ID NO 151
<211> LENGTH: 30
<212> TYPE: DNA
<213> ORGANISM: Homo sapiens

<400> SEQUENCE: 151
tgcaatggtc taggggagaa aaactcactc                   30

<210> SEQ ID NO 152
<211> LENGTH: 30
<212> TYPE: DNA
<213> ORGANISM: Homo sapiens

<400> SEQUENCE: 152
aggttagttt taccctactg atgatgtgtt                   30

<210> SEQ ID NO 153
<211> LENGTH: 26
<212> TYPE: DNA
<213> ORGANISM: Homo sapiens

<400> SEQUENCE: 153
aggaaaggca aagggaagag agatgc                       26

<210> SEQ ID NO 154
<211> LENGTH: 31
<212> TYPE: DNA
<213> ORGANISM: Homo sapiens

<400> SEQUENCE: 154
gacgaggtgg ccgagtggtt aaggcaatgg a                 31

<210> SEQ ID NO 155
<211> LENGTH: 31
<212> TYPE: DNA
<213> ORGANISM: Homo sapiens

<400> SEQUENCE: 155
caccttggga ggccaaggca ggcagatcat c                 31

<210> SEQ ID NO 156
<211> LENGTH: 30
<212> TYPE: DNA
<213> ORGANISM: Homo sapiens

<400> SEQUENCE: 156
gacgaggtgg ccgagtggtt aaggcaatgg                   30

<210> SEQ ID NO 157
<211> LENGTH: 26
<212> TYPE: DNA
<213> ORGANISM: Homo sapiens

<400> SEQUENCE: 157
gagcgggaag agactggaga tgagga                       26

<210> SEQ ID NO 158
<211> LENGTH: 30
<212> TYPE: DNA
<213> ORGANISM: Homo sapiens

<400> SEQUENCE: 158 tgacccagg aggcggaagt tgcagtgagc                                    30

<210> SEQ ID NO 159
<211> LENGTH: 31
<212> TYPE: DNA
<213> ORGANISM: Homo sapiens

<400> SEQUENCE: 159
gggggtgtag ctcagtggta gagcgcgtgc t                                 31

<210> SEQ ID NO 160
<211> LENGTH: 30
<212> TYPE: DNA
<213> ORGANISM: Homo sapiens

<400> SEQUENCE: 160
tgtgacgtca ggtgagaagg gagggcccgt                                   30

<210> SEQ ID NO 161
<211> LENGTH: 29
<212> TYPE: DNA
<213> ORGANISM: Homo sapiens

<400> SEQUENCE: 161
tagttgggtg caaggctggg gtgggcggg                                    29

<210> SEQ ID NO 162
<211> LENGTH: 29
<212> TYPE: DNA
<213> ORGANISM: Homo sapiens

<400> SEQUENCE: 162
gggaaagata cggtcctcat gaggagggg                                    29

<210> SEQ ID NO 163
<211> LENGTH: 26
<212> TYPE: DNA
<213> ORGANISM: Homo sapiens

<400> SEQUENCE: 163
tggaggcggg gatgagtgtg aattta                                       26

<210> SEQ ID NO 164
<211> LENGTH: 31
<212> TYPE: DNA
<213> ORGANISM: Homo sapiens

<400> SEQUENCE: 164
taagaagtgg gtgggtggga ggagaaagag c                                 31

<210> SEQ ID NO 165
<211> LENGTH: 29
<212> TYPE: DNA
<213> ORGANISM: Homo sapiens

<400> SEQUENCE: 165
tcccagtata gggttggagg aggagctta                                    29

<210> SEQ ID NO 166
<211> LENGTH: 30
<212> TYPE: DNA
<213> ORGANISM: Homo sapiens -continued

```
<400> SEQUENCE: 166
tgaggcctag caaagggtgg agggtgggag                                30

<210> SEQ ID NO 167
<211> LENGTH: 31
<212> TYPE: DNA
<213> ORGANISM: Homo sapiens

<400> SEQUENCE: 167
ggggatgtag ctcagtggta gagcgcatgc t                              31

<210> SEQ ID NO 168
<211> LENGTH: 27
<212> TYPE: DNA
<213> ORGANISM: Homo sapiens

<400> SEQUENCE: 168
gggcattgga gggacaattt ggaaggg                                   27

<210> SEQ ID NO 169
<211> LENGTH: 30
<212> TYPE: DNA
<213> ORGANISM: Homo sapiens

<400> SEQUENCE: 169
tcaaatagga accaggagta cgggaggagc                                30

<210> SEQ ID NO 170
<211> LENGTH: 30
<212> TYPE: DNA
<213> ORGANISM: Homo sapiens

<400> SEQUENCE: 170
gggggtgtag ctcagtggta gagcgcgtgc                                30

<210> SEQ ID NO 171
<211> LENGTH: 32
<212> TYPE: DNA
<213> ORGANISM: Homo sapiens

<400> SEQUENCE: 171 gggggtgta gctcagtggt agagcgcgtg ct                              32

<210> SEQ ID NO 172
<211> LENGTH: 32
<212> TYPE: DNA
<213> ORGANISM: Homo sapiens

<400> SEQUENCE: 172
agcgttggtg gtatagtggt gagcatagct gc                             32

<210> SEQ ID NO 173
<211> LENGTH: 28
<212> TYPE: DNA
<213> ORGANISM: Homo sapiens

<400> SEQUENCE: 173
gaggaggaga acaggggtcc tggtggtc                                  28

<210> SEQ ID NO 174
<211> LENGTH: 30
<212> TYPE: DNA
<213> ORGANISM: Homo sapiens
```

<400> SEQUENCE: 174
cggaaggtcc tggaagaagg gcgggagaga                                    30

<210> SEQ ID NO 175
<211> LENGTH: 28
<212> TYPE: DNA
<213> ORGANISM: Homo sapiens

<400> SEQUENCE: 175
tccatggggt gggggtgag tcacagca                                       28

<210> SEQ ID NO 176
<211> LENGTH: 27
<212> TYPE: DNA
<213> ORGANISM: Homo sapiens

<400> SEQUENCE: 176
gaacaaggga agagtgggcg tggaggg                                       27

<210> SEQ ID NO 177
<211> LENGTH: 28
<212> TYPE: DNA
<213> ORGANISM: Homo sapiens

<400> SEQUENCE: 177
tgggacagga ggcactgggg tgggtgga                                      28

<210> SEQ ID NO 178
<211> LENGTH: 28
<212> TYPE: DNA
<213> ORGANISM: Homo sapiens

<400> SEQUENCE: 178
agagatagca gagtggcgca gcggaagc                                      28

<210> SEQ ID NO 179
<211> LENGTH: 29
<212> TYPE: DNA
<213> ORGANISM: Homo sapiens

<400> SEQUENCE: 179
gaggagccac atgtccttat ggggagaga                                     29

<210> SEQ ID NO 180
<211> LENGTH: 29
<212> TYPE: DNA
<213> ORGANISM: Homo sapiens

<400> SEQUENCE: 180
tgcggtgagg ggcggagctg gaacctcgg                                     29

<210> SEQ ID NO 181
<211> LENGTH: 31
<212> TYPE: DNA
<213> ORGANISM: Homo sapiens

<400> SEQUENCE: 181 gggggtgta gctcagtggt agagcgcgtg c                                   31

<210> SEQ ID NO 182
<211> LENGTH: 29
<212> TYPE: DNA

```
<213> ORGANISM: Homo sapiens

<400> SEQUENCE: 182
agcgttggtg gtatagtggt gagcatagc                                    29

<210> SEQ ID NO 183
<211> LENGTH: 32
<212> TYPE: DNA
<213> ORGANISM: Homo sapiens

<400> SEQUENCE: 183
gggtttgggg tggatggagg gtgtgggatg ga                                32

<210> SEQ ID NO 184
<211> LENGTH: 26
<212> TYPE: DNA
<213> ORGANISM: Homo sapiens

<400> SEQUENCE: 184
gcattggtgg tatagtggtg agcata                                       26

<210> SEQ ID NO 185
<211> LENGTH: 32
<212> TYPE: DNA
<213> ORGANISM: Homo sapiens

<400> SEQUENCE: 185
gggggtgtag ctcagtggta gagcgcgtgc tt                                32

<210> SEQ ID NO 186
<211> LENGTH: 26
<212> TYPE: DNA
<213> ORGANISM: Homo sapiens

<400> SEQUENCE: 186
tccttgggca ggggaagggc agcacc                                       26

<210> SEQ ID NO 187
<211> LENGTH: 26
<212> TYPE: DNA
<213> ORGANISM: Homo sapiens

<400> SEQUENCE: 187
tgtagtcgtg gccgagtggt taaggc                                       26

<210> SEQ ID NO 188
<211> LENGTH: 28
<212> TYPE: DNA
<213> ORGANISM: Homo sapiens

<400> SEQUENCE: 188
aagagctgca ggggaactgg gagagggt                                     28

<210> SEQ ID NO 189
<211> LENGTH: 29
<212> TYPE: DNA
<213> ORGANISM: Homo sapiens

<400> SEQUENCE: 189
taggaggatg acatggagga ggacgacga                                    29

<210> SEQ ID NO 190
<211> LENGTH: 30
```

<212> TYPE: DNA
<213> ORGANISM: Homo sapiens

<400> SEQUENCE: 190
tggcagtgag ctgggcaggg aggaaggggt                30

<210> SEQ ID NO 191
<211> LENGTH: 32
<212> TYPE: DNA
<213> ORGANISM: Homo sapiens

<400> SEQUENCE: 191
tgccacgcca atgggaggac acaggtgggc gg              32

<210> SEQ ID NO 192
<211> LENGTH: 27
<212> TYPE: DNA
<213> ORGANISM: Homo sapiens

<400> SEQUENCE: 192
gaggctgaag ctggataggg aggtcgg                    27

<210> SEQ ID NO 193
<211> LENGTH: 30
<212> TYPE: DNA
<213> ORGANISM: Homo sapiens

<400> SEQUENCE: 193
gcacaggtga aagtggccga ggtggagggc                 30

<210> SEQ ID NO 194
<211> LENGTH: 28
<212> TYPE: DNA
<213> ORGANISM: Homo sapiens

<400> SEQUENCE: 194
tgggacagga ggcactgggg tgggtgaa                   28

<210> SEQ ID NO 195
<211> LENGTH: 28
<212> TYPE: DNA
<213> ORGANISM: Homo sapiens

<400> SEQUENCE: 195
gcattggtgg tatagtggta agcatagc                   28

<210> SEQ ID NO 196
<211> LENGTH: 30
<212> TYPE: DNA
<213> ORGANISM: Homo sapiens

<400> SEQUENCE: 196
tcaaagcctg atgcagaagg aaggagggt                  30

<210> SEQ ID NO 197
<211> LENGTH: 30
<212> TYPE: DNA
<213> ORGANISM: Homo sapiens

<400> SEQUENCE: 197
tcaattctgt agagtcaggg gtgaggagga                 30

<210> SEQ ID NO 198

```
<211> LENGTH: 29
<212> TYPE: DNA
<213> ORGANISM: Homo sapiens

<400> SEQUENCE: 198
tgggaaggag gaggacaagc agagctggg                                  29

<210> SEQ ID NO 199
<211> LENGTH: 29
<212> TYPE: DNA
<213> ORGANISM: Homo sapiens

<400> SEQUENCE: 199
tcaataaggg tggaagcgac ggggaaaga                                  29

<210> SEQ ID NO 200
<211> LENGTH: 28
<212> TYPE: DNA
<213> ORGANISM: Homo sapiens

<400> SEQUENCE: 200
gcattggtgg tatagtggtg agcatagc                                   28

<210> SEQ ID NO 201
<211> LENGTH: 26
<212> TYPE: DNA
<213> ORGANISM: Homo sapiens

<400> SEQUENCE: 201
tgtagagata aagctgagga ggaggc                                     26

<210> SEQ ID NO 202
<211> LENGTH: 27
<212> TYPE: DNA
<213> ORGANISM: Homo sapiens

<400> SEQUENCE: 202
agcgttggtg gtatagtggt gagcata                                    27

<210> SEQ ID NO 203
<211> LENGTH: 30
<212> TYPE: DNA
<213> ORGANISM: Homo sapiens

<400> SEQUENCE: 203
ggagagggtg tgggggcgt gtgggatgtc                                  30

<210> SEQ ID NO 204
<211> LENGTH: 28
<212> TYPE: DNA
<213> ORGANISM: Homo sapiens

<400> SEQUENCE: 204
tgggaagaga gagcaaggag ctggaggg                                   28

<210> SEQ ID NO 205
<211> LENGTH: 29
<212> TYPE: DNA
<213> ORGANISM: Homo sapiens

<400> SEQUENCE: 205
tgaaatggac aggaagggtg ggcgggcct                                  29
```

```
<210> SEQ ID NO 206
<211> LENGTH: 28
<212> TYPE: DNA
<213> ORGANISM: Homo sapiens

<400> SEQUENCE: 206
taacaagtac ggggaagaga gggtgatc                                          28

<210> SEQ ID NO 207
<211> LENGTH: 30
<212> TYPE: DNA
<213> ORGANISM: Homo sapiens

<400> SEQUENCE: 207
tgaaatggac aggaagggtg ggcgggcctt                                        30

<210> SEQ ID NO 208
<211> LENGTH: 31
<212> TYPE: DNA
<213> ORGANISM: Homo sapiens

<400> SEQUENCE: 208
gtagtcgtgg ccgagtggtt aaggctatgg a                                      31

<210> SEQ ID NO 209
<211> LENGTH: 29
<212> TYPE: DNA
<213> ORGANISM: Homo sapiens

<400> SEQUENCE: 209
ttggggaaga cacggacggg gcccagacc                                         29

<210> SEQ ID NO 210
<211> LENGTH: 27
<212> TYPE: DNA
<213> ORGANISM: Homo sapiens

<400> SEQUENCE: 210
tcctcagcat cggtgagaag gggcggc                                           27

<210> SEQ ID NO 211
<211> LENGTH: 26
<212> TYPE: DNA
<213> ORGANISM: Homo sapiens

<400> SEQUENCE: 211
tgggatgaga agtctggagg gcacgg                                            26

<210> SEQ ID NO 212
<211> LENGTH: 29
<212> TYPE: DNA
<213> ORGANISM: Homo sapiens

<400> SEQUENCE: 212
tacacagaac gaacggggca gagaggtgg                                         29

<210> SEQ ID NO 213
<211> LENGTH: 26
<212> TYPE: DNA
<213> ORGANISM: Homo sapiens

<400> SEQUENCE: 213
tgaaggaact gagggggcagg gaaaga                                           26
```

```
<210> SEQ ID NO 214
<211> LENGTH: 31
<212> TYPE: DNA
<213> ORGANISM: Homo sapiens

<400> SEQUENCE: 214
gttaagatgg cagagcccgg taatcgcata a                              31

<210> SEQ ID NO 215
<211> LENGTH: 28
<212> TYPE: DNA
<213> ORGANISM: Homo sapiens

<400> SEQUENCE: 215
gggtggaagc gatgagttct ccaggggc                                  28

<210> SEQ ID NO 216
<211> LENGTH: 26
<212> TYPE: DNA
<213> ORGANISM: Homo sapiens

<400> SEQUENCE: 216
agccataaat acaacgcagg ggggcc                                    26

<210> SEQ ID NO 217
<211> LENGTH: 28
<212> TYPE: DNA
<213> ORGANISM: Homo sapiens

<400> SEQUENCE: 217
caagagttcg gggaaagacg gacaggac                                  28

<210> SEQ ID NO 218
<211> LENGTH: 29
<212> TYPE: DNA
<213> ORGANISM: Homo sapiens

<400> SEQUENCE: 218
tattggactg aacaaagggg ggcaaacac                                 29

<210> SEQ ID NO 219
<211> LENGTH: 28
<212> TYPE: DNA
<213> ORGANISM: Homo sapiens

<400> SEQUENCE: 219
tacacagaac gaacggggca gagaggtg                                  28

<210> SEQ ID NO 220
<211> LENGTH: 29
<212> TYPE: DNA
<213> ORGANISM: Homo sapiens

<400> SEQUENCE: 220
gctgaggaag agtggacgga cggatggca                                 29

<210> SEQ ID NO 221
<211> LENGTH: 26
<212> TYPE: DNA
<213> ORGANISM: Homo sapiens

<400> SEQUENCE: 221 caccagggggg gtagggccca aaggga                                   26
```

```
<210> SEQ ID NO 222
<211> LENGTH: 28
<212> TYPE: DNA
<213> ORGANISM: Homo sapiens

<400> SEQUENCE: 222
ggatatggaa atgagaggac ggacaagc                                      28

<210> SEQ ID NO 223
<211> LENGTH: 31
<212> TYPE: DNA
<213> ORGANISM: Homo sapiens

<400> SEQUENCE: 223
tgtggactgt ctcaggaggc agaggggcac c                                  31

<210> SEQ ID NO 224
<211> LENGTH: 32
<212> TYPE: DNA
<213> ORGANISM: Homo sapiens

<400> SEQUENCE: 224
tggacggacg gatggccaga tgaatcaaaa ct                                 32

<210> SEQ ID NO 225
<211> LENGTH: 26
<212> TYPE: DNA
<213> ORGANISM: Homo sapiens

<400> SEQUENCE: 225
tgaggcgggc gccatgcaga cgggca                                        26

<210> SEQ ID NO 226
<211> LENGTH: 23
<212> TYPE: DNA
<213> ORGANISM: Artificial Sequence
<220> FEATURE:
<223> OTHER INFORMATION: synthetic polynucleotide primer

<400> SEQUENCE: 226
ctagctaaga tcattgatga agg                                           23

<210> SEQ ID NO 227
<211> LENGTH: 22
<212> TYPE: DNA
<213> ORGANISM: Artificial Sequence
<220> FEATURE:
<223> OTHER INFORMATION: synthetic polynucleotide primer

<400> SEQUENCE: 227
cagctatgaa gtctatgaat cc                                            22

<210> SEQ ID NO 228
<211> LENGTH: 23
<212> TYPE: DNA
<213> ORGANISM: Artificial Sequence
<220> FEATURE:
<223> OTHER INFORMATION: synthetic polynucleotide primer

<400> SEQUENCE: 228
ctccagtagt atcctctgtt ttc                                           23

<210> SEQ ID NO 229
```

```
<211> LENGTH: 18
<212> TYPE: DNA
<213> ORGANISM: Artificial Sequence
<220> FEATURE:
<223> OTHER INFORMATION: synthetic polynucleotide primer

<400> SEQUENCE: 229
tgctgaagtt tgctgctg                                                  18

<210> SEQ ID NO 230
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 230
tggattgaag gacgcaaagt                                                20

<210> SEQ ID NO 231
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 231
acgcaaattc gtgaagcgtt                                                20

<210> SEQ ID NO 232
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 232
ttcatccagg atcgagcagg                                                20

<210> SEQ ID NO 233
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 233
acggcaaggt ggagatcatc                                                20

<210> SEQ ID NO 234
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 234
agcagcaaag aactttcccg                                                20

<210> SEQ ID NO 235
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 235
```
gctatcagtc tgtcagctgc                                         20

<210> SEQ ID NO 236
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 236
gttcagggat aactcggcca                                         20

<210> SEQ ID NO 237
<211> LENGTH: 22
<212> TYPE: DNA
<213> ORGANISM: Artificial Sequence
<220> FEATURE:
<223> OTHER INFORMATION: synthetic polynucleotide primer

<400> SEQUENCE: 237
gaaggtgaag gtcggagtca ac                                      22

<210> SEQ ID NO 238
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 238
gcaatcatcc tctgcagctc                                         20

<210> SEQ ID NO 239
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 239
gcttgtctcc gtcgttgatc                                         20

<210> SEQ ID NO 240
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 240
cacgtccttc ttctcttgcg                                         20

<210> SEQ ID NO 241
<211> LENGTH: 20
<212> TYPE: DNA
<213> ORGANISM: Artificial Sequence
<220> FEATURE:
<223> OTHER INFORMATION: synthetic polynucleotide primer

<400> SEQUENCE: 241
cttcgtctag gagctggagg                                         20

<210> SEQ ID NO 242
<211> LENGTH: 20
<212> TYPE: DNA

```
<213> ORGANISM: Artificial Sequence
<220> FEATURE:
<223> OTHER INFORMATION: synthetic polynucleotide primer

<400> SEQUENCE: 242
ttcgaacgtg cactgaaagg                                           20

<210> SEQ ID NO 243
<211> LENGTH: 22
<212> TYPE: DNA
<213> ORGANISM: Artificial Sequence
<220> FEATURE:
<223> OTHER INFORMATION: synthetic polynucleotide primer

<400> SEQUENCE: 243
cagagttaaa agcagccctg gt                                        22

<210> SEQ ID NO 244
<211> LENGTH: 31
<212> TYPE: RNA
<213> ORGANISM: Artificial Sequence
<220> FEATURE:
<223> OTHER INFORMATION: synthetic piRNA mimic (piR-598 variant)

<400> SEQUENCE: 244
agaagaucua gcuaagauca uugaugaaag u                              31
```